(12) United States Patent
Shelton, IV et al.

(10) Patent No.: US 11,911,030 B2
(45) Date of Patent: Feb. 27, 2024

(54) COMMUNICATION CAPABILITY OF A SURGICAL DEVICE WITH COMPONENT

(71) Applicant: Cilag GmbH International, Zug (CH)

(72) Inventors: Frederick E. Shelton, IV, New Vienna, OH (US); Patrick L. Creamer, New Orleans, LA (US); Shane R. Adams, Lebanon, OH (US); Jason L. Harris, Lebanon, OH (US); Kevin M. Fiebig, Cincinnati, OH (US); Michael J. Vendely, Lebanon, OH (US)

(73) Assignee: Cilag GmbH International, Zug (CH)

( * ) Notice: Subject to any disclaimer, the term of this patent is extended or adjusted under 35 U.S.C. 154(b) by 585 days.

(21) Appl. No.: 17/062,501

(22) Filed: Oct. 2, 2020

(65) Prior Publication Data

US 2022/0104813 A1 Apr. 7, 2022

(51) Int. Cl.
*A61B 17/072* (2006.01)
*A61B 17/00* (2006.01)
(Continued)

(52) U.S. Cl.
CPC ...... *A61B 17/072* (2013.01); *A61B 17/07207* (2013.01); *A61B 17/068* (2013.01);
(Continued)

(58) Field of Classification Search
CPC ............... A61B 17/068; A61B 17/072; A61B 17/07207; A61B 17/115; A61B 17/00234; A61B 2017/07214; A61B 2017/00017; A61B 2017/00022; A61B 2017/00398; A61B 2017/00477; A61B 2017/07228;
(Continued)

(56) References Cited

U.S. PATENT DOCUMENTS 5,518,164 A * 5/1996 Hooven ........... A61B 17/07207
227/176.1
8,210,411 B2 * 7/2012 Yates .................. A61B 17/068
227/19
(Continued)

FOREIGN PATENT DOCUMENTS

CA 3089858 A1 8/2019
EP 2491872 A1 8/2012
(Continued)

OTHER PUBLICATIONS

U.S. Appl. No. 17/062,504, filed Oct. 2, 2020, Shelton, et al.

*Primary Examiner* — Scott A Smith
(74) *Attorney, Agent, or Firm* — Condo Roccia Koptiw LLP

(57) ABSTRACT

A surgical instrument controls communication capabilities between the surgical instrument and a removeable component. The surgical instrument may determine parameters associated with the surgical instrument and the removable component. Based on the parameters, the surgical instrument determines a level or tier of communication between the surgical instrument and the removable component. The surgical instrument may determine to configure one or more of the following levels: one-way static communication with the component; two-way communication with the component; real-time two-way communication with the component; and communication with a surgical hub.

18 Claims, 44 Drawing Sheets

(51) Int. Cl.
   *A61B 90/98* (2016.01)
   *A61B 34/30* (2016.01)
   *A61B 34/00* (2016.01)
   *A61B 17/29* (2006.01)
   *A61B 17/068* (2006.01)

(52) U.S. Cl.
   CPC ............ *A61B 34/30* (2016.02); *A61B 34/71* (2016.02); *A61B 90/98* (2016.02); *A61B 2017/00022* (2013.01); *A61B 2017/00477* (2013.01); *A61B 2017/00734* (2013.01); *A61B 2017/07214* (2013.01); *A61B 2017/07271* (2013.01); *A61B 2017/2927* (2013.01); *A61B 2560/0204* (2013.01); *A61B 2560/0271* (2013.01)

(58) Field of Classification Search
   CPC .... A61B 2017/2927; A61B 2017/2929; A61B 90/90; A61B 90/98; A61B 34/30; A61B 34/71; A61B 34/76
   USPC .............. 227/19, 176.1, 175.1, 175.2, 175.3; 606/1, 139, 213, 219
   See application file for complete search history.

(56) References Cited

U.S. PATENT DOCUMENTS

| | | | |
|---|---|---|---|
| 8,476,227 B2 | 7/2013 | Kaplan et al. | |
| 9,011,427 B2 | 4/2015 | Price et al. | |
| 9,072,535 B2 | 7/2015 | Shelton et al. | |
| 9,123,155 B2 | 9/2015 | Cunningham et al. | |
| 9,250,172 B2 | 2/2016 | Harris et al. | |
| 9,345,481 B2 | 5/2016 | Hall et al. | |
| 9,538,962 B1 | 1/2017 | Hannaford et al. | |
| 10,492,783 B2 | 12/2019 | Shelton, IV et al. | |
| 10,695,081 B2 | 6/2020 | Shelton et al. | |
| 11,123,074 B2 | 9/2021 | Adams et al. | |
| 11,185,331 B2 | 11/2021 | Adams et al. | |
| 11,284,963 B2 | 3/2022 | Shelton, IV et al. | |
| 2005/0033117 A1 | 2/2005 | Ozaki et al. | |
| 2008/0319275 A1 | 12/2008 | Chiu et al. | |
| 2009/0090763 A1* | 4/2009 | Zemlok | A61B 17/07207 227/175.2 |
| 2009/0248022 A1 | 10/2009 | Falkenstein et al. | |
| 2010/0089970 A1* | 4/2010 | Smith | A61B 17/0686 227/175.1 |
| 2011/0017801 A1* | 1/2011 | Zemlok | A61B 17/07207 227/175.1 |
| 2011/0144640 A1* | 6/2011 | Heinrich | A61B 17/062 606/41 |
| 2012/0182409 A1 | 7/2012 | Moriyama et al. | |
| 2012/0205419 A1* | 8/2012 | Weir | A61B 17/0686 227/175.1 |
| 2012/0253329 A1 | 10/2012 | Zemlok et al. | |
| 2013/0116218 A1 | 5/2013 | Kaplan et al. | |
| 2014/0087999 A1 | 3/2014 | Kaplan et al. | |
| 2014/0166728 A1 | 6/2014 | Swayze et al. | |
| 2014/0175150 A1* | 6/2014 | Shelton, IV | A61B 17/07207 227/176.1 |
| 2014/0224856 A1* | 8/2014 | Smith | A61B 17/115 227/175.1 |
| 2014/0246479 A1* | 9/2014 | Baber | A61B 18/1445 227/180.1 |
| 2014/0263541 A1 | 9/2014 | Leimbach et al. | |
| 2014/0263551 A1 | 9/2014 | Hall et al. | |
| 2014/0263552 A1 | 9/2014 | Hall et al. | |
| 2014/0305994 A1* | 10/2014 | Parihar | A61B 17/07207 227/180.1 |
| 2015/0053749 A1* | 2/2015 | Shelton, IV | A61B 90/96 227/181.1 |
| 2015/0223890 A1 | 8/2015 | Miller et al. | |
| 2015/0272575 A1* | 10/2015 | Leimbach | A61B 90/96 227/175.3 |
| 2016/0066916 A1* | 3/2016 | Overmyer | H02H 3/207 227/176.1 |
| 2016/0174969 A1* | 6/2016 | Kerr | A61B 17/068 227/180.1 |
| 2016/0249915 A1* | 9/2016 | Beckman | A61B 17/1155 227/175.1 |
| 2016/0249919 A1* | 9/2016 | Savage | H01M 10/613 227/175.1 |
| 2016/0256156 A1 | 9/2016 | Shelton et al. | |
| 2016/0310134 A1* | 10/2016 | Contini | A61B 17/07207 |
| 2017/0172381 A1 | 6/2017 | Morimoto | |
| 2017/0296213 A1 | 10/2017 | Swensgard et al. | |
| 2017/0323062 A1 | 11/2017 | Djajadiningrat et al. | |
| 2018/0032130 A1 | 2/2018 | Meglan | |
| 2018/0098049 A1 | 4/2018 | Sugano et al. | |
| 2018/0353186 A1* | 12/2018 | Mozdzierz | A61B 17/320016 |
| 2018/0360452 A1 | 12/2018 | Shelton et al. | |
| 2019/0000478 A1 | 1/2019 | Messerly et al. | |
| 2019/0099180 A1 | 4/2019 | Leimbach et al. | |
| 2019/0104919 A1 | 4/2019 | Shelton, IV et al. | |
| 2019/0125361 A1 | 5/2019 | Shelton, IV et al. | |
| 2019/0125454 A1 | 5/2019 | Stokes et al. | |
| 2019/0200844 A1 | 7/2019 | Shelton et al. | |
| 2019/0200981 A1 | 7/2019 | Harris et al. | |
| 2019/0200996 A1 | 7/2019 | Shelton, IV et al. | |
| 2019/0200997 A1 | 7/2019 | Shelton, IV et al. | |
| 2019/0200998 A1 | 7/2019 | Shelton, IV et al. | |
| 2019/0201029 A1 | 7/2019 | Shelton, IV et al. | |
| 2019/0201034 A1 | 7/2019 | Shelton, IV et al. | |
| 2019/0201044 A1 | 7/2019 | Shelton, IV et al. | |
| 2019/0201102 A1 | 7/2019 | Shelton, IV et al. | |
| 2019/0201104 A1 | 7/2019 | Shelton, IV et al. | |
| 2019/0201115 A1 | 7/2019 | Shelton, IV et al. | |
| 2019/0201119 A1 | 7/2019 | Harris et al. | |
| 2019/0201129 A1 | 7/2019 | Shelton, IV et al. | |
| 2019/0201136 A1 | 7/2019 | Shelton et al. | |
| 2019/0201137 A1 | 7/2019 | Shelton et al. | |
| 2019/0201140 A1 | 7/2019 | Yates et al. | |
| 2019/0201141 A1 | 7/2019 | Shelton, IV et al. | |
| 2019/0201144 A1 | 7/2019 | Shelton, IV et al. | |
| 2019/0201146 A1 | 7/2019 | Shelton, IV et al. | |
| 2019/0204201 A1 | 7/2019 | Shelton, IV et al. | |
| 2019/0206003 A1 | 7/2019 | Harris et al. | |
| 2019/0206555 A1 | 7/2019 | Morgan et al. | |
| 2019/0206562 A1 | 7/2019 | Shelton, IV et al. | |
| 2019/0206563 A1 | 7/2019 | Shelton, IV et al. | |
| 2019/0206564 A1 | 7/2019 | Shelton, IV et al. | |
| 2019/0206565 A1 | 7/2019 | Shelton, IV | |
| 2019/0206566 A1 | 7/2019 | Shelton et al. | |
| 2019/0314015 A1 | 10/2019 | Shelton, IV et al. | |
| 2019/0388137 A1 | 12/2019 | Henrywood et al. | |
| 2020/0078078 A1 | 3/2020 | Henderson et al. | |
| 2020/0078079 A1 | 3/2020 | Morgan et al. | |
| 2020/0214571 A1 | 7/2020 | Bradbury et al. | |
| 2020/0405439 A1 | 12/2020 | Shelton, IV et al. | |
| 2021/0077110 A1 | 3/2021 | Adams et al. | |
| 2021/0077111 A1 | 3/2021 | Adams et al. | |
| 2021/0077112 A1 | 3/2021 | Adams et al. | |
| 2021/0196384 A1 | 7/2021 | Shelton, IV et al. | |
| 2021/0196423 A1 | 7/2021 | Shelton, IV et al. | |
| 2021/0196425 A1 | 7/2021 | Shelton, IV et al. | |
| 2021/0401533 A1 | 12/2021 | Im | |
| 2022/0104694 A1 | 4/2022 | Shelton, IV et al. | |
| 2022/0104713 A1 | 4/2022 | Shelton, IV | |
| 2022/0104765 A1 | 4/2022 | Shelton, IV et al. | |
| 2022/0104806 A1 | 4/2022 | Shelton, IV et al. | |
| 2022/0104807 A1 | 4/2022 | Shelton, IV et al. | |
| 2022/0104813 A1 | 4/2022 | Shelton, IV et al. | |
| 2022/0104814 A1 | 4/2022 | Shelton, IV et al. | |
| 2022/0104820 A1 | 4/2022 | Shelton, IV et al. | |
| 2022/0104821 A1 | 4/2022 | Shelton, IV et al. | |
| 2022/0104822 A1 | 4/2022 | Shelton, IV et al. | |
| 2022/0104843 A1 | 4/2022 | Shelton, IV et al. | |
| 2022/0104867 A1 | 4/2022 | Shelton, IV et al. | |
| 2022/0104889 A1 | 4/2022 | Shelton, IV et al. | |
| 2022/0104896 A1 | 4/2022 | Shelton, IV et al. | |
| 2022/0104897 A1 | 4/2022 | Shelton, IV et al. | |
| 2022/0104908 A1 | 4/2022 | Shelton, IV et al. | |
| 2022/0104910 A1 | 4/2022 | Shelton, IV et al. | |

(56) References Cited

U.S. PATENT DOCUMENTS

| | | |
|---|---|---|
| 2022/0104911 A1 | 4/2022 | Shelton, IV et al. |
| 2022/0104912 A1 | 4/2022 | Shelton, IV et al. |
| 2022/0108783 A1 | 4/2022 | Shelton, IV et al. |
| 2022/0108788 A1 | 4/2022 | Shelton, IV et al. |
| 2022/0108789 A1 | 4/2022 | Shelton, IV et al. |

FOREIGN PATENT DOCUMENTS

| | | |
|---|---|---|
| EP | 2659852 A2 | 11/2013 |
| EP | 3061405 A1 | 8/2016 |
| EP | 3064141 A1 | 9/2016 |
| EP | 3412225 A1 | 12/2018 |
| EP | 3449800 A1 | 3/2019 |
| EP | 3466348 A2 | 4/2019 |
| EP | 3506273 A1 | 7/2019 |
| EP | 3506299 A1 | 7/2019 |
| EP | 3547324 A1 | 10/2019 |
| EP | 3628207 A1 | 4/2020 |
| WO | 2015125447 A1 | 8/2015 |
| WO | 2016171947 A1 | 10/2016 |
| WO | WO 2019-130108 A1 | 7/2019 |
| WO | 2020101283 A1 | 5/2020 |
| WO | 2020154351 A1 | 7/2020 |

* cited by examiner

COMMUNICATION CAPABILITY OF A SURGICAL DEVICE WITH COMPONENT

CROSS-REFERENCE TO RELATED APPLICATIONS

This application is related to the following, filed contemporaneously, the contents of each of which are incorporated by reference herein:

U.S. patent application Ser. No. 17/062,504, filed Oct. 2, 2020, titled METHOD FOR OPERATING TIERED OPERATION MODES IN A SURGICAL SYSTEM.

BACKGROUND

Surgical instruments may incorporate removable components. For example, a surgical stapler instrument may comprise an end effector that receives a removable cartridge containing a plurality of spaced rows of staples. The removable cartridge is coupled with the surgical stapler instrument and the surgical stapler drives staples from the cartridge during a surgical procedure.

SUMMARY

Disclosed herein are techniques for controlling the communication capabilities between a surgical instrument and a removable component. A surgical instrument may be configured to determine parameters associated with one or more of the surgical instrument and the removable component. The surgical instrument may process values of parameters associated with, for example, the owner or operator of the device, hardware comprised in the surgical instrument and/or component, software comprised in the surgical instrument and/or component, and/or a purchase or subscription level associated with the surgical instrument and/or component.

The surgical instrument may determine, based upon the considered parameters, a communication capability between the surgical instrument and the component. For example, a surgical instrument may determine the type and degree of communication between the surgical instrument and a component based on a parameter indicating a purchase or subscription level associated with the surgical instrument or attached component. If a surgical instrument, such as a surgical stapler, or a removable component, such as a surgical staple cartridge, attached to the surgical instrument is associated with a low subscription level, the surgical stapler may determine that the surgical instrument may provide one-way static communication from the surgical component to the surgical instrument. If the surgical instrument or component is associated with a higher subscription level, the surgical instrument may determine that the surgical instrument may provide real-time two-way communication between the surgical instrument and the component.

A surgical instrument may determine the communication capability between the surgical instrument and component based on parameters relating to the hardware and/or software comprised in the surgical instrument and/or component. If a component attached to a surgical instrument is configured with outdated software, the surgical instrument may determine that the communication capability with the component may comprise one-way static communication from the component to the surgical instrument. If the component attached to the surgical instrument is configured with recently updated software, the surgical instrument may determine that the communication capability with the component may comprise two-way real-time communication.

The surgical instrument may communicate with the removable component consistent with the determined communication capability. If the surgical instrument determined the communication capability comprised one-way communication with the removable component, the surgical instrument performs one-way communication with the component. If the surgical instrument determined the communication comprised real-time two-way communication with the removable component, the surgical instrument performs real-time two-way communication.

DETAILED DESCRIPTION

Figure 1:
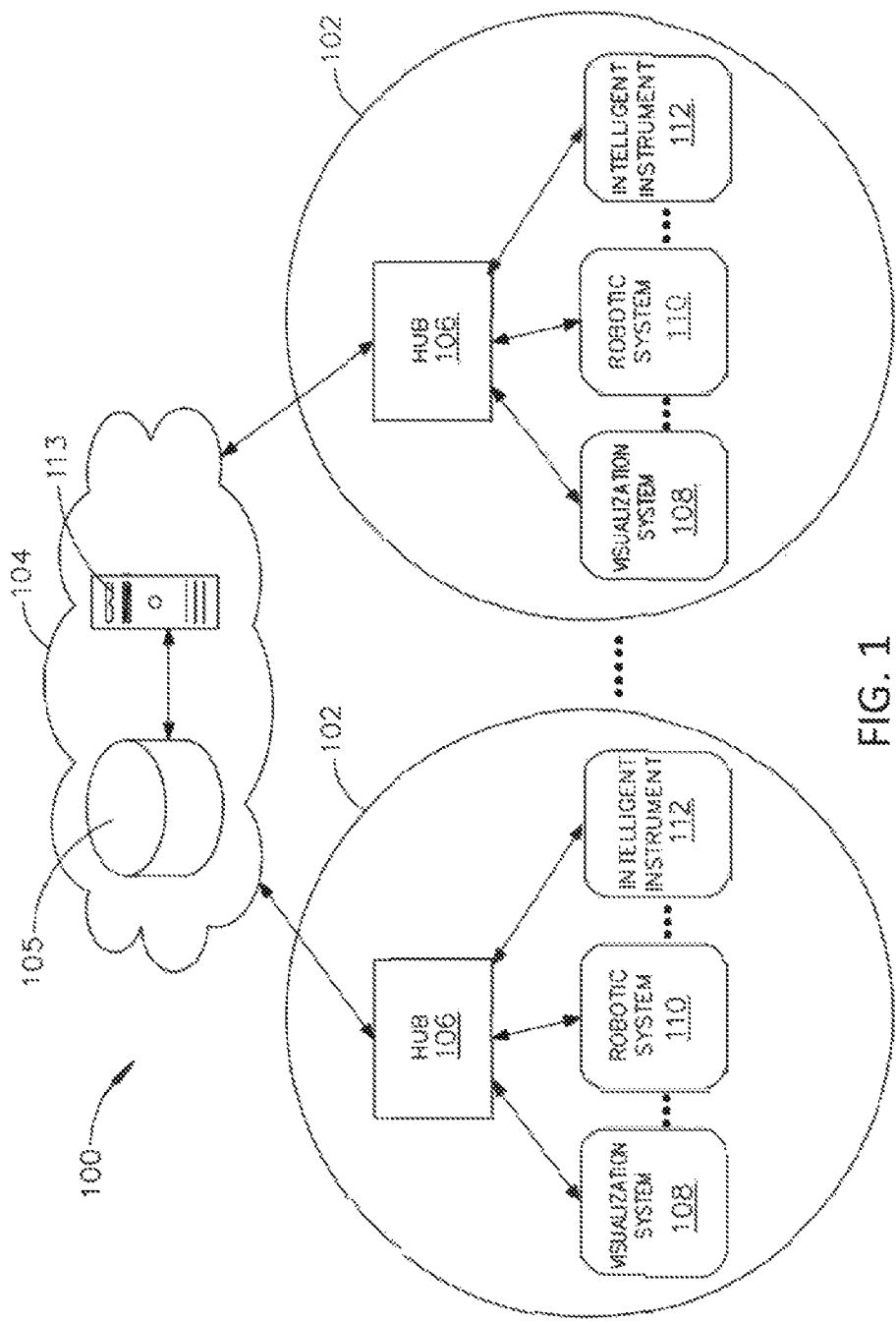
FIG. 1 is a block diagram of a computer-implemented interactive surgical system.

Applicant of the present application owns the following U.S. patent applications, patent publications, and patents, each of which is herein incorporated by reference in its entirety:

U.S. Patent Application Publication No. US 20190200981 (U.S. application Ser. No. 16/209,423, filed Dec. 4, 2018), titled "METHOD OF COMPRESSING TISSUE WITHIN A STAPLING DEVICE AND SIMULTANEOUSLY DISPLAYING THE LOCATION OF THE TISSUE WITHIN THE JAWS," published Jul. 4, 2019;

U.S. Pat. No. 9,072,535, titled "SURGICAL STAPLING INSTRUMENTS WITH ROTATABLE STAPLE DEPLOYMENT ARRANGEMENTS," issued Jul. 5, 2015;

U.S. Patent Application Publication No. US 20140263541 (U.S. application Ser. No. 13/803,086, filed Mar. 14, 2013), titled "ARTICULATABLE SURGICAL INSTRUMENT COMPRISING AN ARTICULATION LOCK," published Sep. 18, 2014;

U.S. Patent Application Publication No. US 20140263551 (U.S. application Ser. No. 13/800,025, filed Mar. 13, 2013), titled "STAPLE CARTRIDGE TISSUE THICKNESS SENSOR SYSTEM," published Sep. 18, 2014;

U.S. Patent Application Publication No. US 20140263552 (U.S. application Ser. No. 13/800,067, filed Mar. 13, 2013), titled "STAPLE CARTRIDGE TISSUE THICKNESS SENSOR SYSTEM," published Sep. 18, 2014;

U.S. Patent Application Publication No. US 20190000478 (U.S. application Ser. No. 15/636,096, filed Jun. 28, 2017), titled "SURGICAL SYSTEM COUPLABLE WITH STAPLE CARTRIDGE AND RADIO FREQUENCY CARTRIDGE, AND METHOD OF USING SAME," published Jan. 3, 2019;

U.S. Patent Application Publication No. US 20160256156 (application Ser. No. 14/852,982, filed Sep. 14, 2015), titled "TIME DEPENDENT EVALUATION OF SENSOR DATA TO DETERMINE STABILITY, CREEP, AND VISCOELASTIC ELEMENTS OF MEASURES," published Sep. 8, 2016; and U.S. Pat. No. 10,695,081, titled "CONTROLLING A SURGICAL INSTRUMENT ACCORDING TO SENSED CLOSURE PARAMETERS," issued Jun. 30, 2020.

U.S. Patent Application Publication No. US 2019-0200844 A1 (U.S. patent application Ser. No. 16/209,385 filed Dec. 4, 2018), titled "METHOD OF HUB COMMUNICATION, PROCESSING, STORAGE AND DISPLAY," published Jul. 4, 2019;

U.S. Patent Application Publication No. US 2019-0201137 A1 (U.S. patent application Ser. No. 16/209,407, filed Dec. 4, 2018), titled "METHOD OF ROBOTIC HUB COMMUNICATION, DETECTION, AND CONTROL," published Jul. 4, 2019;

U.S. Patent Application Publication No. US 2019-0206569 A1 (U.S. patent application Ser. No. 16/209,403 filed Dec. 4, 2018), titled "METHOD OF CLOUD BASED DATA ANALYTICS FOR USE WITH THE HUB," published Jul. 4, 2019;

U.S. Patent Application Publication No. US 2017-0296213 A1 (U.S. patent application Ser. No. 15/130,590 filed Apr. 15, 2016), titled "SYSTEMS AND METHODS FOR CONTROLLING A SURGICAL STAPLING AND CUTTING INSTRUMENT," published Oct. 19, 2017;

U.S. Pat. No. 9,345,481, titled "STAPLE CARTRIDGE TISSUE THICKNESS SENSOR SYSTEM," issued May 24, 2016;

U.S. Patent Application Publication No. US 2014/0263552 (U.S. patent application Ser. No. 13/800,067 filed Mar. 13, 2013), titled "STAPLE CARTRIDGE TISSUE THICKNESS SENSOR SYSTEM," published Sep. 18, 2014; and U.S. Patent Application Publication No. US 2018/0360452 (U.S. patent application Ser. No. 15/628,175, filed Jun. 20, 2017), titled "TECHNIQUES FOR ADAPTIVE CONTROL OF MOTOR VELOCITY OF A SURGICAL STAPLING AND CUTTING INSTRUMENT," published Dec. 20, 2018.

Systems and techniques are disclosed for controlling the communication capabilities between a surgical instrument such as, for example, a surgical stapler and a removeable component such as, for example, staple cartridge. A surgical instrument may determine one or more parameters associated with the surgical instrument and the removable component. For example, the surgical instrument may determine a parameter representing a software version associated with one of the surgical instrument or component. The surgical instrument may determine the type and degree of communication that may take place between the surgical instrument and the removable component based on the one or more parameters. For example, the surgical stapler may determine two-way communication may be performed between the surgical instrument and the removable component based upon a parameter indicating the surgical instrument and/or removable instrument comprise a recent software version.

Referring to FIG. 1, a computer-implemented interactive surgical system 100 may include one or more surgical systems 102 and a cloud-based system (e.g., the cloud 104 that may include a remote server 113 coupled to a storage device 105). Each surgical system 102 may include at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
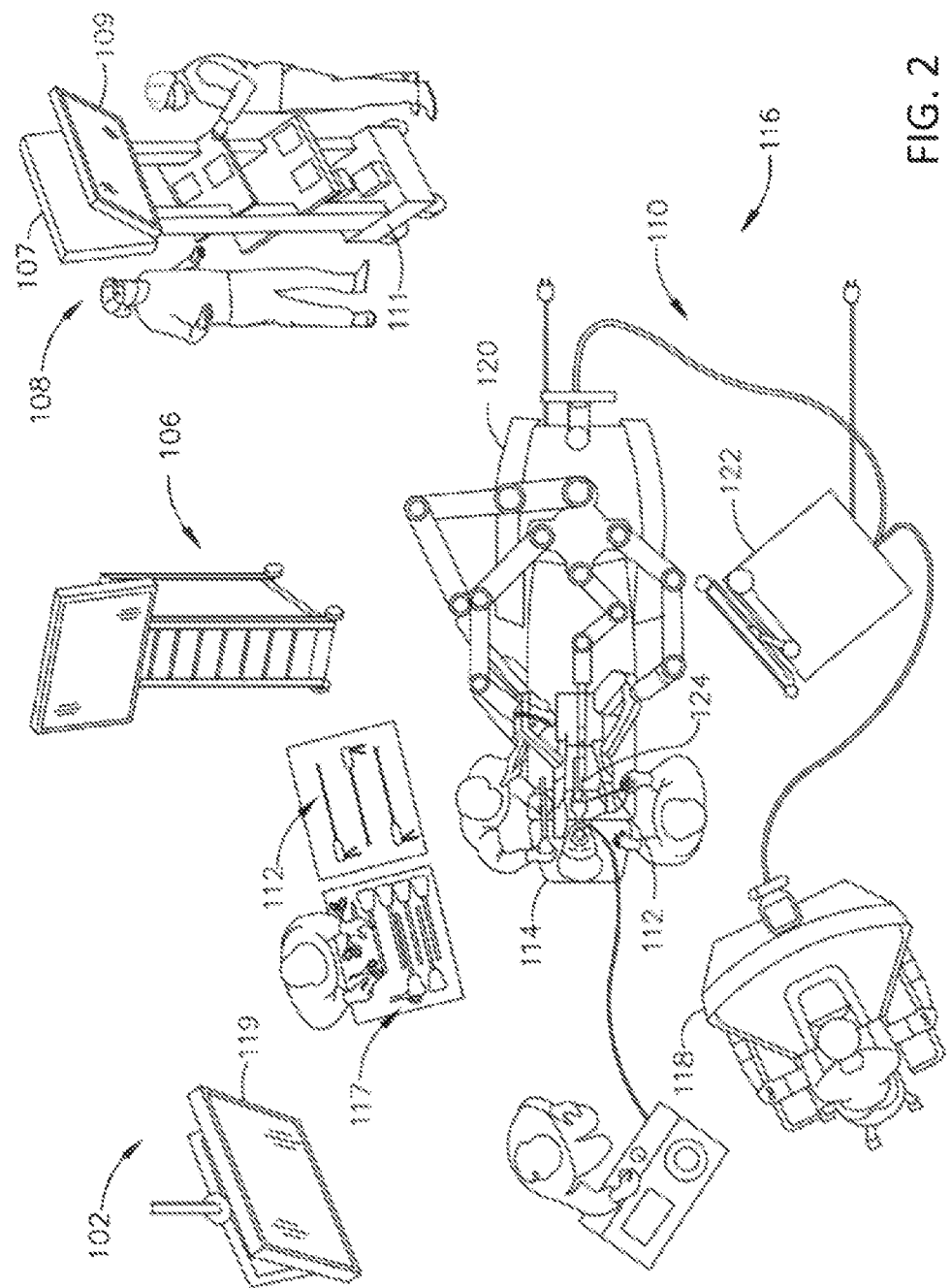
FIG. 2 shows an example surgical system being used to perform a surgical procedure in an operating room.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described under the heading "Advanced Imaging Acquisition Module" in US. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 may also be configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in .S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 3:
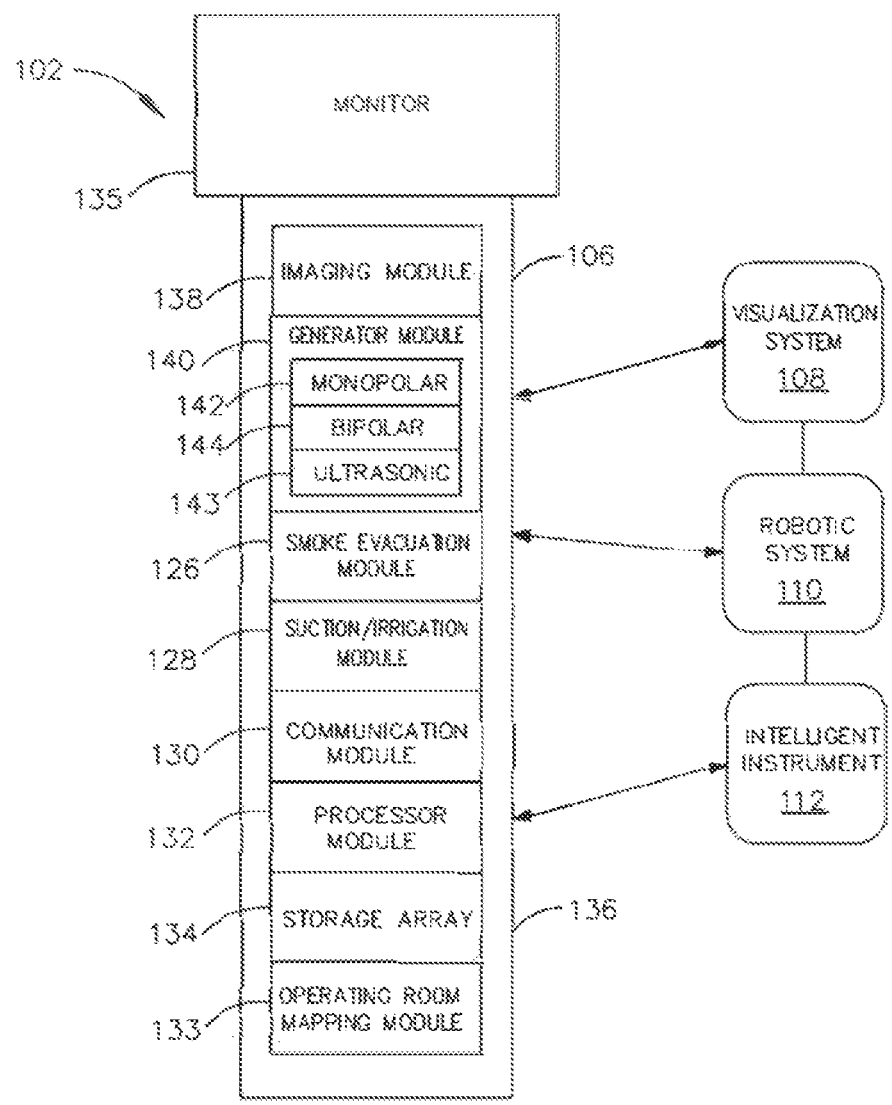
FIG. 3 shows an example surgical hub paired with a visualization system, a robotic system, and an intelligent instrument.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, a storage array 134, and an operating-room mapping module 133. In certain aspects, as illustrated in FIG. 3, the hub 106 further includes a smoke evacuation module 126 and/or a suction/irrigation module 128. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines. Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line is a first fluid line and a second fluid line extends from the remote surgical site to a suction and irrigation module slidably received in the hub enclosure. In one aspect, the hub enclosure comprises a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 146. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

Figure 4:
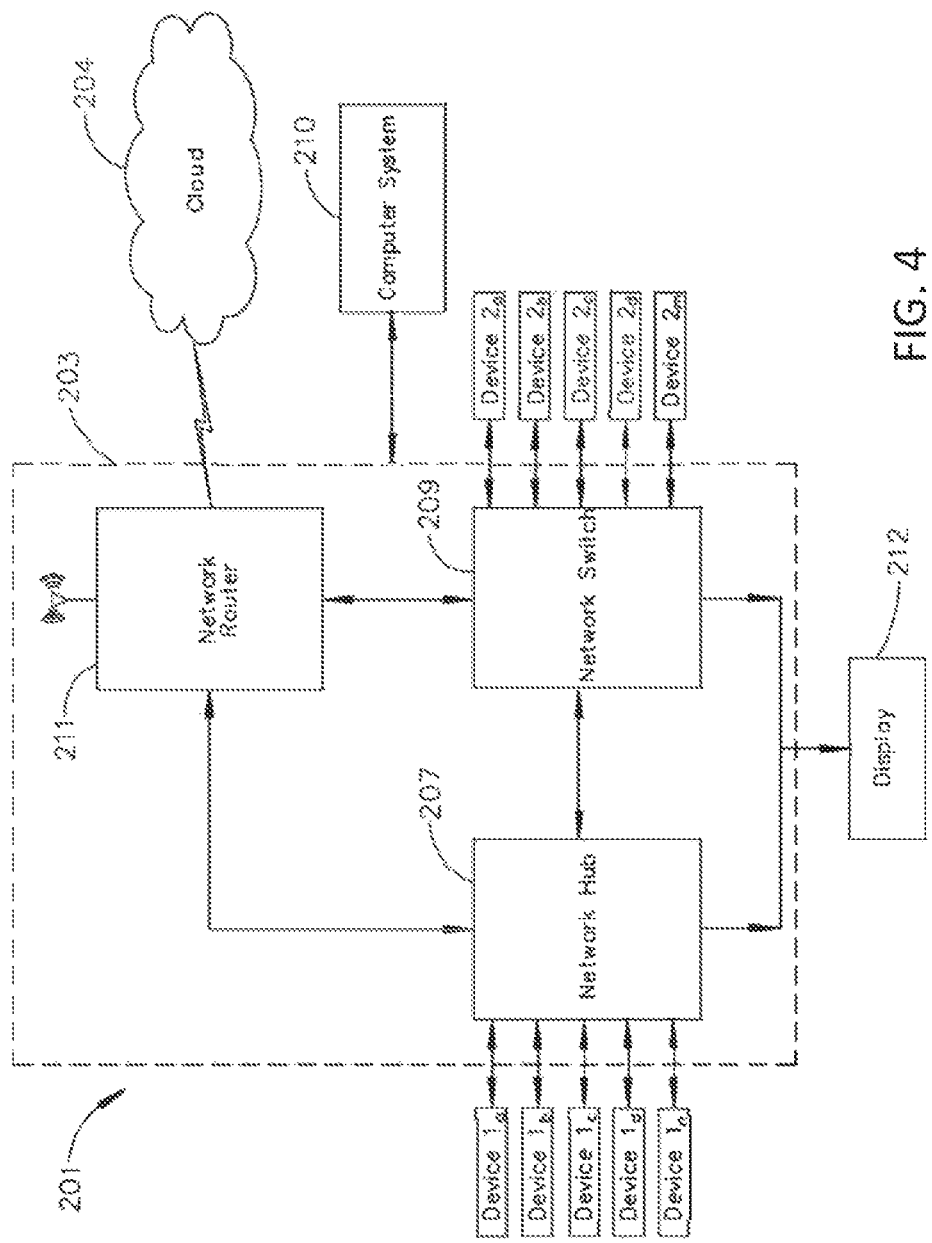
FIG. 4 illustrates a surgical data network having a communication hub configured to connect modular devices located in one or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2m may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

The operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub may provide connectivity to the devices 1a-1n located in the same operating theater network. The network hub 207 may collect data in the form of packets and sends them to the router in half duplex mode. The network hub 207 may not store any media access control/Internet Protocol (MAC/IP) to transfer the device data. Only one of the devices 1a-1n can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions, but having all information broadcast to multiple ports can be a security risk and cause bottlenecks.

The operating theater devices 2a-2m may be connected to a network switch 209 over a wired channel or a wireless channel. The network switch 209 works in the data link layer of the OSI model. The network switch 209 may be a multicast device for connecting the devices 2a-2m located in the same operating theater to the network. The network switch 209 may send data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
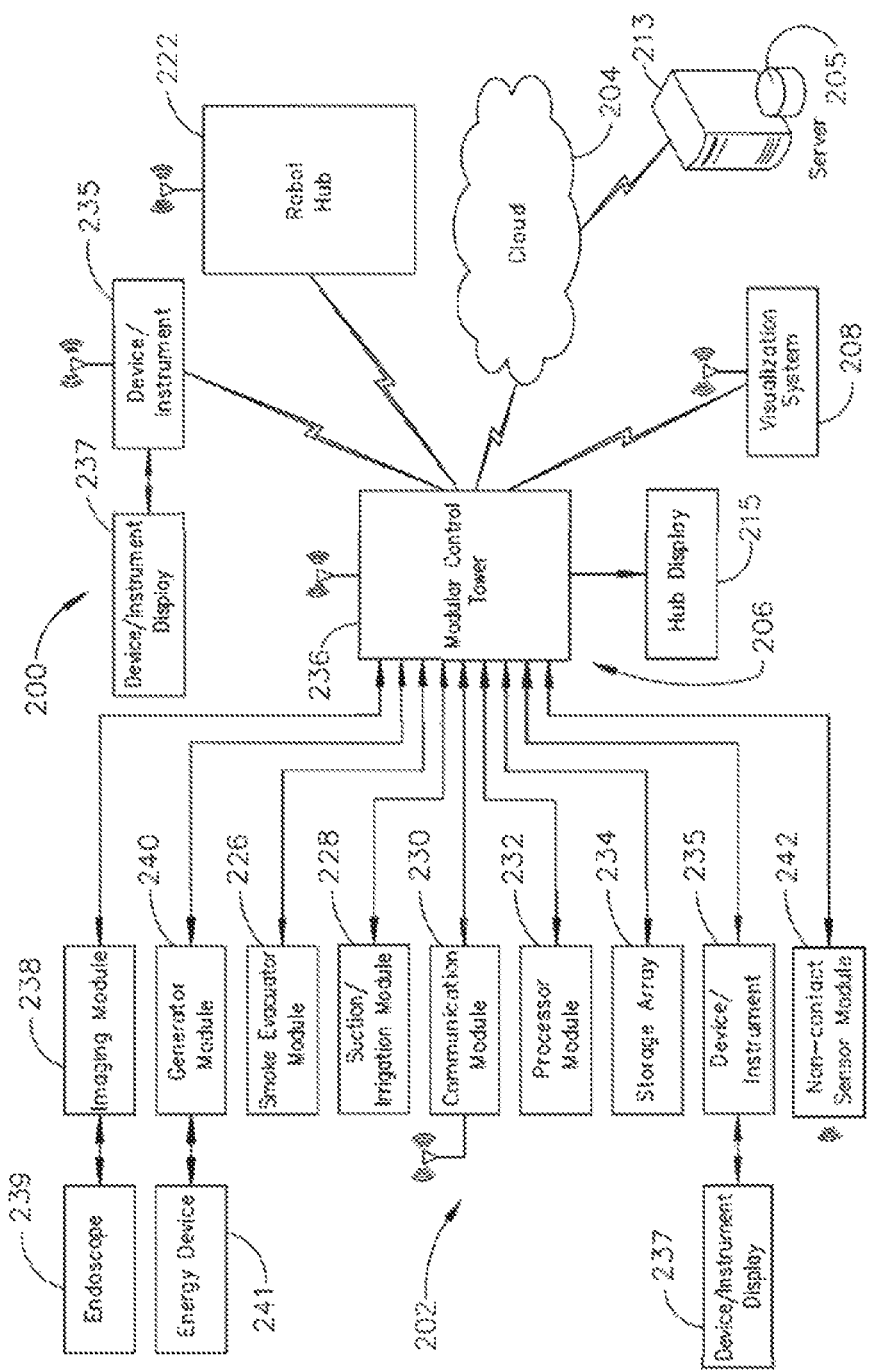
FIG. 5 illustrates an example computer-implemented interactive surgical system.
Figure 6:
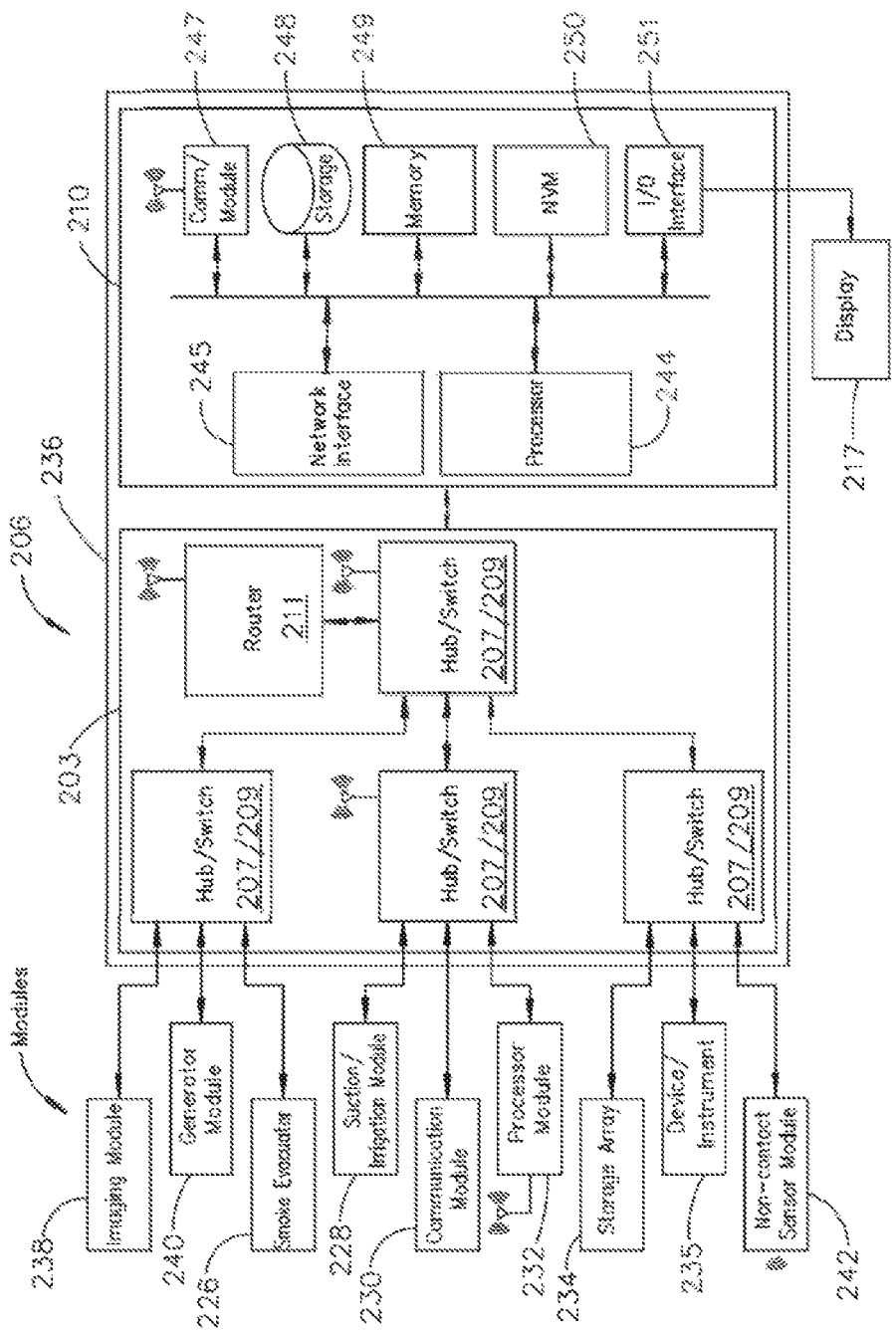
FIG. 6 illustrates an example surgical hub comprising a plurality of modules coupled to the modular control tower.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during startup, is stored in non-volatile memory. For example, the non-volatile memory can include ROM, programmable ROM (PROM), electrically programmable ROM (EPROM), EEPROM, or flash memory.

Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
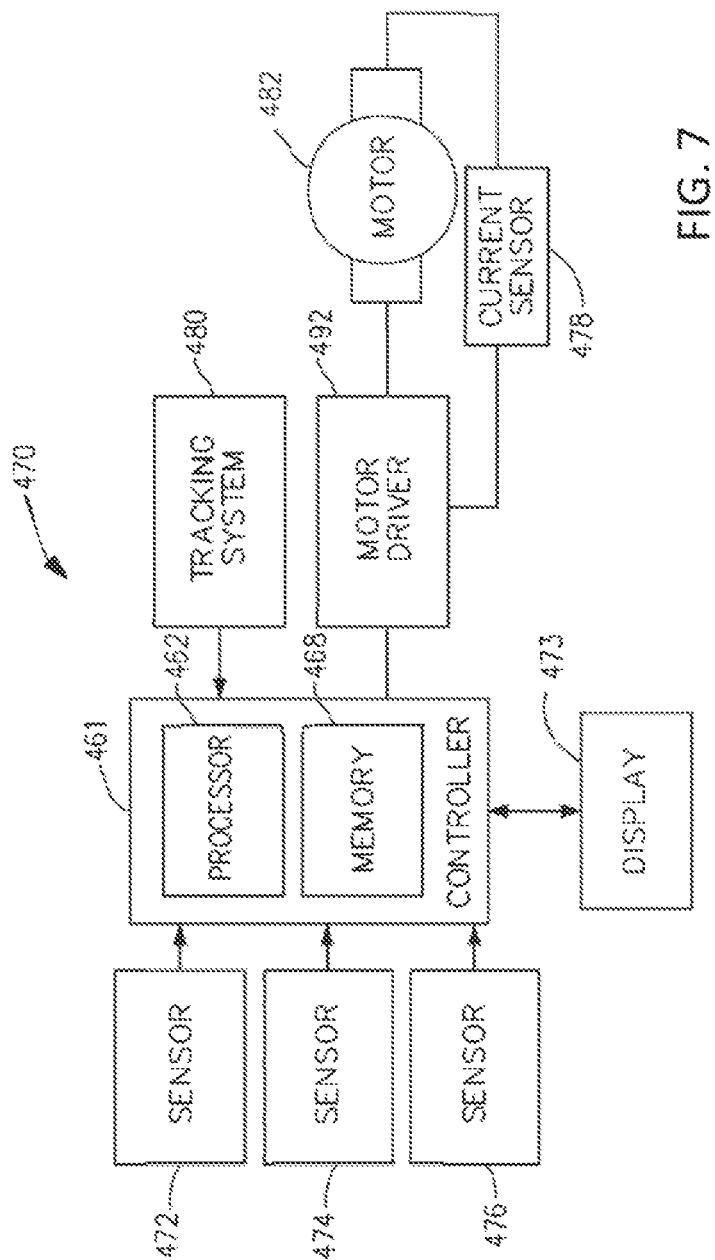
FIG. 7 illustrates an example surgical instrument or tool.

FIG. 7 illustrates a logic diagram of a control system 470 of a surgical instrument or tool in accordance with one or more aspects of the present disclosure. The system 470 may comprise a control circuit. The control circuit may include a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 may be configured to determine the position of the longitudinally movable displacement member. The position information may be provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 may display a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 may include a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In some examples, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 may be a full-bridge controller for use with external N-channel power metal-oxide semiconductor field-effect transistors (MOSFETs) specifically designed for inductive loads, such as brush DC motors. The driver 492 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the lowside FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 may comprise a controlled motor drive circuit arrangement comprising a position sensor 472 according to one aspect of this disclosure. The position sensor 472 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 472 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches may be fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiberoptic, magneto-optic, and microelectromechanical systems-based magnetic sensors, among others.

In one aspect, the position sensor 472 for the tracking system 480 comprising an absolute positioning system may comprise a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 may be a low-voltage and low-power component and includes four Hall-effect elements in an area of the position sensor 472 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bitshift, and table lookup operations. The angle position, alarm bits, and magnetic field information may be transmitted over a standard serial communication interface, such as a serial peripheral interface (SPI) interface, to the microcontroller 461. The position sensor 472 may provide 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertial, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force may be converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 474, such as, for example, a micro-strain gauge, that can be configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain can be converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub 203 as shown in FIGS. 5 and 6.

Figure 8:
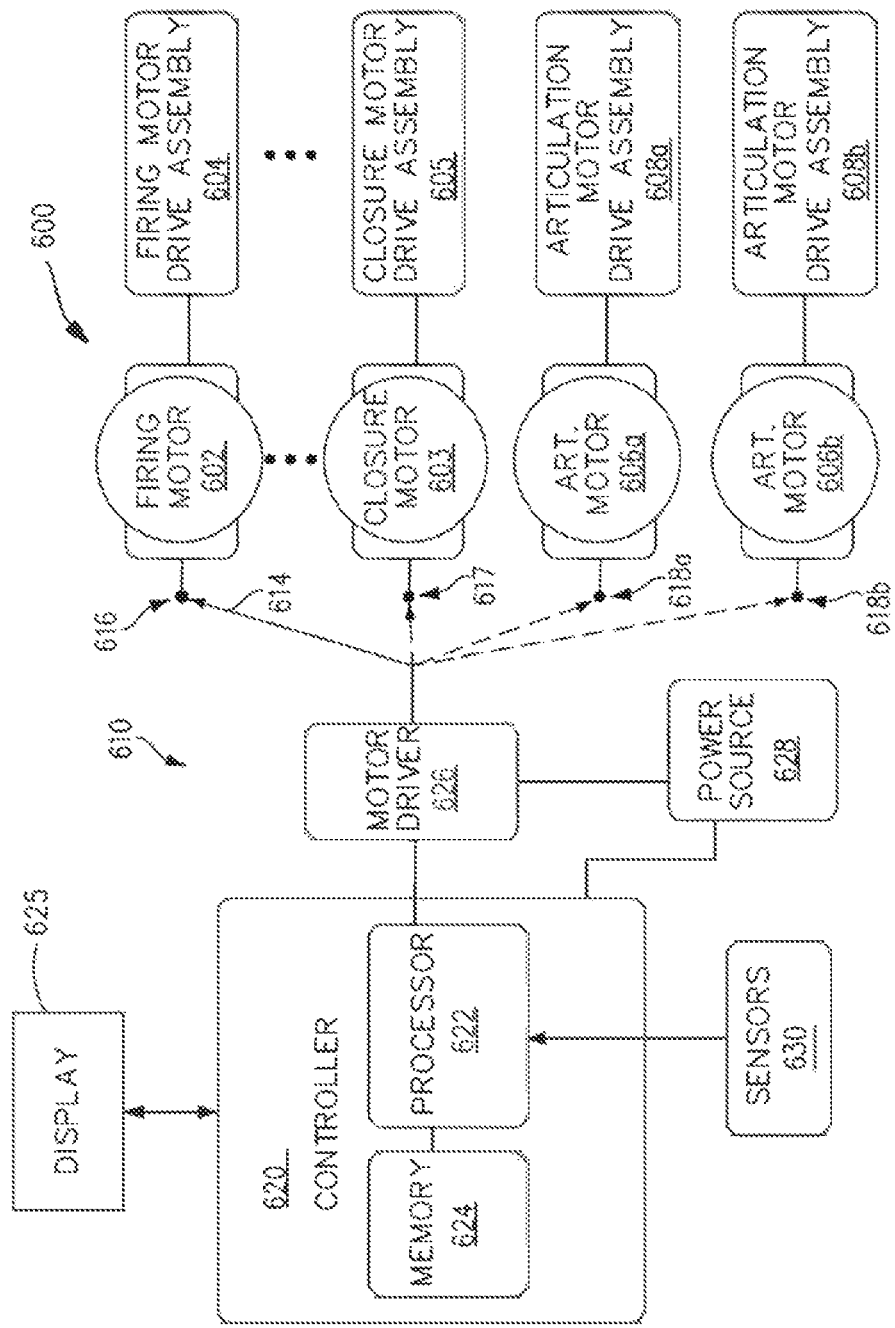
FIG. 8 illustrates an example surgical instrument or tool having motors that can be activated to perform various functions.

FIG. 8 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described herein, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 8, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 8, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described herein.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor can be a multipurpose, programmable device that accepts digital data as input, processes it according to instructions stored in its memory, and provides results as output. It can be an example of sequential digital logic, as it may have internal memory. Processors may operate on numbers and symbols represented in the binary numeral system.

The processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

The memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

One or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 9:
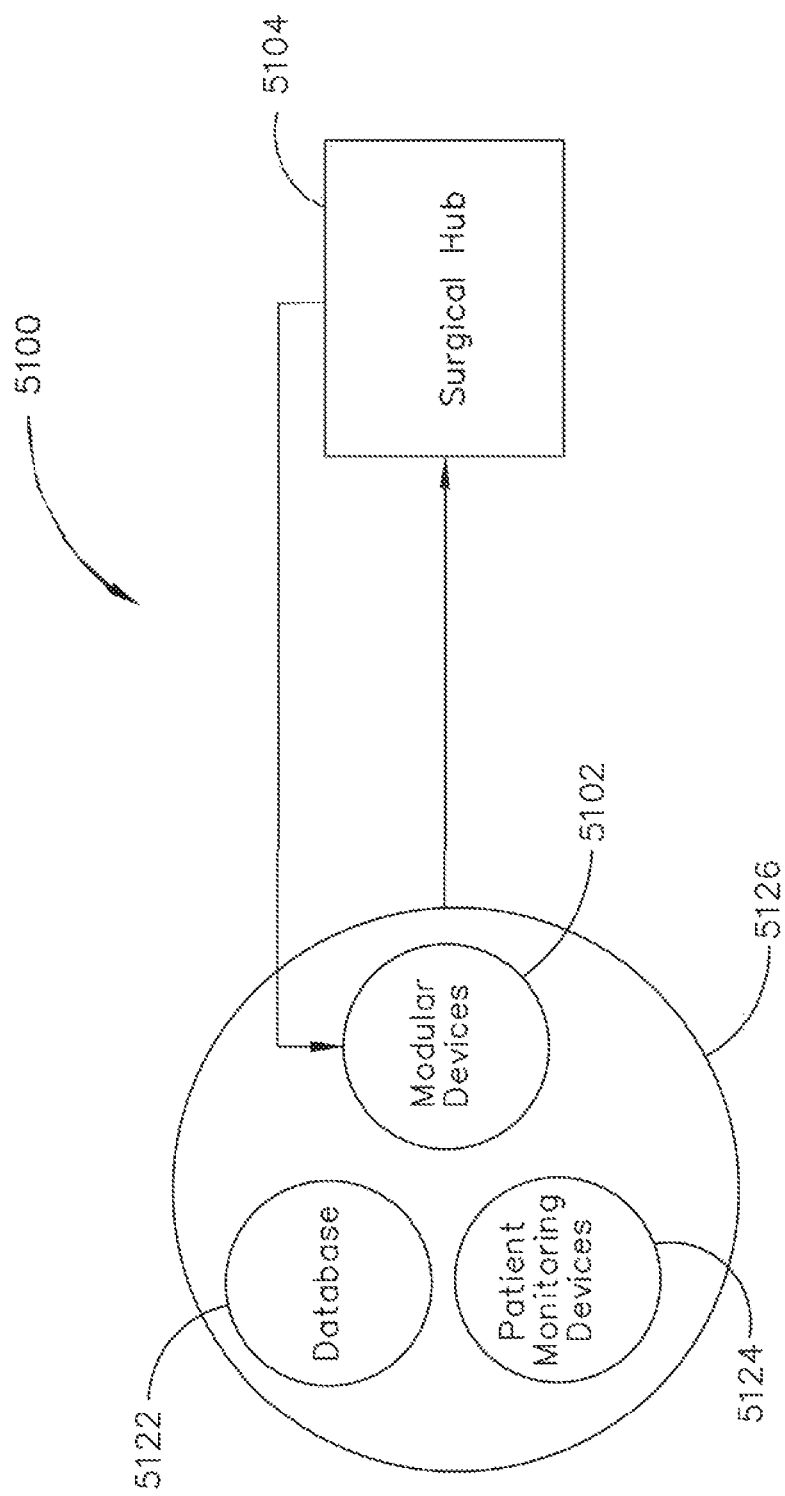
FIG. 9 is a diagram of an example situationally aware surgical system.

FIG. 9 illustrates a diagram of a situationally aware surgical system 5100, in accordance with at least one aspect of the present disclosure. In some exemplifications, the data sources 5126 may include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In an exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In an exemplification, the situational awareness system can include a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in an exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can be configured to compare the list of items for the procedure and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In some exemplifications, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In some exemplifications, the surgical hub 5104 can be configured to provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 10:
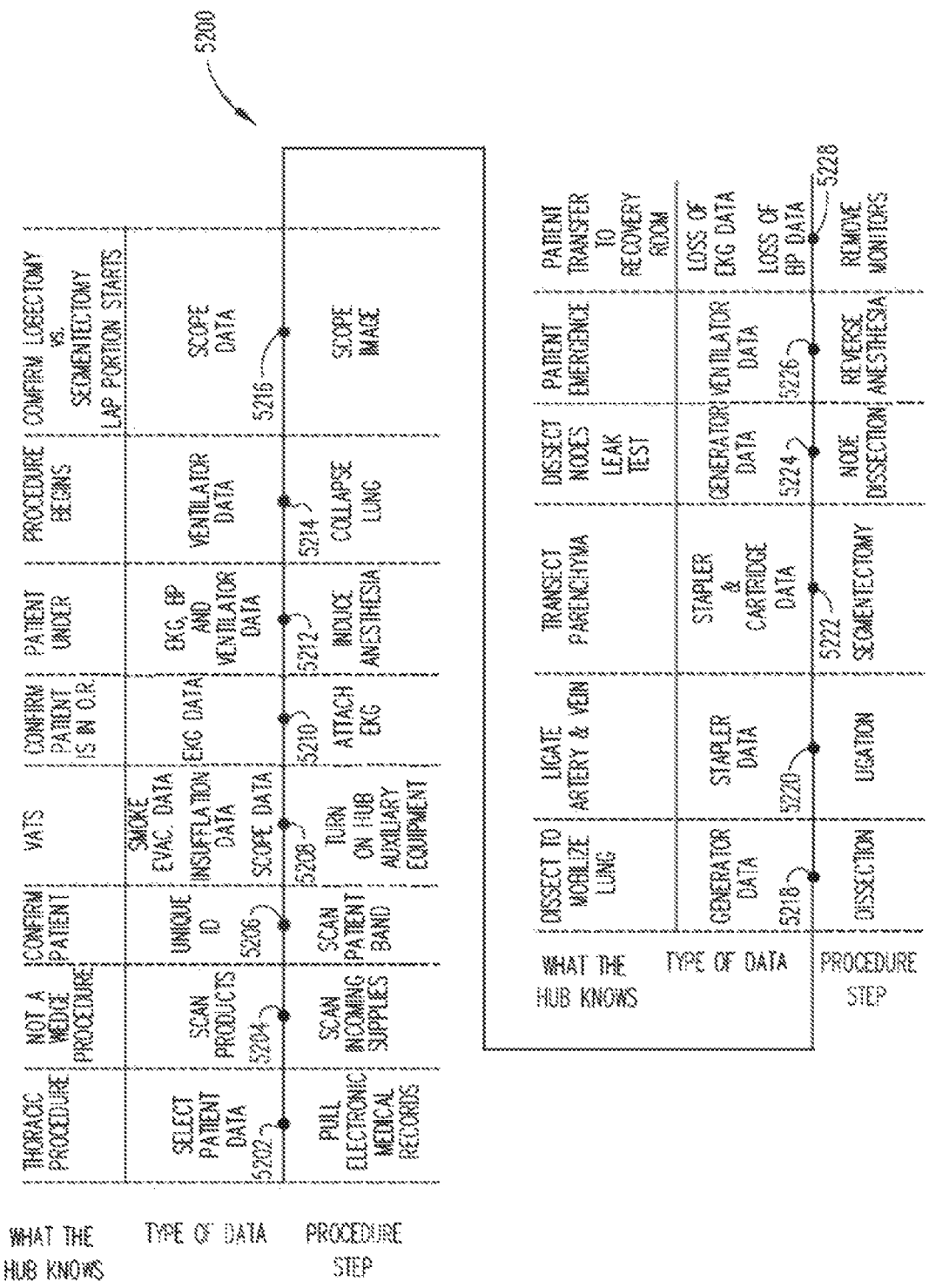
FIG. 10 illustrates an example timeline of an illustrative surgical procedure and the inferences that the surgical hub can make from the data detected at each step in the surgical procedure.

FIG. 10 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 9, reference should also be made to FIG. 9. The timeline 5200 may depict the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 may receive data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 can be able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described herein.

As the first step 5202 in this illustrative procedure, the hospital staff members may retrieve the patient's EMR from the hospital's EMR database. Based on select patient data in the EMR, the surgical hub 5104 determines that the procedure to be performed is a thoracic procedure. Second 5204, the staff members may scan the incoming medical supplies for the procedure. The surgical hub 5104 cross-references the scanned supplies with a list of supplies that can be utilized in various types of procedures and confirms that the mix of supplies corresponds to a thoracic procedure. Further, the surgical hub 5104 may also be able to determine that the procedure is not a wedge procedure (because the incoming supplies either lack certain supplies that are necessary for a thoracic wedge procedure or do not otherwise correspond to a thoracic wedge procedure). Third 5206, the medical personnel may scan the patient band via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that may be located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 may determine that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 may pair with the surgical hub 5104. As the surgical hub 5104 begins receiving data from the patient monitoring devices 5124, the surgical hub 5104 may confirm that the patient is in the operating theater, as described in the process 5207, for example. Sixth 5212, the medical personnel may induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof. for example. Upon completion of the sixth step 5212, the pre-operative portion of the lung segmentectomy procedure is completed and the operative portion begins.

Seventh 5214, the patient's lung that is being operated on may be collapsed (while ventilation is switched to the contralateral lung). The surgical hub 5104 can infer from the ventilator data that the patient's lung has been collapsed, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung can be the first operative step in this particular procedure. Eighth 5216, the medical imaging device 5108 (e.g., a scope) may be inserted and video from the medical imaging device may be initiated. The surgical hub 5104 may receive the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy may place the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. An example technique for performing a VATS lobectomy may utilize a single medical imaging device. An example technique for performing a VATS segmentectomy utilizes multiple cameras. An example technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team may begin the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team may proceed to the ligation step of the procedure. The surgical hub 5104 can infer that the surgeon is ligating arteries and veins because it may receive data from the surgical stapling and cutting instrument indicating that the instrument is being fired. Similar to the prior step, the surgical hub 5104 can derive this inference by cross-referencing the receipt of data from the surgical stapling and cutting instrument with the retrieved steps in the process. Eleventh 5222, the segmentectomy portion of the procedure can be performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (e.g., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure may begin.

Thirteenth 5226, the patient's anesthesia can be reversed. The surgical hub 5104 can infer that the patient is emerging from the anesthesia based on the ventilator data (i.e., the patient's breathing rate begins increasing), for example. Lastly, the fourteenth step 5228 may be that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 10, the patient data can also be utilized by a situationally aware surgical hub 5104 to generate control adjustments for the paired modular devices 5102.

Figure 11:
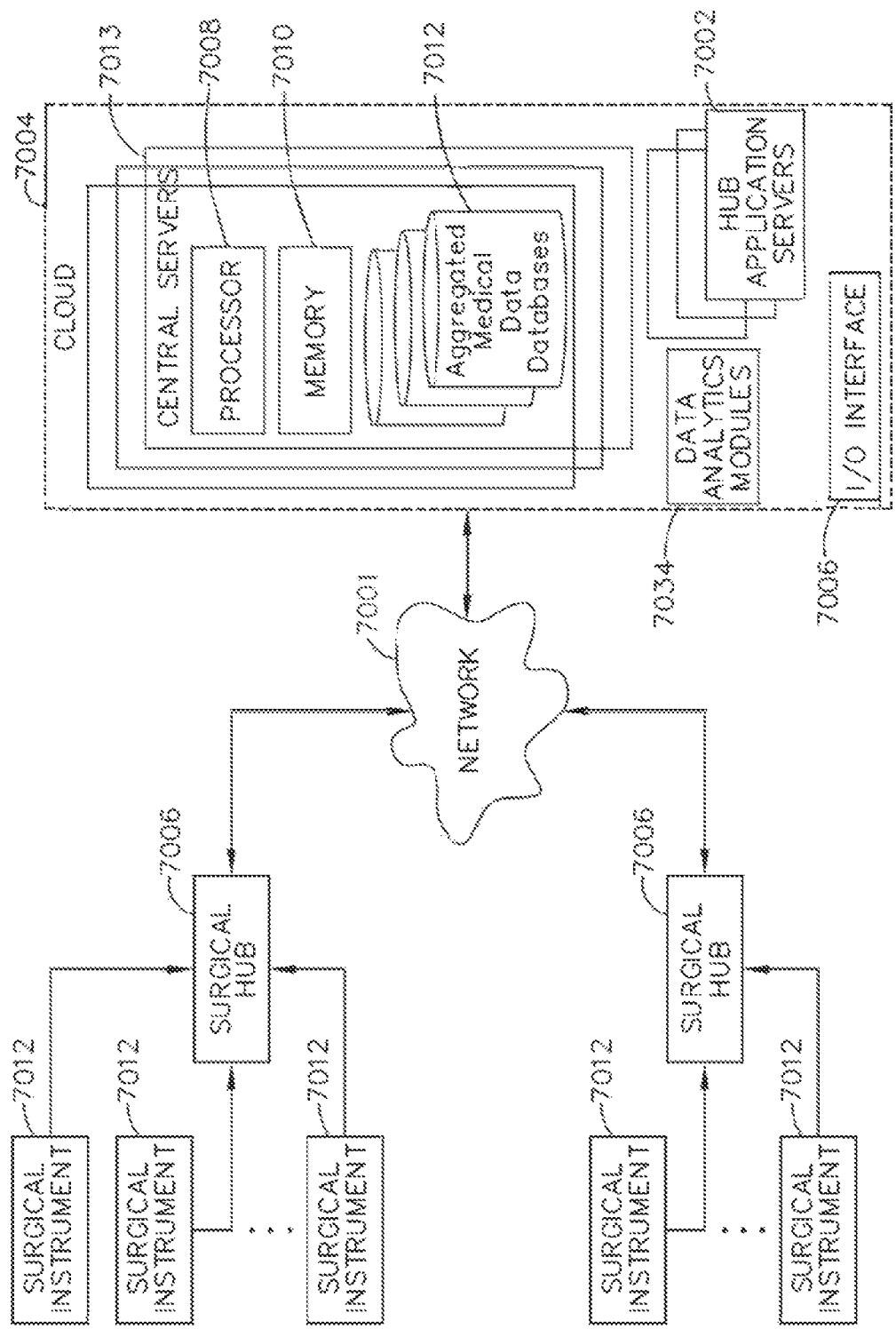
FIG. 11 is a block diagram of the computer-implemented interactive surgical system.

FIG. 11 is a block diagram of the computer-implemented interactive surgical system, in accordance with at least one aspect of the present disclosure. In one aspect, the computer-implemented interactive surgical system may be configured to monitor and analyze data related to the operation of various surgical systems that include surgical hubs, surgical instruments, robotic devices and operating theaters or healthcare facilities. The computer-implemented interactive surgical system may comprise a cloud-based analytics system. Although the cloud-based analytics system may be described as a surgical system, it may not be necessarily limited as such and could be a cloud-based medical system generally. As illustrated in FIG. 11, the cloud-based analytics system may comprise a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 may be communicatively coupled to one or more surgical instruments 7012. The hubs 7006 may also be communicatively coupled to the cloud 7004 of the computer-implemented interactive surgical system via the network 7001. The cloud 7004 may be a remote centralized source of hardware and software for storing, manipulating, and communicating data generated based on the operation of various surgical systems. As shown in FIG. 11, access to the cloud 7004 may be achieved via the network 7001, which may be the Internet or some other suitable computer network. Surgical hubs 7006 that may be coupled to the cloud 7004 can be considered the client side of the cloud computing system (i.e., cloud-based analytics system). Surgical instruments 7012 may be paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 11, the cloud 7004 comprises central servers 7013 (may be same or similar to remote server 7013), hub application servers 7002, data analytics modules 7034, and an input/output ("I/O") interface 7006. The central servers 7013 of the cloud 7004 collectively administer the cloud computing system, which includes monitoring requests by client surgical hubs 7006 and managing the processing capacity of the cloud 7004 for executing the requests. Each of the central servers 7013 may comprise one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also may comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7012 of the cloud 7004. In particular, the cloud 7004 may advantageously perform data analysis and operations on the aggregated data to yield insights and/or perform functions that individual hubs 7006 could not achieve on their own. To this end, as shown in FIG. 11, the cloud 7004 and the surgical hubs 7006 are communicatively coupled to transmit and receive information. The I/O interface 7006 is connected to the plurality of surgical hubs 7006 via the network 7001. In this way, the I/O interface 7006 can be configured to transfer information between the surgical hubs 7006 and the aggregated medical data databases 7011. Accordingly, the I/O interface 7006 may facilitate read/write operations of the cloud-based analytics system. Such read/write operations may be executed in response to requests from hubs 7006. These requests could be transmitted to the hubs 7006 through the hub applications. The I/O interface 7006 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 may be configured to host and supply shared capabilities to software applications (e.g., hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 12.

The particular cloud computing system configuration described in the present disclosure may be specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch-controlled user interfaces such that clinicians may control aspects of interaction between the surgical instruments 7012 and the cloud 7004. Other suitable user interfaces for control such as auditory controlled user interfaces can also be used.

Figure 12:
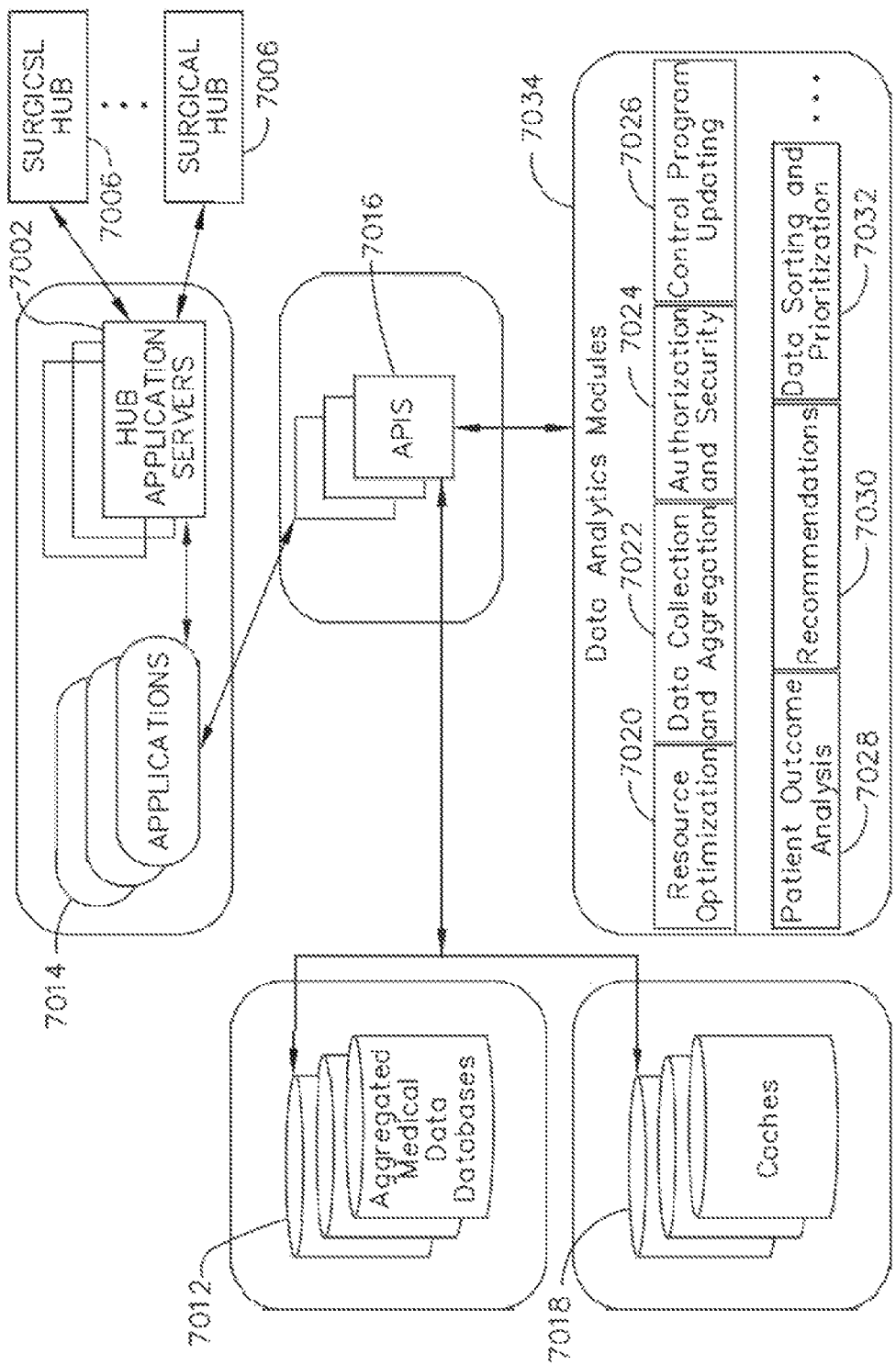
FIG. 12 illustrates the functional architecture of an example computer-implemented interactive surgical system.

FIG. 12 is a block diagram which illustrates the functional architecture of the computer-implemented interactive surgical system, in accordance with at least one aspect of the present disclosure. The cloud-based analytics system may include a plurality of data analytics modules 7034 that may be executed by the processors 7008 of the cloud 7004 for providing data analytic solutions to problems specifically arising in the medical field. As shown in FIG. 12, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 may define the set of protocols and routines corresponding to the hub applications 7014. Additionally, the APIs 7016 may manage the storing and retrieval of data into and from the aggregated medical databases 7012 for the operations of the applications 7014. The caches 7018 may also store data (e.g., temporarily) and may be coupled to the APIs 7016 for more efficient retrieval of data used by the applications 7014. The data analytics modules 7034 in FIG. 12 may include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules may be used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently. The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that may be transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004. Furthermore, for security purposes, the cloud could maintain a database of hubs 7006, instruments 7012, and other devices that may comprise a "black list" of prohibited devices. In particular, a surgical hubs 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally, or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash-based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described herein to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g., a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional example details for the various functions described are provided in the ensuing descriptions below. Each of the various descriptions may utilize the cloud architecture as described in FIGS. 11 and 12 as one example of hardware and software implementation.

Figure 13:
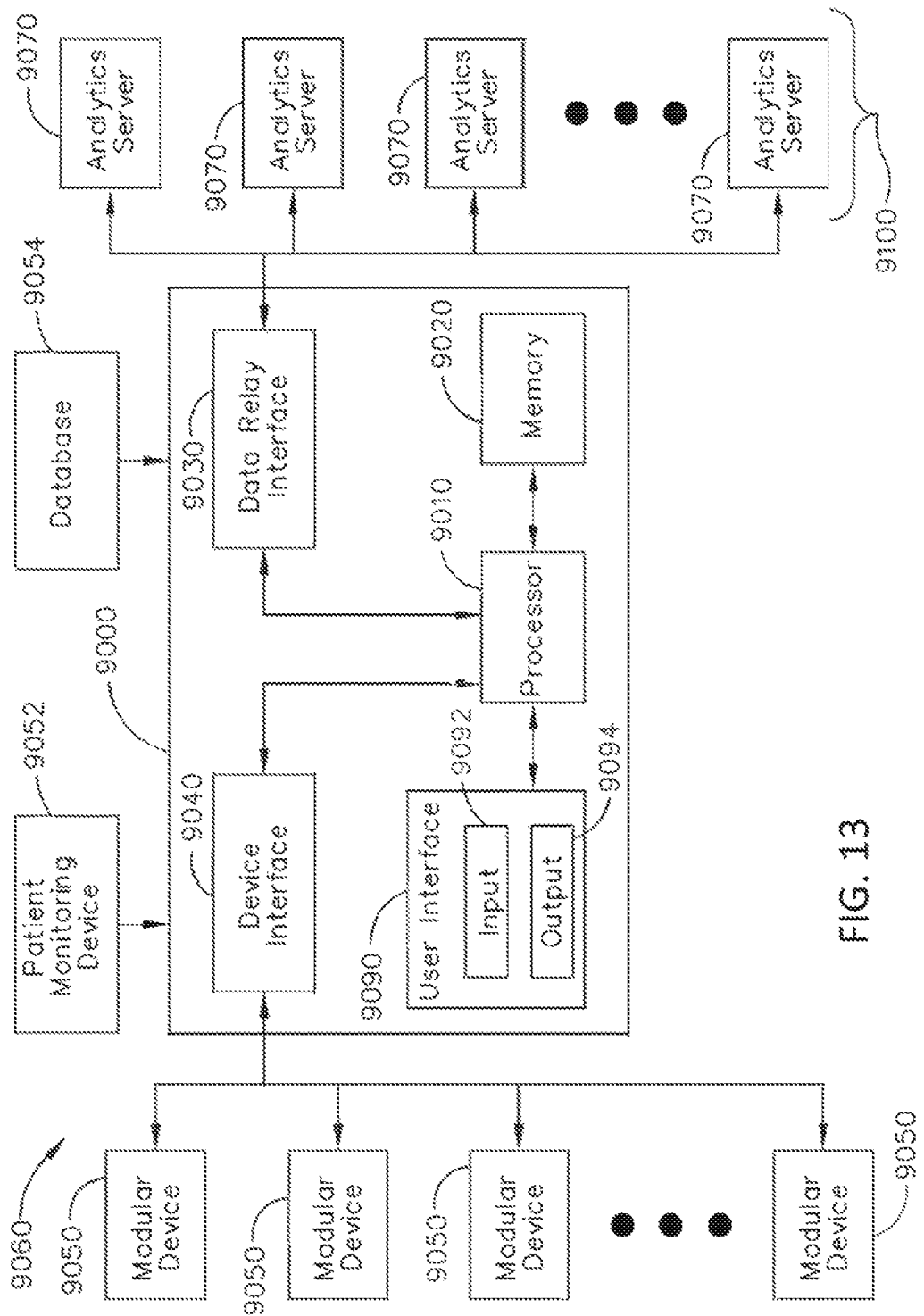
FIG. 13 illustrates an example computer-implemented interactive surgical system that is configured to adaptively generate control program updates for modular devices.

FIG. 13 illustrates a block diagram of a computer-implemented adaptive surgical system 9060 that is configured to adaptively generate control program updates for modular devices 9050, in accordance with at least one aspect of the present disclosure. In some exemplifications, the surgical system may include a surgical hub 9000, multiple modular devices 9050 communicably coupled to the surgical hub 9000, and an analytics system 9100 communicably coupled to the surgical hub 9000. Although a single surgical hub 9000 may be depicted, it should be noted that the surgical system 9060 can include any number of surgical hubs 9000, which can be connected to form a network of surgical hubs 9000 that are communicably coupled to the analytics system 9010. In some exemplifications, the surgical hub 9000 may include a processor 9010 coupled to a memory 9020 for executing instructions stored thereon and a data relay interface 9030 through which data is transmitted to the analytics system 9100. In some exemplifications, the surgical hub 9000 further may include a user interface 9090 having an input device 9092 (e.g., a capacitive touchscreen or a keyboard) for receiving inputs from a user and an output device 9094 (e.g., a display screen) for providing outputs to a user. Outputs can include data from a query input by the user, suggestions for products or mixes of products to use in a given procedure, and/or instructions for actions to be carried out before, during, or after surgical procedures. The surgical hub 9000 further may include an interface 9040 for communicably coupling the modular devices 9050 to the surgical hub 9000. In one aspect, the interface 9040 may include a transceiver that is communicably connectable to the modular device 9050 via a wireless communication protocol. The modular devices 9050 can include, for example, surgical stapling and cutting instruments, electrosurgical instruments, ultrasonic instruments, insufflators, respirators, and display screens. In some exemplifications, the surgical hub 9000 can further be communicably coupled to one or more patient monitoring devices 9052, such as EKG monitors or BP monitors. In some exemplifications, the surgical hub 9000 can further be communicably coupled to one or more databases 9054 or external computer systems, such as an EMR database of the medical facility at which the surgical hub 9000 is located.

When the modular devices 9050 are connected to the surgical hub 9000, the surgical hub 9000 can sense or receive perioperative data from the modular devices 9050 and then associate the received perioperative data with surgical procedural outcome data. The perioperative data may indicate how the modular devices 9050 were controlled during the course of a surgical procedure. The procedural outcome data includes data associated with a result from the surgical procedure (or a step thereof), which can include whether the surgical procedure (or a step thereof) had a positive or negative outcome. For example, the outcome data could include whether a patient suffered from postoperative complications from a particular procedure or whether there was leakage (e.g., bleeding or air leakage) at a particular staple or incision line. The surgical hub 9000 can obtain the surgical procedural outcome data by receiving the data from an external source (e.g., from an EMR database 9054), by directly detecting the outcome (e.g., via one of the connected modular devices 9050), or inferring the occurrence of the outcomes through a situational awareness system. For example, data regarding postoperative complications could be retrieved from an EMR database 9054 and data regarding staple or incision line leakages could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. In some exemplifications, the analytics system 9100 may include a network of analytics servers 9070 that are configured to receive data from the surgical hubs 9000. Each of the analytics servers 9070 can include a memory and a processor coupled to the memory that is executing instructions stored thereon to analyze the received data. In some exemplifications, the analytics servers 9070 may be connected in a distributed computing architecture and/or utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to the modular devices' 9050 control programs.

Additional detail regarding the computer-implemented interactive surgical system 9060, including the surgical hub 9000 and various modular devices 9050 connectable thereto, are described in connection with FIGS. 5-6.

Figure 14:
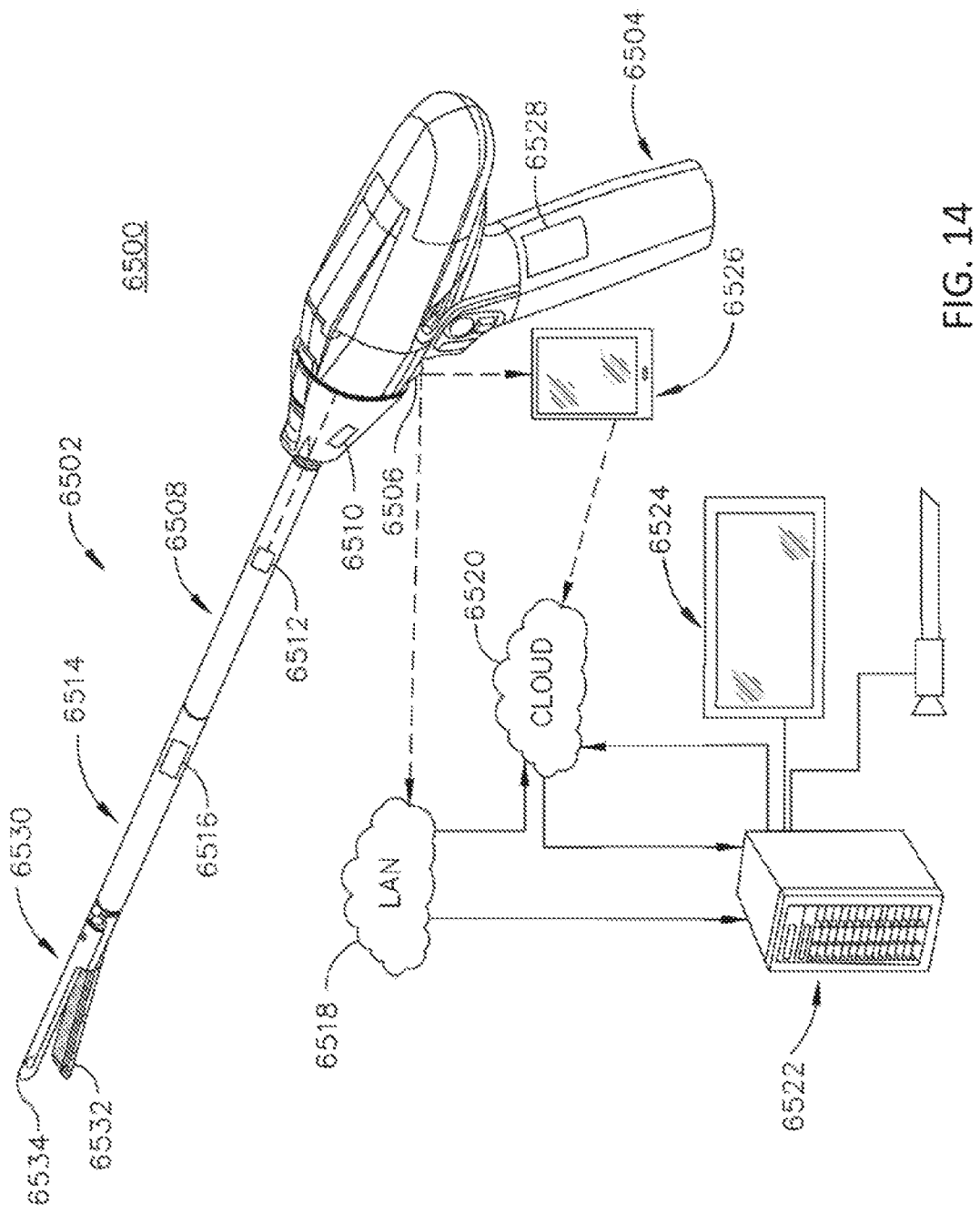
FIG. 14 illustrates an example surgical system that includes a handle having a controller and a motor, an adapter releasably coupled to the handle, and a loading unit releasably coupled to the adapter.

FIG. 14 provides a surgical system 6500 in accordance with the present disclosure and may include a surgical instrument 6502 that can be in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 may include a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 may include an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 may be configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more than one time prior to being replaced. The second jaw 6534 may include an anvil that deforms or otherwise secures the fasteners about tissue as the fasteners are ejected from the multi-fire fastener cartridge.

The handle 6504 may include a motor that is coupled to the drive shaft to affect rotation of the drive shaft. The handle 6504 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 may be in communication with a controller 6528 of the handle 6504 to selectively activate the motor to affect rotation of the drive shafts. The controller 6528 may be disposed within the handle 6504 and is configured to receive input from the control interface and adapter data from the adapter 6508 or loading unit data from the loading unit 6514. The controller 6528 may analyze the input from the control interface and the data received from the adapter 6508 and/or loading unit 6514 to selectively activate the motor. The handle 6504 may also include a display that is viewable by a clinician during use of the handle 6504. The display may be configured to display portions of the adapter or loading unit data before, during, or after firing of the instrument 6502.

The adapter 6508 may include an adapter identification device 6510 disposed therein and the loading unit 6514 includes a loading unit identification device 6516 disposed therein. The adapter identification device 6510 may be in communication with the controller 6528, and the loading unit identification device 6516 may be in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 may provide an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 can be configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 may include a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508) attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6528. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

Figure 15:
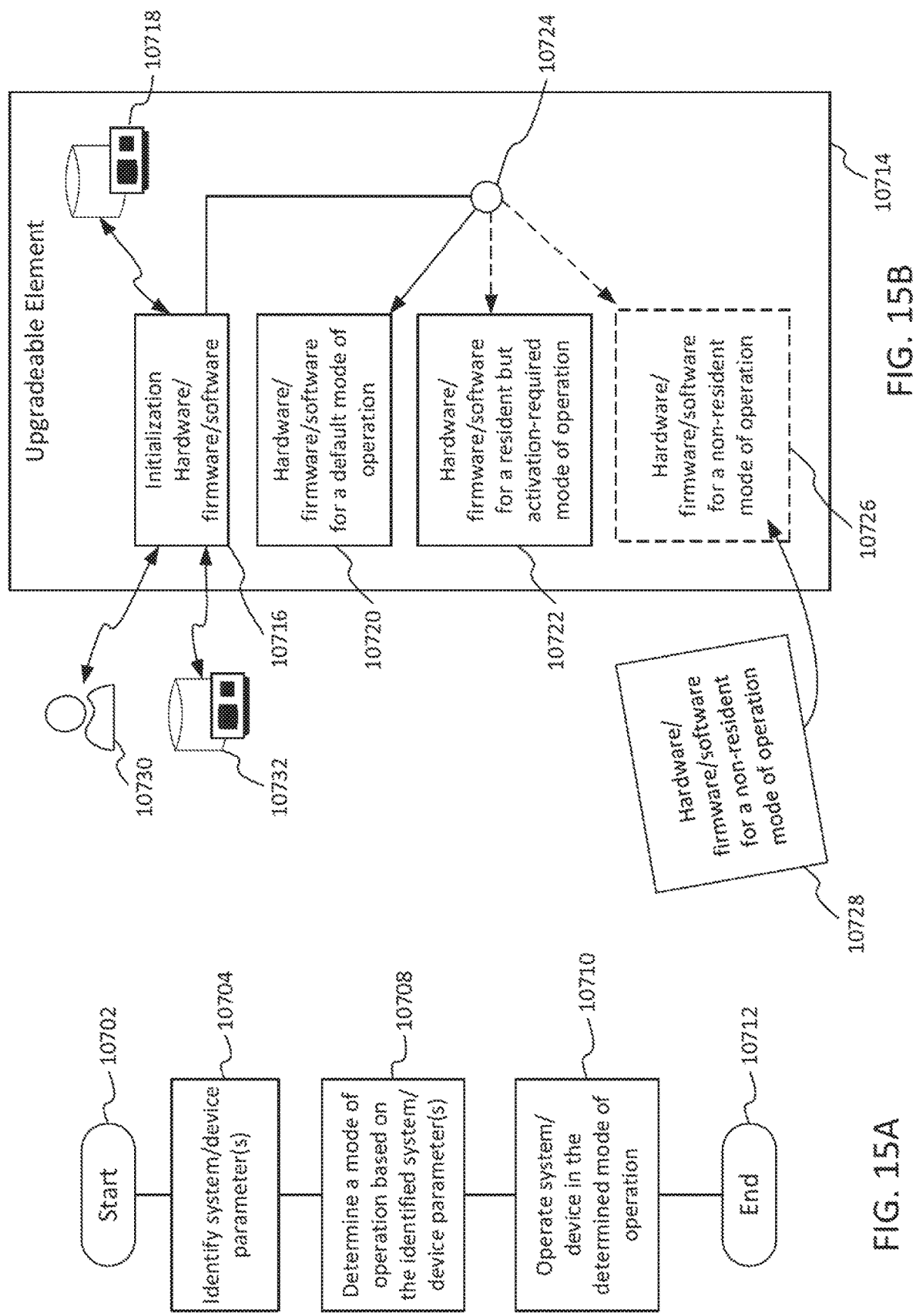
FIG. 15A illustrates an example flow for determining a mode of operation and operating in the determined mode.
FIG. 15B illustrates an example flow for changing a mode of operation.

FIG. 15A illustrates an example flow for determining a mode of operation and operating in the determined mode. The computer-implemented interactive surgical system and/ or components and/or subsystems of the computer-implemented interactive surgical system may be configured to be updated. Such updates may include the inclusions of features and benefits that were not available to the user before the update. These updates may be established by any method of hardware, firmware, and software updates suitable for introducing the feature to the user. For example, replaceable/ swappable (e.g., hot swappable) hardware components, flashable firmware devices, and updatable software systems may be used to update computer-implemented interactive surgical system and/or components and/or subsystems of the computer-implemented interactive surgical system.

The updates may be conditioned on any suitable criterion or set of criteria. For example, an update may be conditioned on one or more hardware capabilities of the system, such as processing capability, bandwidth, resolution, and the like. For example, the update may be conditioned on one or more software aspects, such as a purchase of certain software code. For example, the update may be conditioned on a purchased service tier. The service tier may represent a feature and/or a set of features the user is entitled to use in connection with the computer-implemented interactive surgical system. The service tier may be determined by a license code, an e-commerce server authentication interaction, a hardware key, a username/password combination, a biometric authentication interaction, a public/private key exchange interaction, or the like.

At 10704, a system/device parameter may be identified. The system/device parameter may be any element or set of elements on which an update in conditioned. For example, the computer-implemented interactive surgical system may detect a certain bandwidth of communication between a modular device and a surgical hub. For example, the computer-implemented interactive surgical system may detect an indication of the purchase of certain service tier.

At 10708, a mode of operation may be determined based on the identified system/device parameter. This determination may be made by a process that maps system/device parameters to modes of operation. The process may be a manual and/or an automated process. The process may be the result of local computation and/or remote computation. For example, a client/server interaction may be used to determine the mode of operation based on the on the identified system/device parameter. For example, local software and/or locally embedded firmware may be used to determine the mode of operation based on the identified system/device parameter. For example, a hardware key, such as a secure microprocessor for example, may be used to determine the mode of operation based on the identified system/device parameter.

At 10710, operation may proceed in accordance with the determined mode of operation. For example, a system or device may proceed to operate in a default mode of operation. For example, a system or device may proceed to operate in an alternate mode of operation. The mode of operation may be directed by control hardware, firmware, and/or software already resident in the system or device. The mode of operation may be directed by control hardware, firmware, and/or software newly installed/updated.

FIG. 15B illustrates an example functional block diagram for changing a mode of operation. An upgradeable element 10714 may include an initialization component 10716. The initialization component 10716 may include any hardware, firmware, and/or software suitable determining a mode of operation. For example, the initialization component 10716 may be portion of a system or device start-up procedure. The initialization component 10716 may engage in an interaction to determine a mode of operation for the upgradeable element 10714. For example, the initialization component 10716 may interact with a user 10730, an external resource 10732, and/or a local resource 10718 for example. For example, the initialization component 10716 may receive a licensing key from the user 10730 to determine a mode of operation. The initialization component 10716 may query an external resource 10732, such as a server for example, with a serial number of the upgradable device 10714 to determine a mode of operation. For example, the initialization component 10716 may query a local resource 10718, such as a local query to determine an amount of available bandwidth and/or a local query of a hardware key for example, to determine a mode of operation.

The upgradeable element 10714 may include one or more operation components 10720, 10722, 10726, 10728 and an operational pointer 10724. The initialization component 10716 may direct the operational pointer 10724 to direct the operation of the upgradable element 10741 to the operation component 10720, 10722, 10726, 10728 that corresponds with the determined mode of operation. The initialization component 10716 may direct the operational pointer 10724 to direct the operation of the upgradable element to a default operation component 10720. For example, the default operation component 10720 may be selected on the condition of no other alternate mode of operation being determined. For example, the default operation component 10720 may be selected on the condition of a failure of the initialization component and/or interaction failure. The initialization component 10716 may direct the operational pointer 10724 to direct the operation of the upgradable element 10714 to a resident operation component 10722. For example, certain features may be resident in the upgradable component 10714 but require activation to be put into operation. The initialization component 10716 may direct the operational pointer 10724 to direct the operation of the upgradable element 10714 to install a new operation component 10728 and/or a new installed operation component 10726. For example, new software and/or firmware may be downloaded. The new software and or firmware may contain code to enable the features represented by the selected mode of operation. For example, a new hardware component may be installed to enable the selected mode of operation.

FIGS. 16 to 19 depict a motor-driven surgical instrument 150010 for cutting and fastening that may or may not be reused. Additional information regarding a motor-driven surgical instrument 150010 may be found in U.S. Patent Publication No. 20190200981 (from U.S. application Ser. No. 16/209,423, filed Dec. 4, 2018), titled "METHOD OF COMPRESSING TISSUE WITHIN A STAPLING DEVICE AND SIMULTANEOUSLY DISPLAYING THE LOCATION OF THE TISSUE WITHIN THE JAWS," published Jul. 4, 2019, the contents of which are hereby incorporated herein in their entirety. In the illustrated examples, the surgical instrument 150010 includes a housing 150012 that comprises a handle assembly 150014 that is configured to be grasped, manipulated, and actuated by the clinician. The housing 150012 is configured for operable attachment to an interchangeable shaft assembly 150200 that has an end effector 150300 operably coupled thereto that is configured to perform one or more surgical tasks or procedures. In accordance with the present disclosure, various forms of interchangeable shaft assemblies may be effectively employed in connection with robotically controlled surgical systems. The term "housing" may encompass a housing or similar portion of a robotic system that houses or otherwise operably supports at least one drive system configured to generate and apply at least one control motion that could be used to actuate interchangeable shaft assemblies. The term "frame" may refer to a portion of a handheld surgical instrument. The term "frame" also may represent a portion of a robotically controlled surgical instrument and/or a portion of the robotic system that may be used to operably control a surgical instrument. Interchangeable shaft assemblies may be employed with various robotic systems, instruments, components, and methods disclosed in U.S. Pat. No. 9,072,535, titled SURGICAL STAPLING INSTRUMENTS WITH ROTATABLE STAPLE DEPLOYMENT ARRANGEMENTS, which is herein incorporated by reference in its entirety.

Figure 16:
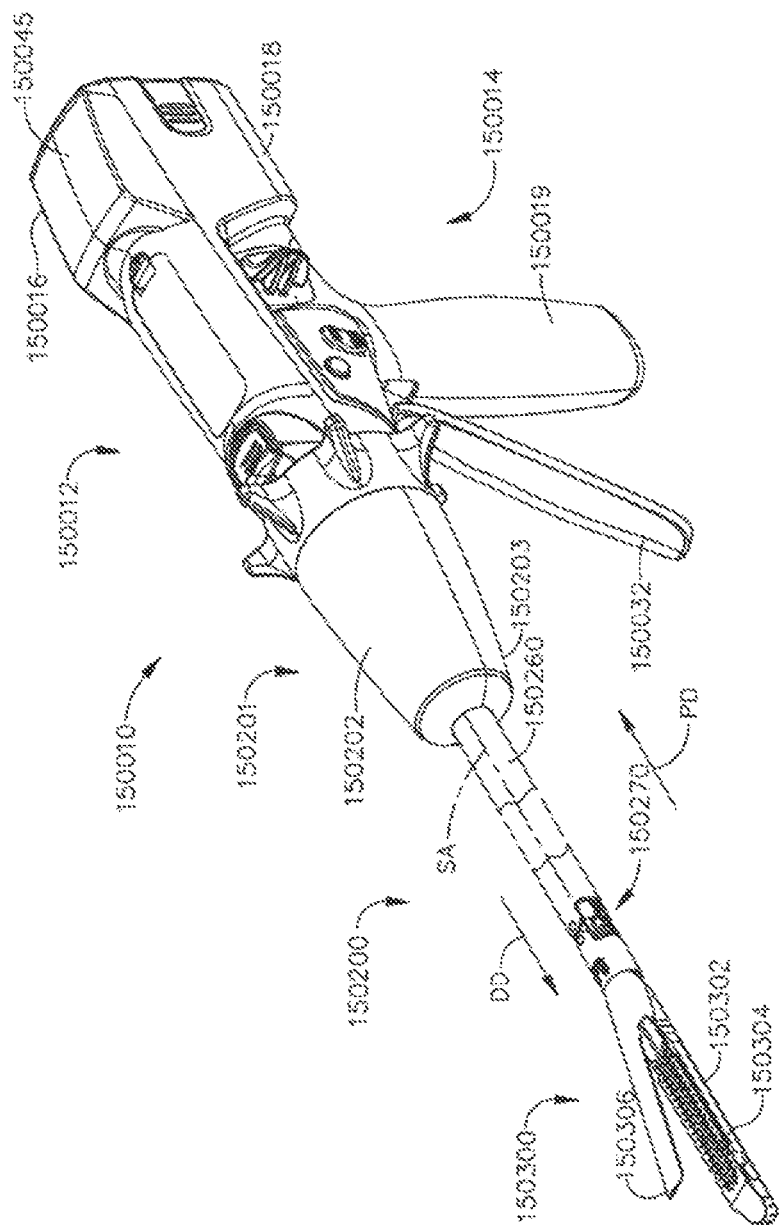
FIG. 16 illustrates a perspective view of an example surgical instrument that has an example interchangeable shaft assembly operably coupled thereto.

FIG. 16 is a perspective view of a surgical instrument 150010 that has an interchangeable shaft assembly 150200 operably coupled thereto, in accordance with at least one aspect of this disclosure. The housing 150012 includes an end effector 150300 that comprises a surgical cutting and fastening device configured to operably support a surgical staple cartridge 150304 therein. The housing 150012 may be configured for use in connection with interchangeable shaft assemblies that include end effectors that are adapted to support different sizes and types of staple cartridges, have different shaft lengths, sizes, and types. The housing 150012 may be employed with a variety of interchangeable shaft assemblies, including assemblies configured to apply other motions and forms of energy such as, radio frequency (RF) energy, ultrasonic energy, and/or motion to end effector arrangements adapted for use in connection with various surgical applications and procedures. The end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

The handle assembly 150014 may comprise a pair of interconnectable handle housing segments 150016, 150018 interconnected by screws, snap features, adhesive, etc. The handle housing segments 150016, 150018 cooperate to form a pistol grip portion 150019 that can be gripped and manipulated by the clinician. The handle assembly 150014 operably supports a plurality of drive systems configured to generate and apply control motions to corresponding portions of the interchangeable shaft assembly that is operably attached thereto. A display may be provided below a cover 150045.

Figure 17:
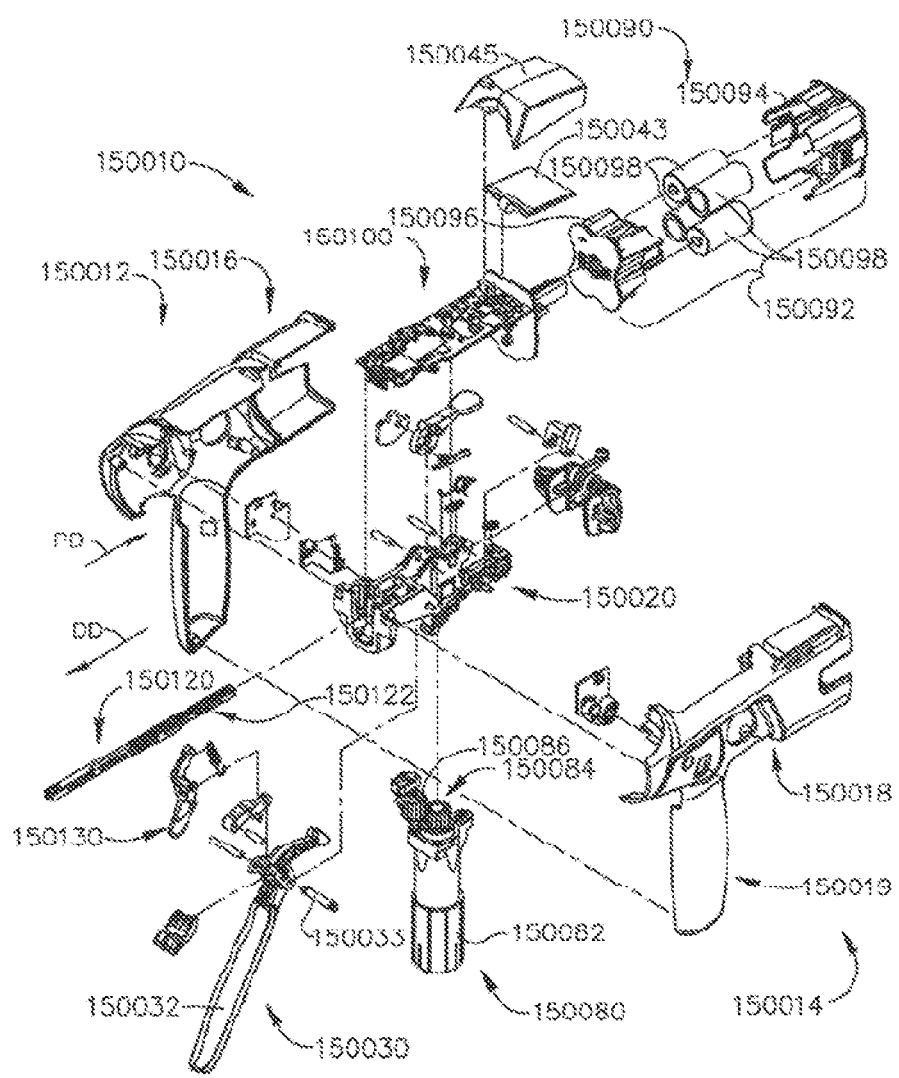
FIG. 17 illustrates an exploded assembly view of a portion of the example surgical instrument of FIG. 16.

FIG. 17 is an exploded assembly view of a portion of the surgical instrument 150010 of FIG. 16, in accordance with at least one aspect of this disclosure. The handle assembly 150014 may include a frame 150020 that operably supports a plurality of drive systems. The frame 150020 can operably support a "first" or closure drive system 150030, which can apply closing and opening motions to the interchangeable shaft assembly 150200. The closure drive system 150030 may include an actuator such as a closure trigger 150032 pivotally supported by the frame 150020. The closure trigger 150032 is pivotally coupled to the handle assembly 150014 by a pivot pin 150033 to enable the closure trigger 150032 to be manipulated by a clinician. When the clinician grips the pistol grip portion 150019 of the handle assembly 150014, the closure trigger 150032 can pivot from a starting or "unactuated" position to an "actuated" position and more particularly to a fully compressed or fully actuated position.

The handle assembly 150014 and the frame 150020 may operably support a firing drive system 150080 configured to apply firing motions to corresponding portions of the interchangeable shaft assembly attached thereto. The firing drive system 150080 may employ an electric motor 150082 located in the pistol grip portion 150019 of the handle assembly 150014. The electric motor 150082 may be a DC brushed motor having a maximum rotational speed of approximately 25,000 RPM, for example. In other arrangements, the motor may include a brushless motor, a cordless motor, a synchronous motor, a stepper motor, or any other suitable electric motor. The electric motor 150082 may be powered by a power source 150090 that may comprise a removable power pack 150092. The removable power pack 150092 may comprise a proximal housing portion 150094 configured to attach to a distal housing portion 150096. The proximal housing portion 150094 and the distal housing portion 150096 are configured to operably support a plurality of batteries 150098 therein. Batteries 150098 may each comprise, for example, a Lithium Ion (LI) or other suitable battery. The distal housing portion 150096 is configured for removable operable attachment to a control circuit board 150100, which is operably coupled to the electric motor 150082. Several batteries 150098 connected in series may power the surgical instrument 150010. The power source 150090 may be replaceable and/or rechargeable. A display 150043, which is located below the cover 150045, is electrically coupled to the control circuit board 150100. The cover 150045 may be removed to expose the display 150043.

The electric motor 150082 can include a rotatable shaft (not shown) that operably interfaces with a gear reducer assembly 150084 mounted in meshing engagement with a set, or rack, of drive teeth 150122 on a longitudinally movable drive member 150120. The longitudinally movable drive member 150120 has a rack of drive teeth 150122 formed thereon for meshing engagement with a corresponding drive gear 150086 of the gear reducer assembly 150084.

In use, a voltage polarity provided by the power source 150090 can operate the electric motor 150082 in a clockwise direction wherein the voltage polarity applied to the electric motor by the battery can be reversed in order to operate the electric motor 150082 in a counter-clockwise direction. When the electric motor 150082 is rotated in one direction, the longitudinally movable drive member 150120 will be axially driven in the distal direction "DD." When the electric motor 150082 is driven in the opposite rotary direction, the longitudinally movable drive member 150120 will be axially driven in a proximal direction "PD." The handle assembly 150014 can include a switch that can be configured to reverse the polarity applied to the electric motor 150082 by the power source 150090. The handle assembly 150014 may include a sensor configured to detect the position of the longitudinally movable drive member 150120 and/or the direction in which the longitudinally movable drive member 150120 is being moved.

Actuation of the electric motor 150082 can be controlled by a firing trigger 150130 that is pivotally supported on the handle assembly 150014. The firing trigger 150130 may be pivoted between an unactuated position and an actuated position.

Turning back to FIG. 16, the interchangeable shaft assembly 150200 includes an end effector 150300 comprising an elongated channel 150302 configured to operably support a surgical staple cartridge 150304 therein. The end effector 150300 may include an anvil 150306 that is pivotally supported relative to the elongated channel 150302. The interchangeable shaft assembly 150200 may include an articulation joint 150270. Construction and operation of the end effector 150300 and the articulation joint 150270 are set forth in U.S. Patent Application Publication No. 2014/0263541, titled ARTICULATABLE SURGICAL INSTRUMENT COMPRISING AN ARTICULATION LOCK, which is herein incorporated by reference in its entirety. The interchangeable shaft assembly 150200 may include a proximal housing or nozzle 150201 comprised of nozzle portions 150202, 150203. The interchangeable shaft assembly 150200 may include a closure tube 150260 extending along a shaft axis SA that can be utilized to close and/or open the anvil 150306 of the end effector 150300.

Turning back to FIG. 16, the closure tube 150260 is translated distally (direction "DD") to close the anvil 150306, for example, in response to the actuation of the closure trigger 150032 in the manner described in U.S. Patent Application Publication No. 2014/0263541. The anvil 150306 is opened by proximally translating the closure tube 150260. In the anvil-open position, the closure tube 150260 is moved to its proximal position.

Figure 18:
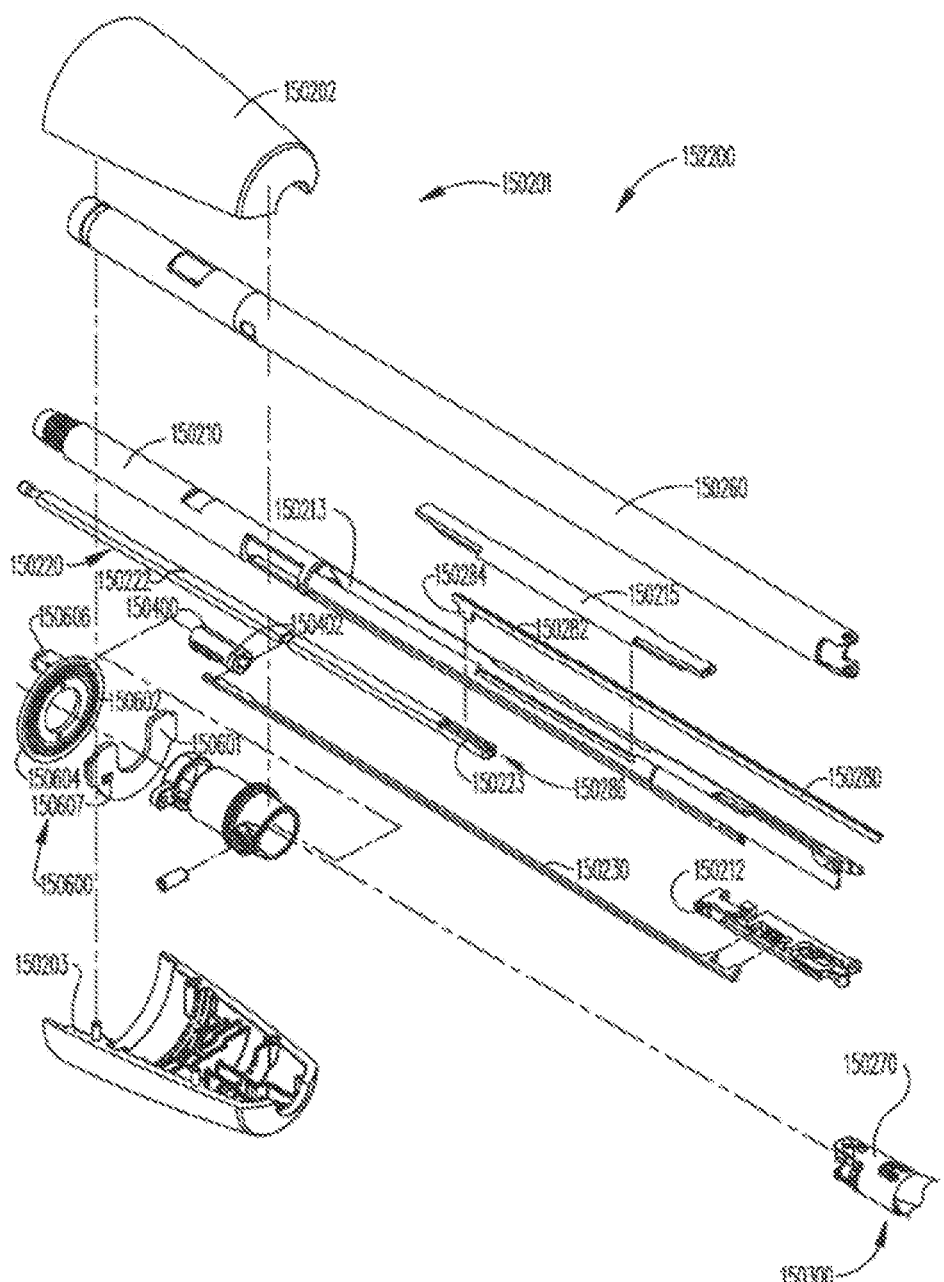
FIG. 18 illustrates an exploded assembly view of portions of the example interchangeable shaft assembly.

FIG. 18 is another exploded assembly view of portions of the interchangeable shaft assembly 150200, in accordance with at least one aspect of this disclosure. The interchangeable shaft assembly 150200 may include a firing member 150220 supported for axial travel within the spine 150210. The firing member 150220 includes an intermediate firing shaft 150222 configured to attach to a distal cutting portion or knife bar 150280. The firing member 150220 may be referred to as a "second shaft" or a "second shaft assembly". The intermediate firing shaft 150222 may include a longitudinal slot 150223 in a distal end configured to receive a tab 150284 on the proximal end 150282 of the knife bar 150280. The longitudinal slot 150223 and the proximal end 150282 may be configured to permit relative movement there between and can comprise a slip joint 150286. The slip joint 150286 can permit the intermediate firing shaft 150222 of the firing member 150220 to articulate the end effector 150300 about the articulation joint 150270 without moving, or at least substantially moving, the knife bar 150280. Once the end effector 150300 has been suitably oriented, the intermediate firing shaft 150222 can be advanced distally until a proximal sidewall of the longitudinal slot 150223 contacts the tab 150284 to advance the knife bar 150280 and fire the staple cartridge positioned within the channel 150302. The spine 150210 has an elongated opening or window 150213 therein to facilitate assembly and insertion of the intermediate firing shaft 150222 into the spine 150210. Once the intermediate firing shaft 150222 has been inserted therein, a top frame segment 150215 may be engaged with the shaft frame 150212 to enclose the intermediate firing shaft 150222 and knife bar 150280 therein. Operation of the firing member 150220 may be found in U.S. Patent Application Publication No. 2014/0263541. A spine 150210 can be configured to slidably support a firing member 150220 and the closure tube 150260 that extends around the spine 150210. The spine 150210 may slidably support an articulation driver 150230.

The interchangeable shaft assembly 150200 can include a clutch assembly 150400 configured to selectively and releasably couple the articulation driver 150230 to the firing member 150220. The clutch assembly 150400 includes a lock collar, or lock sleeve 150402, positioned around the firing member 150220 wherein the lock sleeve 150402 can be rotated between an engaged position in which the lock sleeve 150402 couples the articulation driver 150230 to the firing member 150220 and a disengaged position in which the articulation driver 150230 is not operably coupled to the firing member 150220. When the lock sleeve 150402 is in the engaged position, distal movement of the firing member 150220 can move the articulation driver 150230 distally and, correspondingly, proximal movement of the firing member 150220 can move the articulation driver 150230 proximally. When the lock sleeve 150402 is in the disengaged position, movement of the firing member 150220 is not transmitted to the articulation driver 150230 and, as a result, the firing member 150220 can move independently of the articulation driver 150230. The nozzle 150201 may be employed to operably engage and disengage the articulation drive system with the firing drive system in the various manners described in U.S. Patent Application Publication No. 2014/0263541.

The interchangeable shaft assembly 150200 can comprise a slip ring assembly 150600 which can be configured to conduct electrical power to and/or from the end effector 150300 and/or communicate signals to and/or from the end effector 150300, for example. The slip ring assembly 150600 can comprise a proximal connector flange 150604 and a distal connector flange 150601 positioned within a slot defined in the nozzle portions 150202, 150203. The proximal connector flange 150604 can comprise a first face and the distal connector flange 150601 can comprise a second face positioned adjacent to and movable relative to the first face. The distal connector flange 150601 can rotate relative to the proximal connector flange 150604 about the shaft axis SA-SA (FIG. 16). The proximal connector flange 150604 can comprise a plurality of concentric, or at least substantially concentric, conductors 150602 defined in the first face thereof. A connector 150607 can be mounted on the proximal side of the distal connector flange 150601 and may have a plurality of contacts wherein each contact corresponds to and is in electrical contact with one of the conductors 150602. Such an arrangement permits relative rotation between the proximal connector flange 150604 and the distal connector flange 150601 while maintaining electrical contact there between. The proximal connector flange 150604 can include an electrical connector 150606 that can place the conductors 150602 in signal communication with a shaft circuit board, for example. In at least one instance, a wiring harness comprising a plurality of conductors can extend between the electrical connector 150606 and the shaft circuit board. The electrical connector 150606 may extend proximally through a connector opening defined in the chassis mounting flange. U.S. Patent Application Publication No. 2014/0263551, titled STAPLE CARTRIDGE TISSUE THICKNESS SENSOR SYSTEM, is incorporated herein by reference in its entirety. U.S. Patent Application Publication No. 2014/0263552, titled STAPLE CARTRIDGE TISSUE THICKNESS SENSOR SYSTEM, is incorporated by reference in its entirety. Further details regarding slip ring assembly 150600 may be found in U.S. Patent Application Publication No. 2014/0263541.

The interchangeable shaft assembly 150200 can include a proximal portion fixably mounted to the handle assembly 150014 and a distal portion that is rotatable about a longitudinal axis. The rotatable distal shaft portion can be rotated relative to the proximal portion about the slip ring assembly 150600. The distal connector flange 150601 of the slip ring assembly 150600 can be positioned within the rotatable distal shaft portion.

Figure 19:
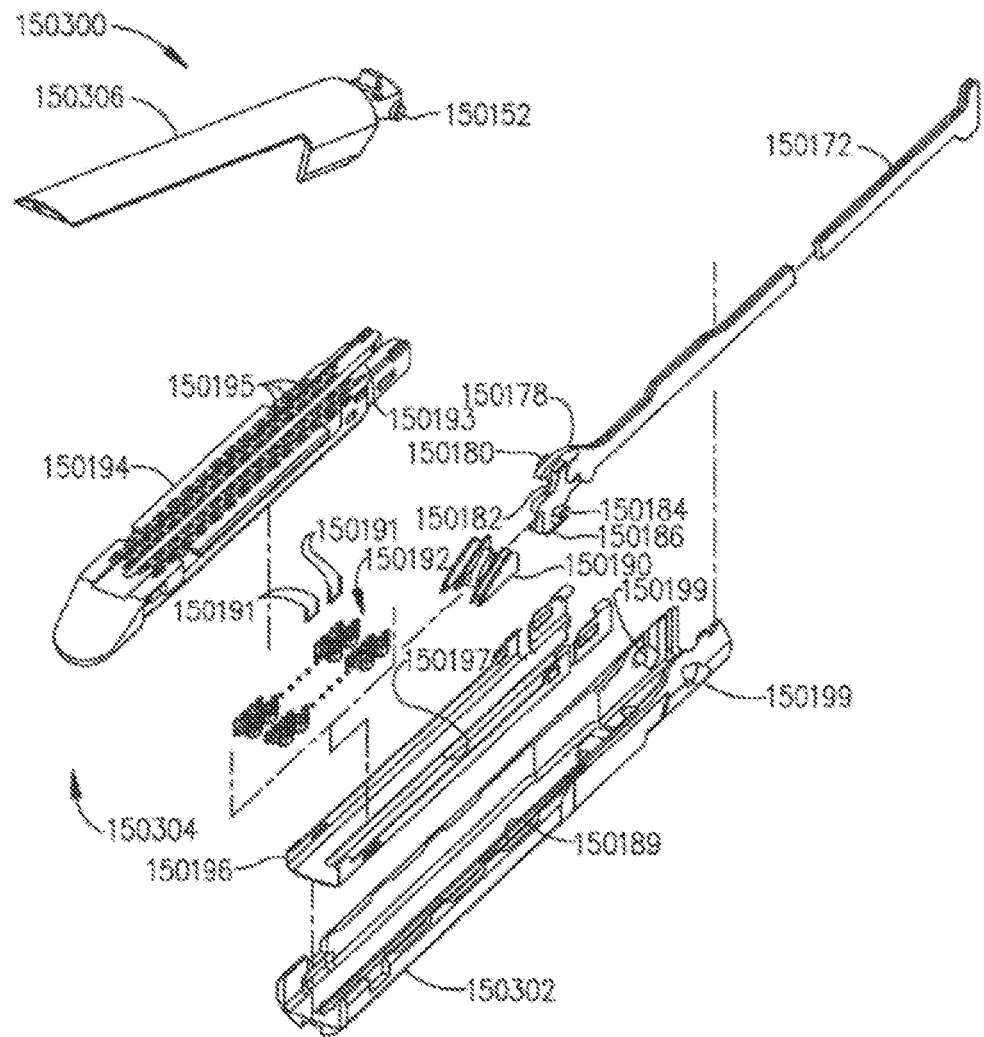
FIG. 19 illustrates an exploded view of an end effector of the example surgical instrument of FIG. 16.

FIG. 19 is an exploded view of one aspect of an end effector 150300 of the surgical instrument 150010 of FIG. 16, in accordance with at least one aspect of this disclosure. The end effector 150300 may include the anvil 150306 and the surgical staple cartridge 150304. The anvil 150306 may be coupled to an elongated channel 150302. Apertures 150199 can be defined in the elongated channel 150302 to receive pins 150152 extending from the anvil 150306 to allow the anvil 150306 to pivot from an open position to a closed position relative to the elongated channel 150302 and surgical staple cartridge 150304. A firing bar 150172 is configured to longitudinally translate into the end effector 150300. The firing bar 150172 may be constructed from one solid section, or may include a laminate material comprising a stack of steel plates. The firing bar 150172 comprises an I-beam 150178 and a cutting edge 150182 at a distal end thereof. A distally projecting end of the firing bar 150172 can be attached to the I-beam 150178 to assist in spacing the anvil 150306 from a surgical staple cartridge 150304 positioned in the elongated channel 150302 when the anvil 150306 is in a closed position. The I-beam 150178 may include a sharpened cutting edge 150182 to sever tissue as the I-beam 150178 is advanced distally by the firing bar 150172. In operation, the I-beam 150178 may, or fire, the surgical staple cartridge 150304. The surgical staple cartridge 150304 can include a molded cartridge body 150194 that holds a plurality of staples 150191 resting upon staple drivers 150192 within respective upwardly open staple cavities 150195. A wedge sled 150190 is driven distally by the I-beam 150178, sliding upon a cartridge tray 150196 of the surgical staple cartridge 150304. The wedge sled 150190 upwardly cams the staple drivers 150192 to force out the staples 150191 into deforming contact with the anvil 150306 while the cutting edge 150182 of the I-beam 150178 severs clamped tissue.

The I-beam 150178 can include upper pins 150180 that engage the anvil 150306 during firing. The I-beam 150178 may include middle pins 150184 and a bottom foot 150186 to engage portions of the cartridge body 150194, cartridge tray 150196, and elongated channel 150302. When a surgical staple cartridge 150304 is positioned within the elongated channel 150302, a slot 150193 defined in the cartridge body 150194 can be aligned with a longitudinal slot 150197 defined in the cartridge tray 150196 and a slot 150189 defined in the elongated channel 150302. In use, the I-beam 150178 can slide through the aligned longitudinal slots 150193, 150197, and 150189 wherein, as indicated in FIG. 19, the bottom foot 150186 of the I-beam 150178 can engage a groove running along the bottom surface of elongated channel 150302 along the length of slot 150189, the middle pins 150184 can engage the top surfaces of cartridge tray 150196 along the length of longitudinal slot 150197, and the upper pins 150180 can engage the anvil 150306. The I-beam 150178 can space, or limit the relative movement between, the anvil 150306 and the surgical staple cartridge 150304 as the firing bar 150172 is advanced distally to fire the staples from the surgical staple cartridge 150304 and/or incise the tissue captured between the anvil 150306 and the surgical staple cartridge 150304. The firing bar 150172 and the I-beam 150178 can be retracted proximally allowing the anvil 150306 to be opened to release the two stapled and severed tissue portions.

Figure 20A:
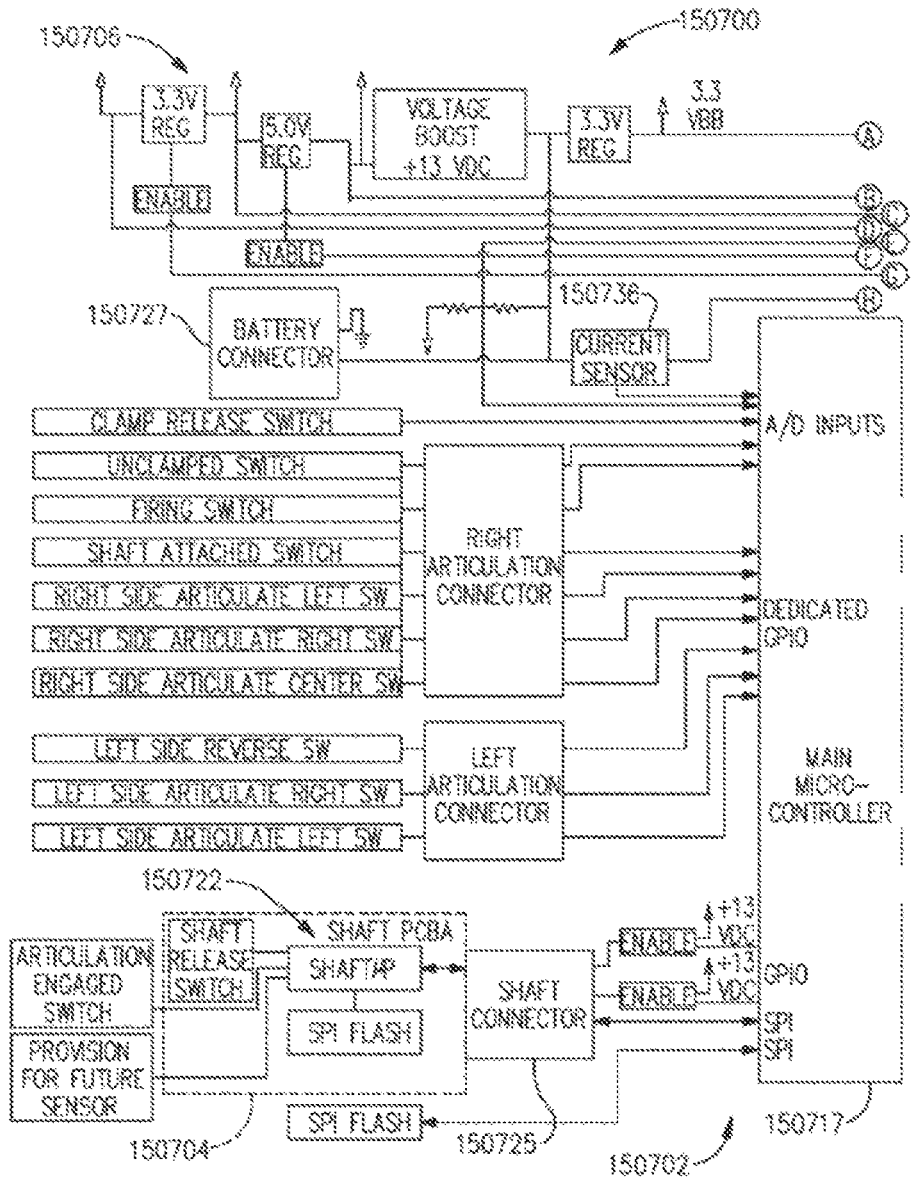
FIG. 20A illustrates a block diagram of a control circuit of the surgical instrument of FIG. 16 spanning two drawing sheets, in accordance with at least one aspect of this disclosure.
Figure 20B:
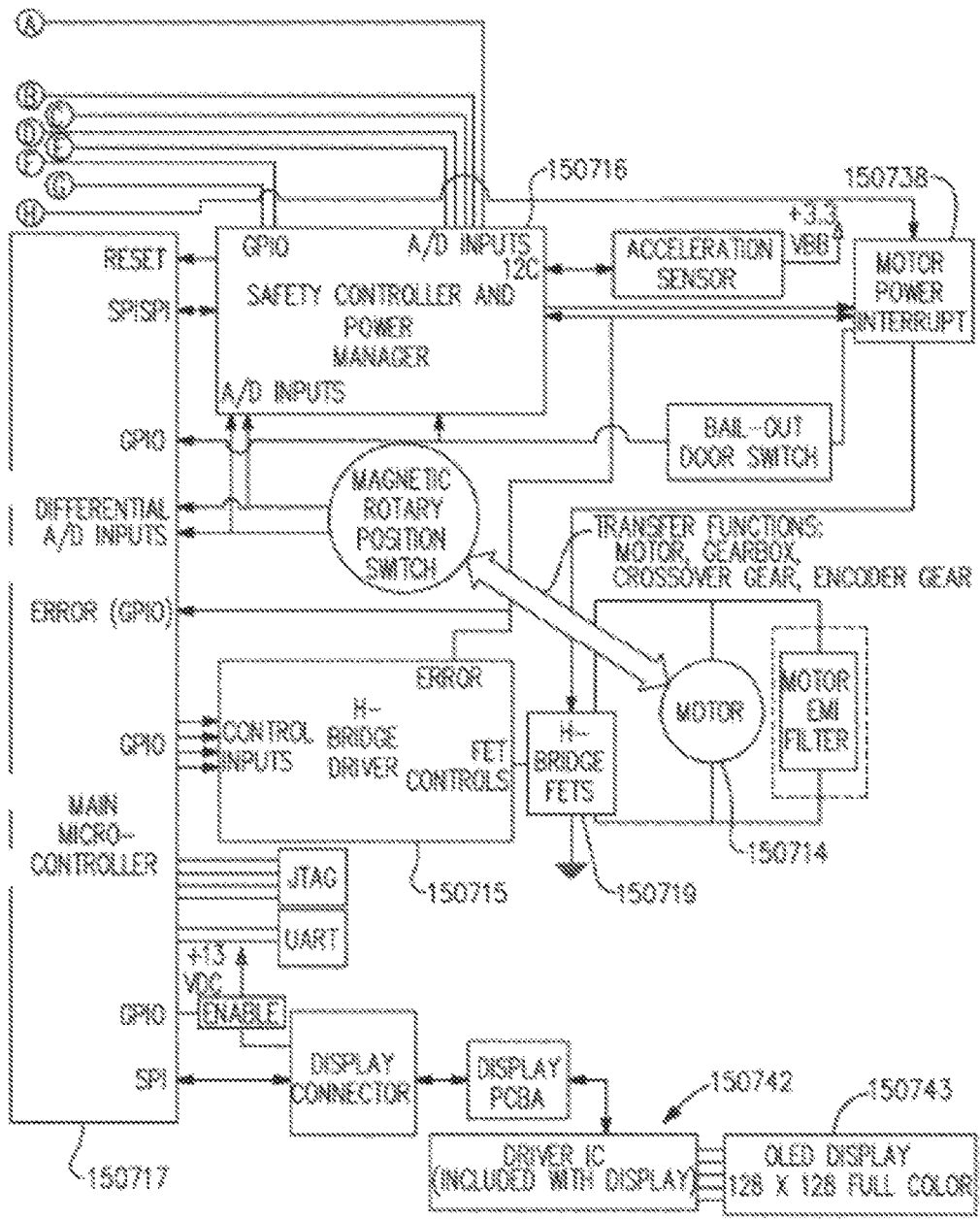
FIG. 20B illustrates a block diagram of a control circuit of the example surgical instrument of FIG. 16 spanning two drawing sheets.

FIGS. 20A and 20B is a block diagram of a control circuit 150700 of the surgical instrument 150010 of FIG. 16 spanning two drawing sheets, in accordance with at least one aspect of this disclosure. Referring primarily to FIGS. 20A and 20B, a handle assembly 150702 may include a motor 150714 which can be controlled by a motor driver 150715 and can be employed by the firing system of the surgical instrument 150010. In various forms, the motor 150714 may be a DC brushed driving motor having a maximum rotational speed of approximately 25,000 RPM. In other arrangements, the motor 150714 may include a brushless motor, a cordless motor, a synchronous motor, a stepper motor, or any other suitable electric motor. The motor driver 150715 may comprise an H-Bridge driver comprising field-effect transistors (FETs) 150719, for example. The motor 150714 can be powered by the power assembly 150706 releasably mounted to the handle assembly 150200 for supplying control power to the surgical instrument 150010. The power assembly 150706 may comprise a battery which may include a number of battery cells connected in series that can be used as the power source to power the surgical instrument 150010. In certain circumstances, the battery cells of the power assembly 150706 may be replaceable and/or rechargeable. In at least one example, the battery cells can be Lithium-Ion batteries which can be separably couplable to the power assembly 150706.

The shaft assembly 150704 may include a shaft assembly controller 150722 which can communicate with a safety controller and power management controller 150716 through an interface while the shaft assembly 150704 and the power assembly 150706 are coupled to the handle assembly 150702. For example, the interface may comprise a first interface portion 150725 which may include one or more electric connectors for coupling engagement with corresponding shaft assembly electric connectors and a second interface portion 150727 which may include one or more electric connectors for coupling engagement with corresponding power assembly electric connectors to permit electrical communication between the shaft assembly controller 150722 and the power management controller 150716 while the shaft assembly 150704 and the power assembly 150706 are coupled to the handle assembly 150702. One or more communication signals can be transmitted through the interface to communicate one or more of the power requirements of the attached interchangeable shaft assembly 150704 to the power management controller 150716. In response, the power management controller may modulate the power output of the battery of the power assembly 150706, as described below in greater detail, in accordance with the power requirements of the attached shaft assembly 150704. The connectors may comprise switches which can be activated after mechanical coupling engagement of the handle assembly 150702 to the shaft assembly 150704 and/or to the power assembly 150706 to allow electrical communication between the shaft assembly controller 150722 and the power management controller 150716.

The interface can facilitate transmission of the one or more communication signals between the power management controller 150716 and the shaft assembly controller 150722 by routing such communication signals through a main controller 150717 residing in the handle assembly 150702, for example. In other circumstances, the interface can facilitate a direct line of communication between the power management controller 150716 and the shaft assembly controller 150722 through the handle assembly 150702 while the shaft assembly 150704 and the power assembly 150706 are coupled to the handle assembly 150702.

The main controller 150717 may be any single core or multicore processor such as those known under the trade name ARM Cortex by Texas Instruments. In one aspect, the main controller 150717 may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

The safety controller may be a safety controller platform comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The power assembly 150706 may include a power management circuit which may comprise the power management controller 150716, a power modulator 150738, and a current sense circuit 150736. The power management circuit can be configured to modulate power output of the battery based on the power requirements of the shaft assembly 150704 while the shaft assembly 150704 and the power assembly 150706 are coupled to the handle assembly 150702. The power management controller 150716 can be programmed to control the power modulator 150738 of the power output of the power assembly 150706 and the current sense circuit 150736 can be employed to monitor power output of the power assembly 150706 to provide feedback to the power management controller 150716 about the power output of the battery so that the power management controller 150716 may adjust the power output of the power assembly 150706 to maintain a desired output. The power management controller 150716 and/or the shaft assembly controller 150722 each may comprise one or more processors and/or memory units which may store a number of software modules.

The surgical instrument 150010 (FIGS. 16 to 19) may comprise an output device 150742 which may include devices for providing a sensory feedback to a user. Such devices may comprise, for example, visual feedback devices (e.g., an LCD display screen, LED indicators), audio feedback devices (e.g., a speaker, a buzzer) or tactile feedback devices (e.g., haptic actuators). In certain circumstances, the output device 150742 may comprise a display 150743 which may be included in the handle assembly 150702. The shaft assembly controller 150722 and/or the power management controller 150716 can provide feedback to a user of the surgical instrument 150010 through the output device 150742. The interface can be configured to connect the shaft assembly controller 150722 and/or the power management controller 150716 to the output device 150742. The output device 150742 can instead be integrated with the power assembly 150706. In such circumstances, communication between the output device 150742 and the shaft assembly controller 150722 may be accomplished through the interface while the shaft assembly 150704 is coupled to the handle assembly 150702.

The control circuit 150700 comprises circuit segments configured to control operations of the powered surgical instrument 150010. A safety controller segment (Segment 1) comprises a safety controller and the main controller 150717 segment (Segment 2). The safety controller and/or the main controller 150717 are configured to interact with one or more additional circuit segments such as an acceleration segment, a display segment, a shaft segment, an encoder segment, a motor segment, and a power segment. Each of the circuit segments may be coupled to the safety controller and/or the main controller 150717. The main controller 150717 is also coupled to a flash memory. The main controller 150717 also comprises a serial communication interface. The main controller 150717 comprises a plurality of inputs coupled to, for example, one or more circuit segments, a battery, and/or a plurality of switches. The segmented circuit may be implemented by any suitable circuit, such as, for example, a printed circuit board assembly (PCBA) within the powered surgical instrument 150010. It should be understood that the term processor as used herein includes any microprocessor, processors, controller, controllers, or other basic computing device that incorporates the functions of a computer's central processing unit (CPU) on an integrated circuit or at most a few integrated circuits. The main controller 150717 is a multipurpose, programmable device that accepts digital data as input, processes it according to instructions stored in its memory, and provides results as output. It is an example of sequential digital logic, as it has internal memory. The control circuit 150700 can be configured to implement one or more of the processes described herein.

The acceleration segment (Segment 3) comprises an accelerometer. The accelerometer is configured to detect movement or acceleration of the powered surgical instrument 150010. Input from the accelerometer may be used to transition to and from a sleep mode, identify an orientation of the powered surgical instrument, and/or identify when the surgical instrument has been dropped. In some examples, the acceleration segment is coupled to the safety controller and/or the main controller 150717.

The display segment (Segment 4) comprises a display connector coupled to the main controller 150717. The display connector couples the main controller 150717 to a display through one or more integrated circuit drivers of the display. The integrated circuit drivers of the display may be integrated with the display and/or may be located separately from the display. The display may comprise any suitable display, such as, for example, an organic light-emitting diode (OLED) display, a liquid-crystal display (LCD), and/or any other suitable display. In some examples, the display segment is coupled to the safety controller.

The shaft segment (Segment 5) comprises controls for an interchangeable shaft assembly 150200 (FIGS. 16 and 18) coupled to the surgical instrument 150010 (FIGS. 16 to 19) and/or one or more controls for an end effector 150300 coupled to the interchangeable shaft assembly 150200. The shaft segment comprises a shaft connector configured to couple the main controller 150717 to a shaft PCBA. The shaft PCBA comprises a low-power microcontroller with a ferroelectric random access memory (FRAM), an articulation switch, a shaft release Hall effect switch, and a shaft PCBA EEPROM. The shaft PCBA EEPROM comprises one or more parameters, routines, and/or programs specific to the interchangeable shaft assembly 150200 and/or the shaft PCBA. The shaft PCBA may be coupled to the interchangeable shaft assembly 150200 and/or integral with the surgical instrument 150010. In some examples, the shaft segment comprises a second shaft EEPROM. The second shaft EEPROM comprises a plurality of algorithms, routines, parameters, and/or other data corresponding to one or more shaft assemblies 150200 and/or end effectors 150300 that may be interfaced with the powered surgical instrument 150010.

The position encoder segment (Segment 6) comprises one or more magnetic angle rotary position encoders. The one or more magnetic angle rotary position encoders are configured to identify the rotational position of the motor 150714, an interchangeable shaft assembly 150200 (FIGS. 16 and 18), and/or an end effector 150300 of the surgical instrument 150010 (FIGS. 16 to 19). In some examples, the magnetic angle rotary position encoders may be coupled to the safety controller and/or the main controller 150717.

The motor circuit segment (Segment 7) comprises a motor 150714 configured to control movements of the powered surgical instrument 150010 (FIGS. 16 to 19). The motor 150714 is coupled to the main microcontroller processor 150717 by an H-bridge driver comprising one or more H-bridge field-effect transistors (FETs) and a motor controller. The H-bridge driver is also coupled to the safety controller. A motor current sensor is coupled in series with the motor to measure the current draw of the motor. The motor current sensor is in signal communication with the main controller 150717 and/or the safety controller. In some examples, the motor 150714 is coupled to a motor electromagnetic interference (EMI) filter.

The motor controller controls a first motor flag and a second motor flag to indicate the status and position of the motor 150714 to the main controller 150717. The main controller 150717 provides a pulse-width modulation (PWM) high signal, a PWM low signal, a direction signal, a synchronize signal, and a motor reset signal to the motor controller through a buffer. The power segment is configured to provide a segment voltage to each of the circuit segments.

The power segment (Segment 8) comprises a battery coupled to the safety controller, the main controller 150717, and additional circuit segments. The battery is coupled to the segmented circuit by a battery connector and a current sensor. The current sensor is configured to measure the total current draw of the segmented circuit. In some examples, one or more voltage converters are configured to provide predetermined voltage values to one or more circuit segments. For example, in some examples, the segmented circuit may comprise 3.3V voltage converters and/or 5V voltage converters. A boost converter is configured to provide a boost voltage up to a predetermined amount, such as, for example, up to 13V. The boost converter is configured to provide additional voltage and/or current during power intensive operations and prevent brownout or low-power conditions.

A plurality of switches are coupled to the safety controller and/or the main controller 150717. The switches may be configured to control operations of the surgical instrument 150010 (FIGS. 16 to 19), of the segmented circuit, and/or indicate a status of the surgical instrument 150010. A bail-out door switch and Hall effect switch for bailout are configured to indicate the status of a bail-out door. A plurality of articulation switches, such as, for example, a left side articulation left switch, a left side articulation right switch, a left side articulation center switch, a right side articulation left switch, a right side articulation right switch, and a right side articulation center switch are configured to control articulation of an interchangeable shaft assembly 150200 (FIGS. 16 and 18) and/or the end effector 150300 (FIGS. 16 and 19). A left side reverse switch and a right side reverse switch are coupled to the main controller 150717. The left side switches comprising the left side articulation left switch, the left side articulation right switch, the left side articulation center switch, and the left side reverse switch are coupled to the main controller 150717 by a left flex connector. The right side switches comprising the right side articulation left switch, the right side articulation right switch, the right side articulation center switch, and the right side reverse switch are coupled to the main controller 150717 by a right flex connector. A firing switch, a clamp release switch, and a shaft engaged switch are coupled to the main controller 150717.

Any suitable mechanical, electromechanical, or solid state switches may be employed to implement the plurality of switches, in any combination. For example, the switches may be limit switches operated by the motion of components associated with the surgical instrument 150010 (FIGS. 16 to 19) or the presence of an object. Such switches may be employed to control various functions associated with the surgical instrument 150010. A limit switch is an electromechanical device that consists of an actuator mechanically linked to a set of contacts. When an object comes into contact with the actuator, the device operates the contacts to make or break an electrical connection. Limit switches are used in a variety of applications and environments because of their ruggedness, ease of installation, and reliability of operation. They can determine the presence or absence, passing, positioning, and end of travel of an object. In other implementations, the switches may be solid state switches that operate under the influence of a magnetic field such as Hall-effect devices, magneto-resistive (MR) devices, giant magneto-resistive (GMR) devices, magnetometers, among others. In other implementations, the switches may be solid state switches that operate under the influence of light, such as optical sensors, infrared sensors, ultraviolet sensors, among others. Still, the switches may be solid state devices such as transistors (e.g., FET, Junction-FET, metal-oxide semiconductor-FET (MOSFET), bipolar, and the like). Other switches may include wireless switches, ultrasonic switches, accelerometers, inertial sensors, among others.

Figure 21:
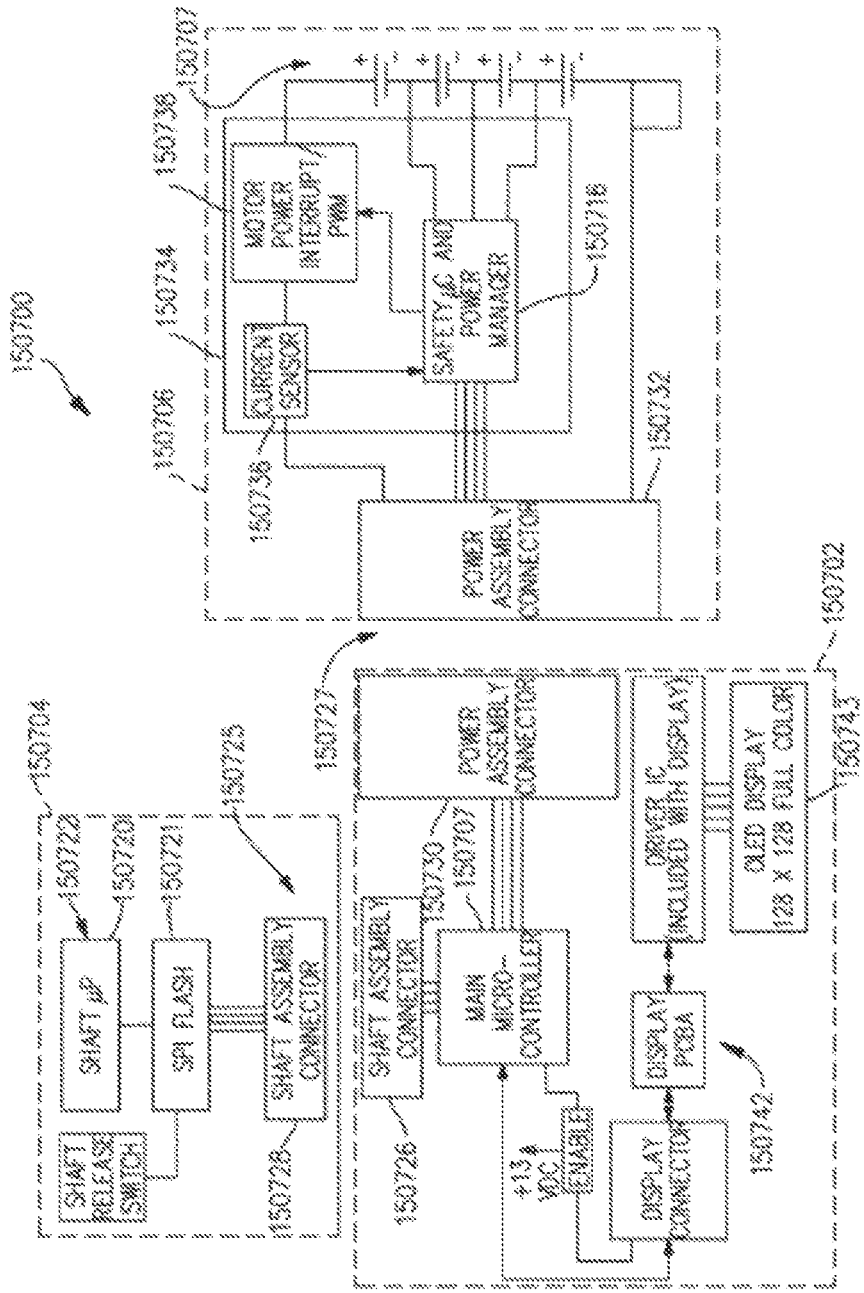
FIG. 21 illustrates a block diagram of the control circuit of the example surgical instrument of FIG. 16 illustrating interfaces between the handle assembly, the power assembly, and the handle assembly and the example interchangeable shaft assembly.

FIG. 21 is another block diagram of the control circuit 150700 of the surgical instrument of FIG. 16 illustrating interfaces between the handle assembly 150702 and the power assembly 150706 and between the handle assembly 150702 and the interchangeable shaft assembly 150704, in accordance with at least one aspect of this disclosure. The handle assembly 150702 may comprise a main controller 150717, a shaft assembly connector 150726 and a power assembly connector 150730. The power assembly 150706 may include a power assembly connector 150732, a power management circuit 150734 that may comprise the power management controller 150716, a power modulator 150738, and a current sense circuit 150736. The shaft assembly connectors 150730, 150732 form an interface 150727. The power management circuit 150734 can be configured to modulate power output of the battery 150707 based on the power requirements of the interchangeable shaft assembly 150704 while the interchangeable shaft assembly 150704 and the power assembly 150706 are coupled to the handle assembly 150702. The power management controller 150716 can be programmed to control the power modulator 150738 of the power output of the power assembly 150706 and the current sense circuit 150736 can be employed to monitor power output of the power assembly 150706 to provide feedback to the power management controller 150716 about the power output of the battery 150707 so that the power management controller 150716 may adjust the power output of the power assembly 150706 to maintain a desired output. The shaft assembly 150704 comprises a shaft processor 150720 coupled to a non-volatile memory 150721 and shaft assembly connector 150728 to electrically couple the shaft assembly 150704 to the handle assembly 150702. The shaft assembly connectors 150726, 150728 form interface 150725. The main controller 150717, the shaft processor 150720, and/or the power management controller 150716 can be configured to implement one or more of the processes described herein.

The surgical instrument 150010 (FIGS. 16 to 19) may comprise an output device 150742 to a sensory feedback to a user. Such devices may comprise visual feedback devices (e.g., an LCD display screen, LED indicators), audio feedback devices (e.g., a speaker, a buzzer), or tactile feedback devices (e.g., haptic actuators). In certain circumstances, the output device 150742 may comprise a display 150743 that may be included in the handle assembly 150702. The shaft assembly controller 150722 and/or the power management controller 150716 can provide feedback to a user of the surgical instrument 150010 through the output device 150742. The interface 150727 can be configured to connect the shaft assembly controller 150722 and/or the power management controller 150716 to the output device 150742. The output device 150742 can be integrated with the power assembly 150706. Communication between the output device 150742 and the shaft assembly controller 150722 may be accomplished through the interface 150725 while the interchangeable shaft assembly 150704 is coupled to the handle assembly 150702. Having described a control circuit 150700 (FIGS. 20A and 20B) for controlling the operation of the surgical instrument 150010 (FIGS. 16 to 19), the disclosure now turns to various configurations of the surgical instrument 150010 (FIGS. 16 to 19) and control circuit 150700.

Figure 22:
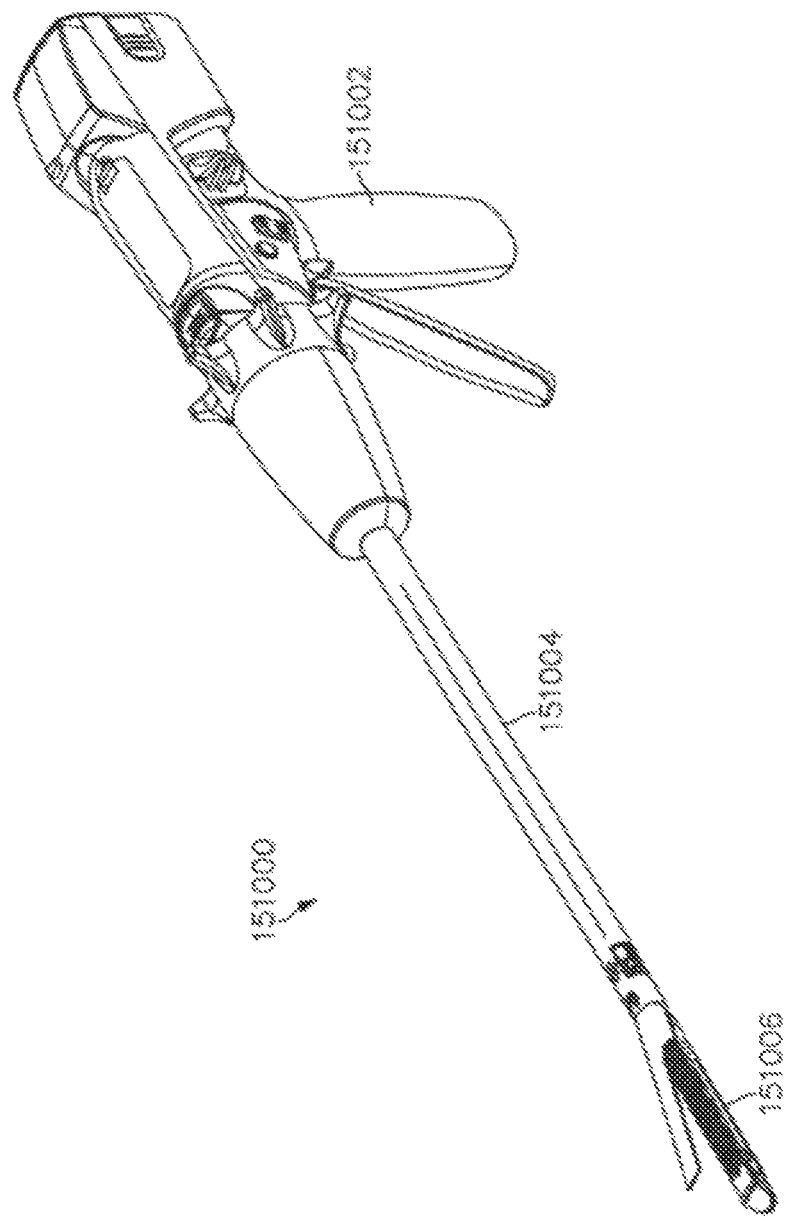
FIG. 22 illustrates an example medical device.
Figure 23:
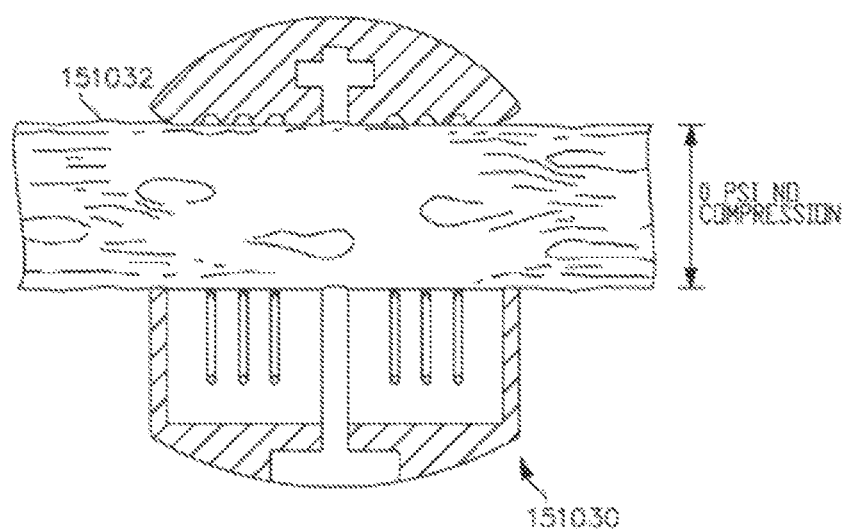
FIG. 23 illustrates an example end-effector of an example medical device surrounding tissue.
Figure 24:
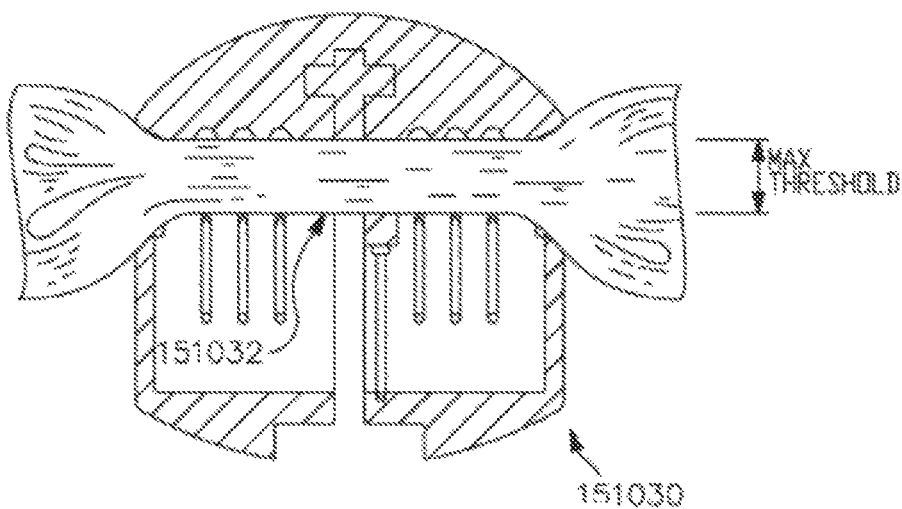
FIG. 24 illustrates an example end-effector of an example medical device compressing tissue.

Referring to FIG. 22, a surgical stapler 151000 may include a handle component 151002, a shaft component 151004, and an end-effector component 151006. The surgical stapler 151000 is similarly constructed and equipped as the motor-driven surgical cutting and fastening instrument 150010 described in connection with FIG. 16. Accordingly, for conciseness and clarity the details of operation and construction will not be repeated here. The end-effector 151006 may be used to compress, cut, or staple tissue. Referring now to FIG. 23, an end-effector 151030 may be positioned by a physician to surround tissue 151032 prior to compression, cutting, or stapling. As shown in FIG. 23, no compression may be applied to the tissue while preparing to use the end-effector. Referring now to FIG. 24, by engaging the handle (e.g., handle 151002) of the surgical stapler, the physician may use the end-effector 151030 to compress the tissue 151032. In one aspect, the tissue 151032 may be compressed to its maximum threshold, as shown in FIG. 24.

Figure 25:
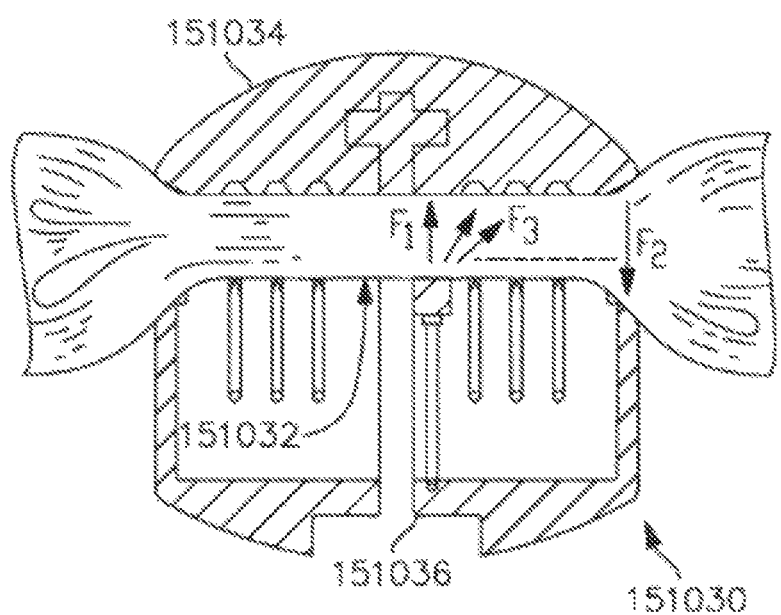
FIG. 25 illustrates example forces exerted by an end-effector of an example medical device compressing tissue.
Figure 26:
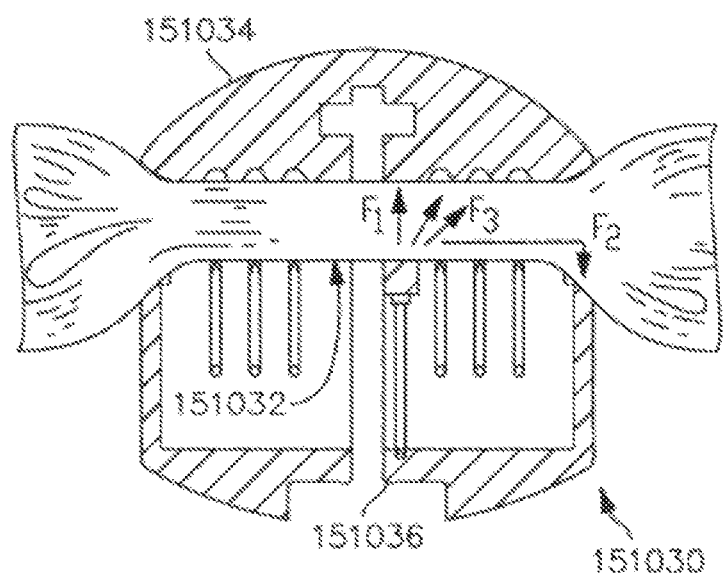
FIG. 26 illustrates example forces exerted by an end-effector of an example medical device compressing tissue.

Referring to FIG. 25, various forces may be applied to the tissue 151032 by the end-effector 151030. For example, vertical forces F1 and F2 may be applied by the anvil 151034 and the channel frame 151036 of the end-effector 151030 as tissue 151032 is compressed between the two. Referring now to FIG. 26, various diagonal and/or lateral forces also may be applied to the tissue 151032 when compressed by the end-effector 151030. For example, force F3 may be applied. For the purposes of operating a medical device such as surgical stapler 151000, it may be desirable to sense or calculate the various forms of compression being applied to the tissue by the end-effector. For example, knowledge of vertical or lateral compression may allow the end-effector to more precisely or accurately apply a staple operation or may inform the operator of the surgical stapler such that the surgical stapler can be used more properly or safely.

The compression through tissue 151032 may be determined from an impedance of tissue 151032. At various levels of compression, the impedance Z of tissue 151032 may increase or decrease. By applying a voltage V and a current I to the tissue 151032, the impedance Z of the tissue 151032 may be determined at various levels of compression. For example, impedance Z may be calculated by dividing the applied voltage V by the current I.

Figure 27:
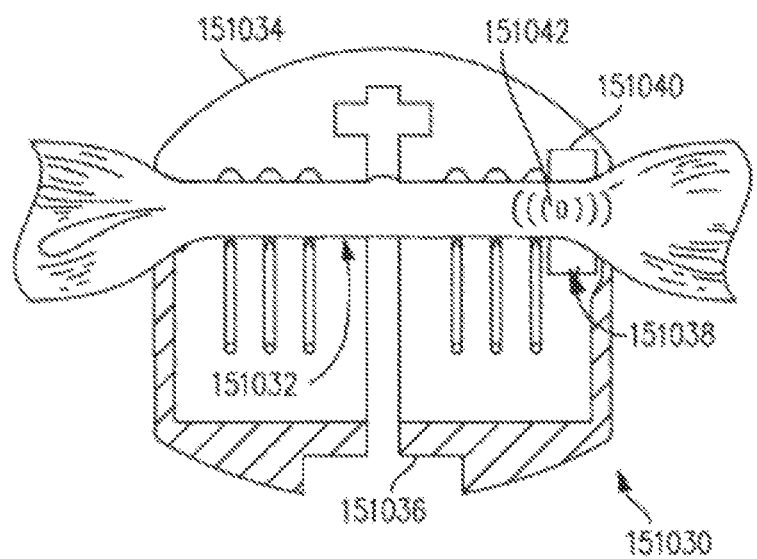
FIG. 27 illustrates an example tissue compression sensor system.

Referring now to FIG. 27, in one aspect, an RF electrode 151038 may be positioned on the end-effector 151030 (e.g., on a staple cartridge, knife, or channel frame of the end-effector 151030). Further, an electrical contact 151040 may be positioned on the anvil 151034 of the end-effector 151030. In one aspect, the electrical contact may be positioned on the channel frame of the end-effector. As the tissue 151032 is compressed between the anvil 151034 and, for example, the channel frame 151036 of the end-effector 151030, an impedance Z of the tissue 151032 changes. The vertical tissue compression 151042 caused by the end-effector 151030 may be measured as a function of the impedance Z of the tissue 151032.

Figure 28:
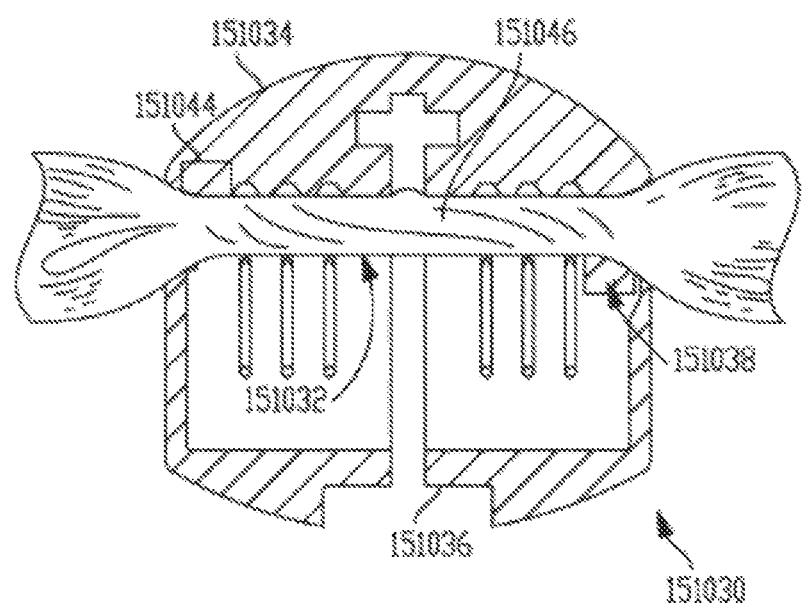
FIG. 28 illustrates an example tissue compression sensor system.

Referring now to FIG. 28, in one aspect, an electrical contact 151044 may be positioned on an opposite end of the anvil 151034 of the end-effector 151030 as the RF electrode 151038 is positioned. As the tissue 151032 is compressed between the anvil 151034 and, for example, the channel frame 151036 of the end-effector 151030, an impedance Z of the tissue 151032 changes. The lateral tissue compression 151046 caused by the end-effector 151030 may be measured as a function of the impedance Z of the tissue 151032.

Figure 29:
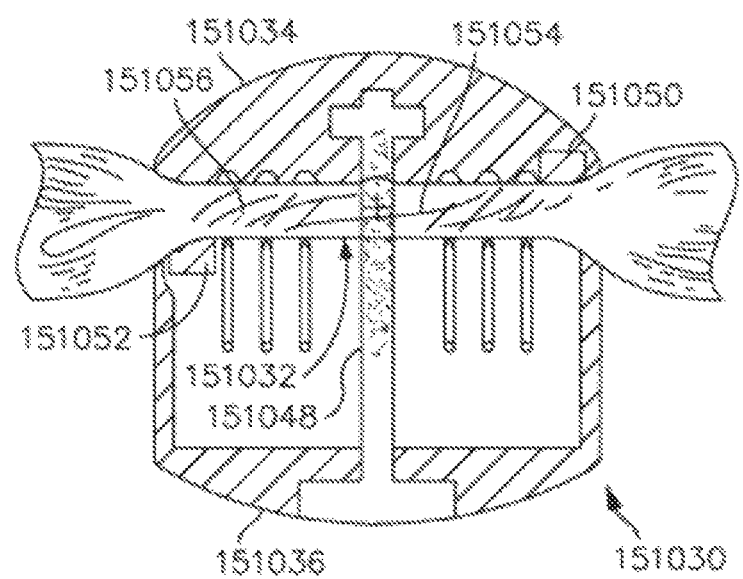
FIG. 29 illustrates an example tissue compression sensor system.

Referring now to FIG. 29, in one aspect, electrical contact 151050 may be positioned on the anvil 151034 and electrical contact 151052 may be positioned on an opposite end of the end-effector 151030 at channel frame 151036. RF electrode 151048 may be positioned laterally to the central to the end-effector 151030. As the tissue 151032 is compressed between the anvil 151034 and, for example, the channel frame 151036 of the end-effector 151030, an impedance Z of the tissue 151032 changes. The lateral compression or angular compressions 151054 and 151056 on either side of the RF electrode 151048 may be caused by the end-effector 151030 and may be measured as a function of different impedances Z of the tissue 151032, based on the relative positioning of the RF electrode 151048 and electrical contacts 151050 and 151052

Figure 30:
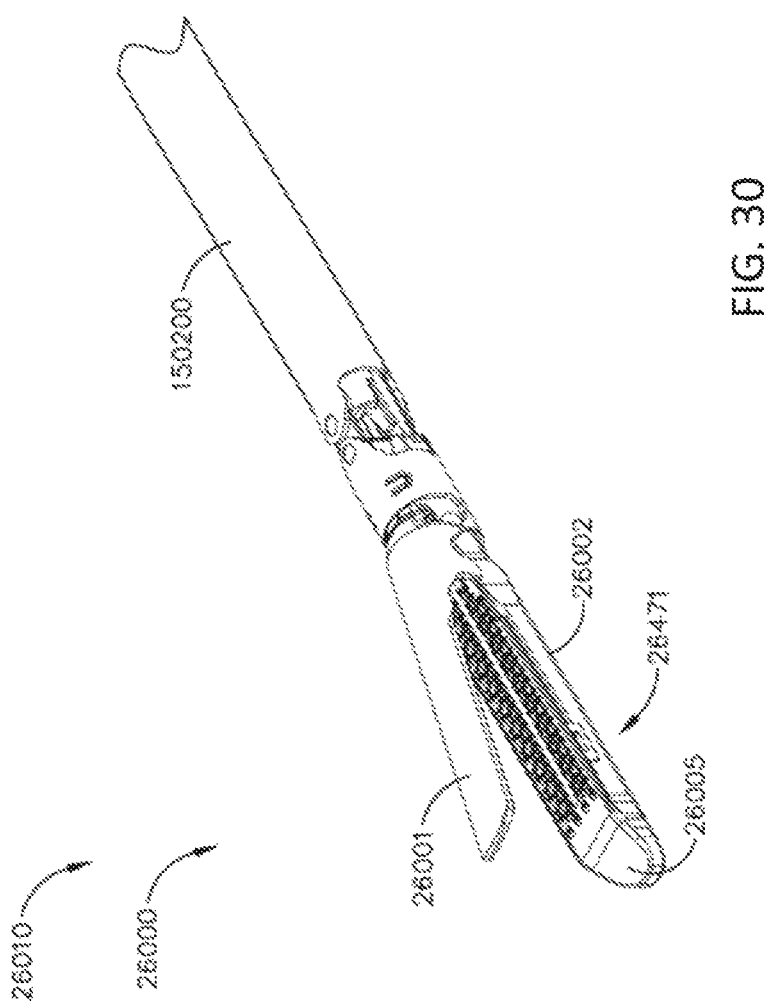
FIG. 30 illustrates an end effector of an example surgical instrument.
Figure 31:
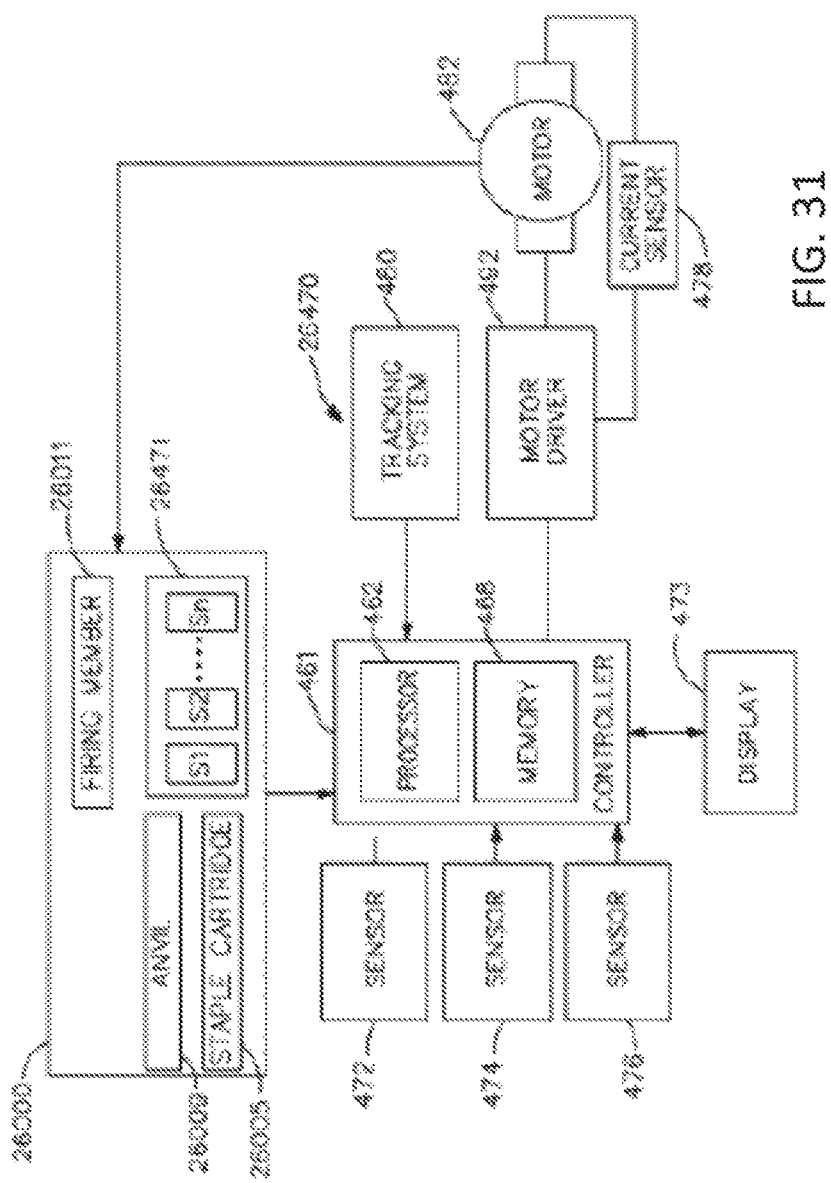
FIG. 31 illustrates a control system of an example surgical instrument.

The end effector 26000, as illustrated in FIGS. 30 and 31, includes a sensor array 26471 configured to generate or provide sensor signals indicative of a physiological parameter of the tissue that represents proximity of the end effector to cancerous tissue. FIG. 31 illustrates a control system 26470 including a control circuit coupled to the sensor array 26471. The control system 26470 is configured to assess proximity of the end effector 26000 to cancerous tissue based on the sensor signals of the sensor array 26471.

In one aspect, the physiological parameter is glucose level within the tissue. A low glucose level indicates a close proximity of the end effector to cancerous tissue.

Figure 32:
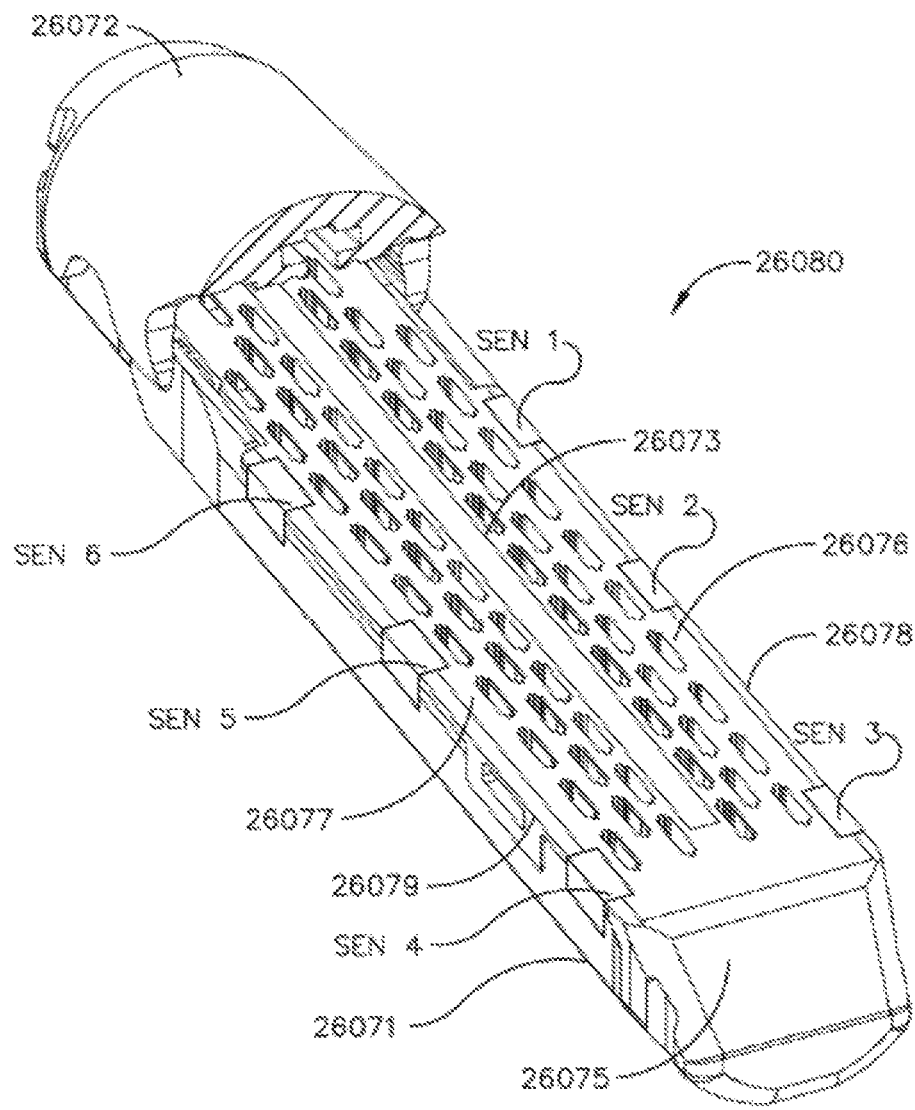
FIG. 32 illustrates a partial view of an end effector of an example surgical instrument.

In another aspect, the physiological parameter is a pH level. A low pH level indicates a close proximity of the end effector to cancerous tissue In various aspects, as illustrated in FIG. 32, an end effector 26070 may be equipped with a sensor array 26080 that includes six sensors ($Sen_1$-$Sen_6$): two proximal sensors ($Sen_1$ and $Sen_6$), two medial sensors ($Sen_2$ and $Sen_5$), and two distal sensors ($Sen_3$ and $Sen_4$). The added sensors allow the microcontroller 461, among other things, to more accurately predict the position of the end effector 26070 with respect to cancerous tissue.

The end effector 26070 is similar in many respects to the end effectors 26000, 26050. For example, the end effector 26070 includes a first jaw 26071 and a second jaw 26072. At least one of the first jaw 26071 and the second jaw 26072 is movable relative to the other to grasp tissue therebetween.

Further to the above, the end effector 26070 includes an anvil defined in the second jaw 26072 and a staple cartridge 26075 defined in the first jaw 26071. To treat tissue grasped by the end effector 26070, staples are deployed from the staple cartridge 26075 into the grasped tissue, and are deformed by the anvil. To cut the tissue, a transection member is moved relative to an elongated slot that defines a transection path 26073 for the transection member. The transection path 26073 defines two opposite sides 26076, 26077 of the end effector 26070.

Further to the above, the sensor array 26080 is similar in many respects to the sensor array 26471. For example, the sensor array 26080 can also be coupled to the microcontroller 461. The sensor array 26080 includes six sensors ($Sen_1$-$Sen_6$) configured to provide the microcontroller 461 with sensor signals according to a physiological parameter of the tissue that indicates proximity of the end effector 26070 to cancerous tissue. In other examples, the sensor array 26080, like the sensor array 26471, may include more or less than six sensors.

The sensors of the sensor array 26080 are spaced apart and arranged on outer edges 26078, 26079 of the staple cartridge 26075. In the example of FIG. 32, $Sen_1$, $Sen_2$, and $Sen_3$ are arranged on the side 26076 while $Sen_4$, $Sen_5$, and $Sen_6$ are arranged on the side 26077. In other words, the transection path 26052 extends between the sensors of the sensor array 26080.

In various examples, the differential between the sensor signals and the mean of the signals can give insight into tumor proximity. If a signal indicates a sensor is on a tumor, the differential between that sensor and the other sensors will give insight if the tumor is along one side (not transected) or across the transection path (transected). If the differential between the signals and mean is small but the mean is high, the entire end effector is on the tumor.

Cartridge Sensor Assemblies

Typical sensor assemblies utilized in surgical instruments are only able to passively detect tissue and physical environmental conditions, which can limit the amount, type, and detail of the data that they are able to detect. Aspects of the present disclosure present a solution, wherein the cartridges for use with the surgical instruments include active sensors that can be utilized to dynamically evaluate the tissue by stimulating or perturbing the tissue during the course of a surgical procedure and then detecting the corresponding response in the tissue. By applying a stimulus to the tissue through an active sensor incorporated with the cartridge, the surgical instrument can sense additional or different information than could have been detected using passive sensors.

Figure 33:
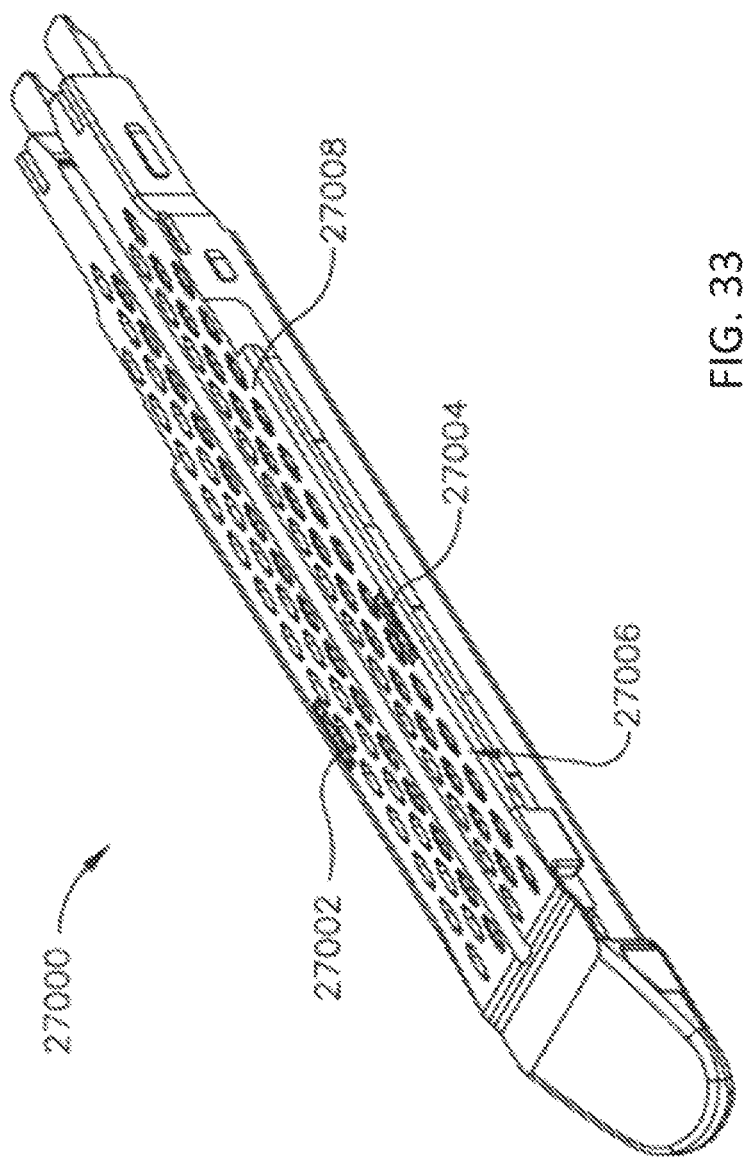
FIG. 33 illustrates a perspective view of an example staple cartridge including an active element and a sensor.

FIG. 33 illustrates a perspective view of a staple cartridge 27000 including an active sensor 27006, in accordance with at least one aspect of the present disclosure. The staple cartridge 27000 can be received within an end effector 150300 of a surgical instrument 150010, such as the surgical instrument 150010 described with respect to FIG. 16. In one aspect, the staple cartridge 27006 includes an active sensor 27006, which in turn includes an active element 27002 and a sensor 27004. The active sensor 27006 is configured to actively perturb or stimulate its environment, via the active element 27002, and then measure the corresponding environmental response, via the sensor 27004. The active sensor 27006 differs from passive sensors, which are configured to passively measure their environment.

The active element 27002 is configured to provide a stimulus to a tissue clamped by the end effector 150300 in which the staple cartridge 27000 is inserted (i.e., a tissue positioned or secured between the cartridge deck 27008 and the anvil 150306 of the end effector 150300). The sensor 27004 is configured to sense a tissue parameter associated with the perturbation or stimulus applied to the tissue and thereby determine the change in the tissue parameter resulting from the stimulus. In one aspect, the active element 27002 and the sensor 27004 are incorporated together or otherwise associated with each other to form an active sensor 27006 as single integral unit. In another aspect, the active element 27002 and the sensor 27004 are positioned separately from each other on or in the cartridge or otherwise disassociated with each other to form an active sensor 27006 as a distributed unit.

Figure 34:
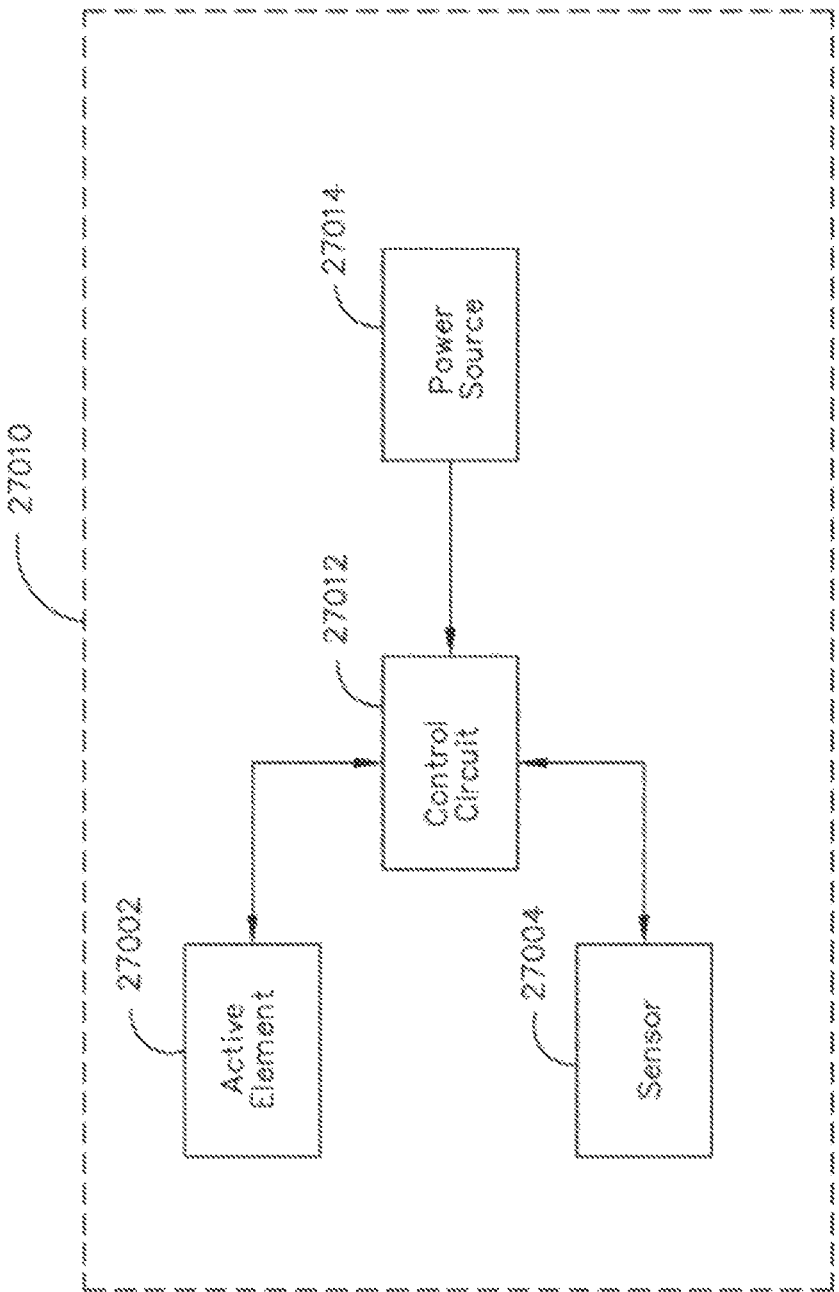
FIG. 34 illustrates a block diagram of an example active sensor assembly.

FIG. 34 illustrates a block diagram of a circuit 27010, in accordance with at least one aspect of the present disclosure. In one aspect, the cartridge 27000 includes a circuit 27010, which includes an active element 27002, a sensor 27004, a control circuit 27012 that is communicably connected to each of the active element 27002 and the sensor 27004, and a power source 27014 that is connected to the control circuit 27012 for supplying power thereto. The circuit 27010 and/or control circuit 27012 can include, for example, hardwired circuitry, programmable circuitry, state machine circuitry, firmware that stores instructions executed by programmable circuitry, and any combination thereof. In one aspect, the control circuit 27012 can be configured to activate the active element 27002, cause the active element 27002 to discharge or supply the stimulus to a tissue clamped by the end effector, or otherwise control the state of the active element 27002. The control circuit 27014 can be configured to activate the sensor 27004, receive data or an electrical signal indicative of a tissue property from the sensor 27004, or otherwise control the sensor 27004. In various aspects, either or both of the active element 27002 and the sensor 27004 can be exposed or positioned on the deck 27008 of the cartridge 27000 to contact a tissue positioned against the cartridge deck 27008, such as is illustrated in FIG. 33. In one aspect, the circuit 27010 illustrated in FIG. 34 can be embodied as a flex circuit. In one aspect, the circuit 27010 is a separate circuit from a cartridge circuit and/or a channel circuit, such as the cartridge circuit and channel circuit disclosed in U.S. patent application Ser. No. 15/636,096, filed Jun. 28, 2017, titled SURGICAL SYSTEM COUPLABLE WITH STAPLE CARTRIDGE AND RADIO FREQUENCY CARTRIDGE, AND METHOD OF USING SAME, which is hereby incorporated by reference herein in its entirety. In such aspects, the circuit 27010 may or may not be communicably coupled to the cartridge circuit and/or channel circuit. In another aspect, the circuit 27010 is integrated into the cartridge circuit and/or channel circuit.

In one aspect, the active element 27002 comprises a heating element and the sensor 27004 comprises a temperature sensor (e.g., a temperature measuring array). In this aspect, the active element 27002 is configured to provide a stimulus (perturbation) in the form of heat or thermal energy to a tissue grasped by the end effector 150300 and/or positioned against the cartridge deck 27008. Further, the sensor 27004 is configured to sense the physiologic response of the tissue to which the thermal energy from the active element 27002 is applied. The control circuit 27012 can thus be configured to evaluate the physiologic response of the tissue via data and/or signals received from the sensor 27004.

In one aspect, the active element 27002 is configured to apply thermal energy to a predetermined or localized area of a tissue grasped by the end effector 150300 and/or positioned against the cartridge deck 27008. For example, the heating element can comprise a heat sink (e.g., constructed from aluminum and/or copper) that is configured to convert electrical energy (e.g., from the power source 27014) into heat to apply thermal energy to a predetermined or localized area of a tissue adjacent or localized to the heat sink. In another aspect, the active element 27002 is configured to apply thermal energy across the entirety of or a larger portion of the surface of the cartridge deck 27008. For example, the heating element can comprise a flexible heating grid built into one or more of the layers of the cartridge circuit. In such aspects, the heating grid can be configured to enable the entirety or a large portion of the cartridge 27000 to emit thermal energy. Alternatively or additionally, the heating grid can be configured such that various regions of the heating grid can be activated to produce thermal energy. In this example, the heating grid can likewise be utilized to apply thermal energy at localized or predefined heating areas with a specified amount of thermal energy output to apply to a tissue.

Applying thermal energy to a tissue can be utilized to derive a variety of physiological information regarding the tissue. For example, the rate at which the temperature of a tissue rises is a function of its water content. Accordingly, applying thermal energy to a tissue can be utilized to determine the overall water content of the tissue by sensing the rate at which the temperature of the tissue increases in response to applied thermal energy. The water content of a tissue in turn corresponds to, for example, the tissue type. Further, applying thermal energy to different portions of a tissue can be utilized to determine the location(s) of high or low water content tissue by comparing the rates at which the temperatures of the different portions of the tissue increase in response to applied thermal energy.

In one aspect, the active element 27002 comprises a pressure-applying element and the sensor 27004 comprises a tissue compression sensor. The pressure-applying element can include, for example, a magnetic or electroactive polymer that, when energized, is configured to deform in shape and thereby apply a local pressure to a specific area of tissue situated thereagainst. The pressure-applying element can be disposed on, for example, the cartridge deck 27008 such that the pressure-applying element contacts and applies pressure to a tissue situated thereagainst. The tissue compression sensor can include, for example, an impedance sensor configured to measure an impedance of the tissue. As the impedance of the tissue can correspond to the thickness of the tissue (i.e., tissue compression), monitoring the time rate change of the tissue impedance can be utilized to monitor the change in the viscoelastic properties of the tissue over time in response to the pressure stimulus. Such viscoelastic properties of the tissue can include, for example, tissue creep and stability. The tissue compression sensor can also include, for example, a force sensor (e.g., a load cell or force-sensitive resistor) configured to sense a force or pressure exerted on the tissue or a gap sensor (e.g., a Hall effect sensor) configured to sense the gap or distance between the jaws (e.g., the anvil 150306 and/or channel 150302 of the surgical instrument 150010 depicted in FIG. 16) of the end effector 150300, which in turn corresponds to the degree to which a tissue grasped by the end effector 150300 is being compressed.

The magnetic or electroactive polymers can be configured to deform in a predetermined manner according to the manner in which they are manufactured. In one aspect, the control circuit 27012 can be configured to receive measurements from the sensor 27004 regarding the tissue compression while the added pressure is applied to determine accelerated creep aspects of the tissue. In one aspect, the control circuit 27012 can be configured to receive measurements from the sensor 27004 regarding the tissue pressure after the added pressure is relieved to evaluate the tissue recovery characteristics of the tissue.

Applying pressure to a tissue can be utilized to derive a variety of physiological information regarding the tissue. For example, the viscoelastic properties exhibited by a tissue correspond to its tissue type. In other words, different types of tissue each exhibit consistent viscoelastic properties. Accordingly, applying a pressure to a tissue can be utilized to determine the viscoelastic properties of a tissue by sensing the rate at which the tissue compresses, the rate at which the tissue returns to its prior shape when the pressure is removed, and other viscoelastic properties. Additional details regarding monitoring the viscoelastic properties of tissue can be found in U.S. Patent Publication No. 2016/0256156, filed Sep. 14, 2015, titled TIME DEPENDENT EVALUATION OF SENSOR DATA TO DETERMINE STABILITY, CREEP, AND VISCOELASTIC ELEMENTS OF MEASURES, which is hereby incorporated by reference herein in its entirety.

Surgical instrument cartridges may have multiple and/or duplicative means for storing or relaying data (i.e., data elements) associated with the cartridge. The data associated with the cartridge can include, for example, the cartridge type, characteristics of the cartridge, and whether the cartridge has been fired previously. Data redundancy is beneficial in avoiding total data loss if there is an error with one of the data elements or one of the data elements is destroyed. However, if one of the data elements incorrectly stores data, fails to store data, or has an error in transmitting the data, then an unresolvable conflict between the data elements may be created. When the surgical instrument or another system attempts to retrieve the data from the cartridge, the data conflict may cause errors in the surgical instrument or other system retrieving the data. Aspects of the present disclosure present a solution, wherein the surgical instruments are configured to resolve conflicts between data storage elements by prioritizing one of the data elements over the other data elements. In that way, the prioritized data element will supersede the other data elements, avoiding conflicts in attempting to select the proper cartridge data for use by the control circuit of the surgical instrument or another system.

Figure 35:
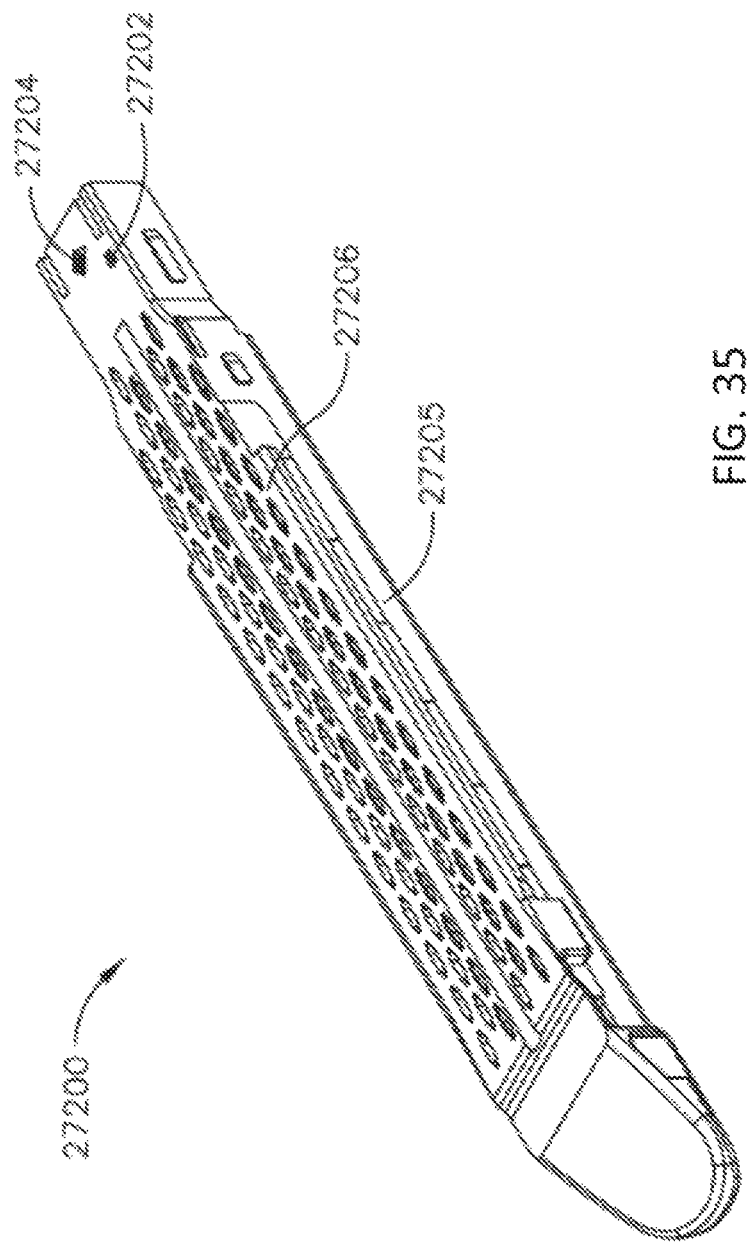
FIG. 35 illustrates a perspective view of an example cartridge including a pair of data elements.

FIG. 35 illustrates a perspective view of a cartridge 27200 including a pair of data elements, in accordance with at least one aspect of the present disclosure. In one aspect, the data elements include features, characteristics, and/or devices that are associated with the cartridge 27200 and are capable of storing, representing, and/or relaying data associated with the cartridge. The data elements can include, for example, a data storage element 27202 that is configured to store data related to the cartridge and a data-representative feature 27204 that is configured to represent data related to the cartridge. In some aspects, the data elements can be broadly characterized as automatic identification and data capture (AIDC) technologies. Although the cartridge depicted in FIG. 35 includes two data elements, in alternative aspects the cartridge can include one or more than two data elements in various combinations of data storage elements and data-representative features of the cartridge. Further, it should be noted that although the cartridge 27200 is depicted as a staple cartridge, the cartridge 27200 also includes RF cartridges and any other such cartridges.

In various aspects, the data-representative feature 27204 can include, for example, a physically or visually identifiable feature or structure that is associated with or disposed on the cartridge 27200. In one such aspect, the data-representative feature 27204 can include the material that the cartridge body 27205 is constructed from and/or the thickness of the cartridge body 27205. The cartridge body 27205 material and/or thickness can be different for the various cartridge types in order to create keyed resistance ranges for each cartridge type, which can then be detected by a sensor 27224 (FIG. 36) associated with the end effector 150300 of the surgical instrument 150302. The sensor 27224 for detecting the cartridge body 27205 material and/or thickness can be disposed in the channel 150302 of the end effector 150300 for example. In such aspects, the end effector 150300 could be electrically insulated.

In another such aspect, the data-representative feature 27204 can include a layer of material or a structure disposed on the cartridge deck 27206 (e.g., at the proximal end of cartridge deck 27206) that is configured to influence the initial phase of clamping force. For example, in FIG. 35 the data-representative feature 27204 includes a structure that extends generally orthogonally from the proximal end of the cartridge deck 27206 such that the anvil 150306 of the end effector 150300 would contact the structure as the anvil 150306 is clamped shut. The force as the anvil 150306 contacts the data-representative feature 27204 can then be detected by a control circuit 27222 (FIG. 36) via, e.g., a current sensor detecting the motor current (which corresponds to the force exerted by the anvil 150306 as the anvil 150306 is driven closed by a motor). The material and/or geometry of the data-representative feature(s) 27204 disposed on the cartridge deck 27206 can be customized for each of the various cartridge types to yield different detectable responses in the force to close (FTC) the anvil 150306. A control circuit 27222 coupled to a sensor capable of detecting the data-representative feature 27204 can thus determine the cartridge type according to the degree or level of the maximum FTC, the characteristics of the FTC response, and other such characteristics of the FTC detected over time. For example, a first cartridge type can include a data-representative feature 27204 that is constructed from a stiff material and a second cartridge type can include a data-representative feature 27204 that is constructed from a flexible material. According to the type of FTC response detected by the control circuit 27222, the control circuit 27222 can thus determine whether the anvil 150306 is making contact with a stiff or flexible structure as the anvil 150306 is closed and thereby determine whether the cartridge 27200 is the first cartridge type or the second cartridge type, respectively.

In various aspects, the data storage element 27202 can, for example, be associated with or disposed on the cartridge 27200 and be configured to transmit data stored by the data storage element 27202 via a wired or wireless connection. In one aspect, the data storage element 27202 comprises a RFID micro-transponder or RFID chip including a digital signature. In another such aspect, the data storage elements comprise a battery-assisted passive RFID tag. A battery-assisted passive RFD tag can exhibit improved range and signal length as compared to RFID micro-transponders and/or RFID chips. In this aspect, the RFID tag can include a writable section that could be used to store data associated with the cartridge 27200, such as whether the cartridge 27200 has been fired. Data can be written to the writable section of the cartridge 27200 via a circuit, such as a control circuit of the cartridge 27200 or the surgical instrument. The writable section could then be read subsequently by a sensor of the surgical instrument so that the surgical instrument can determine, for example, that the cartridge 27200 should not be re-fired.

In aspects wherein the data storage element 27202 includes an RFID tag utilizing ultra high-frequencies and higher frequencies, the RFID tag may be more than one radio wavelength away from the reader (sensor) of the surgical instrument. Therefore, simply transmitting the RF signal may not be sufficient to communicate the data from the RFID tag. In these aspects, the RFID tag can be configured to backscatter a signal. The active RFID tags may contain transmitters and receivers that are functionally separated and the RFID tags need not respond on a frequency related to the reader's interrogation signal.

In another aspect, the data storage element 27202 can include a one-wire chip configured to store identification data. The data storage element 27202 can be configured to transmit or provide the stored identification data to the surgical instrument, either upon the cartridge 27200 being inserted in the end effector or in response to receiving a query from the surgical instrument. In such aspects, the one-wire chip can include a writable section that could be used to store data associated with the cartridge 27200, such as whether the cartridge 27200 has been fired. In another such aspect, the data storage elements comprise an integrated circuit (IC) executing a particular communication protocol, such as an I-squared-C (i.e., I-two-C), SPI, or other multi-master, multi-slave, packet-switched, single-ended, serial computer bus. Various additional details regarding wired electrical connections between the cartridge 27200 and the surgical instrument can be found in U.S. patent application Ser. No. 15/636,096, filed Jun. 28, 2017, titled SURGICAL SYSTEM COUPLABLE WITH STAPLE CARTRIDGE AND RADIO FREQUENCY CARTRIDGE, AND METHOD OF USING SAME, which is hereby incorporated by reference herein in its entirety.

Although FIG. 35 depicts a cartridge 27200 including a single data-representative feature 27204 and a single data storage element 27202, it should be noted that different aspects of the cartridge 27200 can include various combinations of the aforementioned data elements. In other words, various aspects of the cartridge 27200 can include combinations of multiple data-representative features 27204, multiple data storage elements 27202, different types of data storage elements 27202 and/or data-representative features 27204, and so on.

The data storage element 27202 can store or represent a variety of data pertaining to the cartridge 27200, including, for example, data identifying the cartridge type and data identifying characteristics of the cartridge (e.g., the cartridge size). In one aspect, the data storage element 27202 can be configured to store an Electronic Product Code (EPC). In aspects wherein the data storage element is an RFID tag, the EPC can be written into the tag by an RFID printer and can contain, for example, a 96-bit string of data. The string of data can include, for example, a header (e.g., of eight bits) identifying the version of the protocol; an organization number (e.g., of 28 bits) that identifies the organization that manages the data for this tag (which can be assigned by the EPC Global consortium); an object class (e.g., of 24 bits) identifying the kind of product; and a unique serial number (e.g., of 36 bits) for a particular tag. The object class and unique serial number fields can be set by the organization that issued the tag. Similarly to a URL, the EPC number can be used as a key into a global database to uniquely identify a particular product.

Figure 36:
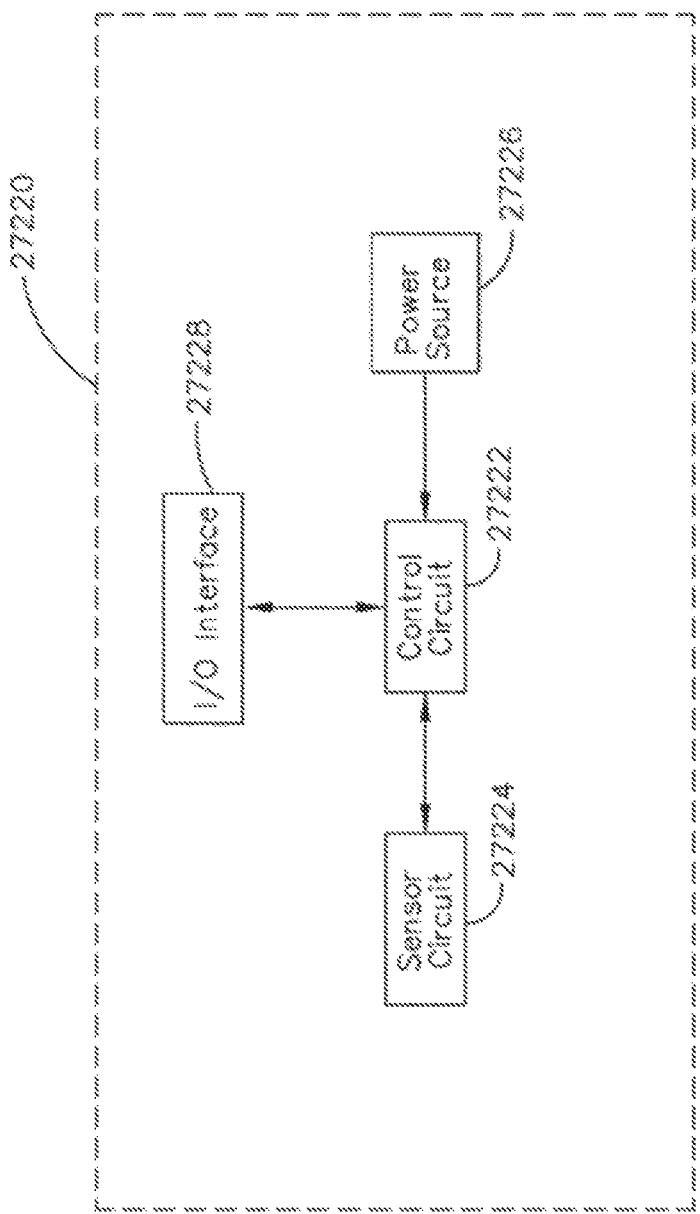
FIG. 36 illustrates a block diagram of an example sensor assembly for detecting and/or receiving data from data elements associated with a cartridge.

FIG. 36 illustrates a block diagram of a sensor assembly 27220 for detecting and/or receiving data from data elements associated with a cartridge 27200, in accordance with at least one aspect of the present disclosure. In the following description of the sensor assembly 27220, reference should also be made to FIG. 35. The sensor assembly 27220 can be included in or communicably coupled with a surgical instrument that is configured to receive a cartridge 27200. In one aspect, the sensor assembly 27220 includes a control circuit 27222 communicably connected to a sensor 27224 configured to detect a data-representative feature 27204 representing cartridge data and an I/O interface 27228 that is configured to receive data from a data storage element 27202 storing cartridge data. In one aspect, the sensor assembly 27220 be a component of or integrated with a circuit disposed in the channel 150302 (FIG. 16) of the end effector 150300, such as the channel circuit disclosed in U.S. patent application Ser. No. 15/636,096. In another aspect, the sensor assembly 27220 be a distinct or separate from the channel circuit, such as the channel circuit disclosed in U.S. patent application Ser. No. 15/636,096. The control circuit 27222 is further connected to a power source to draw power therefrom. The sensor 27224 can include any type of sensor that is able to identify a particular physical or visual feature identifying the cartridge 27200. In one aspect, the sensor 27224 can include a current sensor that is configured to detect the current drawn by a motor during at least the initial or clamping portion of the firing member stroke, thereby allowing the control circuit 27222 to determine the FTC and thereby determine whether the anvil 150306 of the end effector 150300 is encountering a physical feature disposed on the cartridge 27200 identifying the cartridge type, as described above. In another aspect, the sensor 27224 can include an optical sensor configured to detect an icon, color, bar code, or other marking or series of markings disposed on the cartridge 27200 that identify the cartridge type. In one aspect, the I/O interface 27228 can include bus wires (e.g., cartridge and channel electrical contacts disclosed in U.S. patent application Ser. No. 15/636,096) configured to electrically connect to a data storage element 27202 storing data to receive the data stored thereon utilizing a wired communication protocol (e.g., I-squared-C). In another aspect, the I/O interface 27228 can include a wireless transmitter configured to wirelessly connect to a data storage element 27202 storing data to receive the data stored thereon utilizing a wireless communication protocol (e.g., Bluetooth).

Other aspects of the sensor assembly 27220 can include various combinations of sensors 27224 configured to detect data-representative features 27204 and I/O interfaces 27228 configured to receive data from data storage elements 27202 associated with a cartridge 2700, including multiple sensors 27224 (of the same or different types), multiple I/O interfaces 27228 (of the same or different types), no I/O interfaces 27228, no sensors 27224, and all combinations thereof. The particular combination of sensors 27224 and/or I/O interfaces 27228 included in the sensor assembly 27220 to detect data associated with the cartridge 27200 corresponds to the combination of data elements utilized by the cartridge 27200 to store cartridge data.

A surgical instrument may be adapted to communicate with components that interface with the surgical instrument. For example, a surgical instrument, which may be a surgical stapler, may be configured to communicate with a surgical staple cartridge that is removably attached to the surgical stapler. A surgical instrument may be configured to control the communication capability or capacity between the surgical instrument and the components attached to it. The surgical instrument may provide different levels or tiers of communication between the surgical instrument and the components. For example, a surgical stapler may configure communication with an attached surgical staple cartridge to allow for one or more of the following communication tiers: one-way static communication with the surgical staple cartridge; two-way communication with the surgical staple cartridge; real-time two-way communication with the surgical staple cartridge; and communication with a surgical hub or other computing system.

A surgical instrument may be configured to determine the communication capability including a type or degree of communication to provide depending upon parameters or data associated with the instrument, the component attached to the device, the operator of the device, the owner of the device, or other relevant element. For example, a surgical instrument may determine the type and degree of communication between the surgical instrument and a component based on a parameter indicating a purchase or subscription level associated with the surgical instrument or attached component. If a surgical stapler or a surgical staple cartridge attached to the surgical stapler is associated with a low purchase or subscription level, the surgical stapler may determine that the surgical stapler may provide one-way static communication from the surgical staple cartridge to the surgical stapler. If the surgical stapler or surgical staple cartridge is associated with a higher purchase or subscription level, the surgical stapler may determine that the surgical stapler may provide real-time two-way communication between the surgical stapler and the surgical staple cartridge.

A surgical instrument may determine the communication capability between the surgical instrument and component based on parameters of the surgical instrument and/or component. If a surgical staple cartridge attached to a surgical stapler is configured with relatively outdated software, the surgical stapler may determine that the communication capability with the surgical staple cartridge may comprise one-way communication of static data from the surgical staple cartridge to the surgical stapler. If the surgical staple cartridge attached to the surgical stapler is configured with relatively recent software, the surgical stapler may determine that the communication capability with the surgical stapler cartridge may comprise two-way real-time communication.

Figures 37A, 37B:
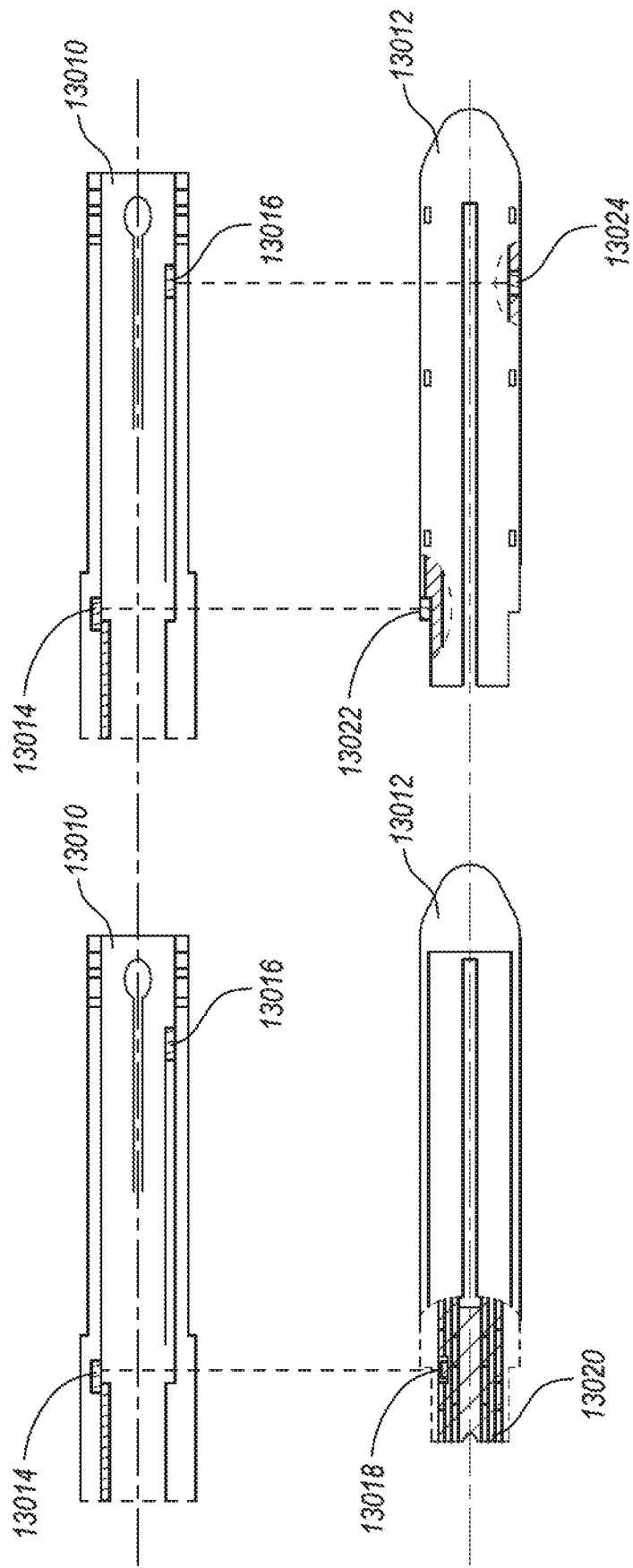
FIG. 37A illustrates an example surgical staple cartridge.
FIG. 37B illustrates an example surgical staple cartridge.

Communication between a surgical instrument and a component engaged with the surgical instrument may be performed using, for example, sensing arrays and communication devices. A surgical instrument and the corresponding component may comprise sensing arrays and communications devices that are positioned so as to communicatively couple the component and surgical instrument. FIG. 37A depicts an example coupling between a surgical stapler's elongated channel 13010 and a surgical staple cartridge 13012 that is coupled with the surgical stapler. As shown, the elongated channel 13010 may comprise a first sensing array 13014 positioned along a first side of the channel and at a proximal end of the elongated channel 13010. The elongated channel 13010 may further comprise a second sensing array 13016 longitudinally displaced from the first sensing array 13014 and positioned along an opposite side of the elongated channel 13010 and proximate a distal end of the elongated channel 13010. The sensing arrays 13014 and 13016 may be configured to sense data communicated by corresponding communication devices comprised in the surgical staple cartridge 13012. The sensing arrays 13014 and 13016 may be further configured to communicate data and power to corresponding communication devices in the surgical staple cartridge 13012.

The surgical staple cartridge 13012 may comprise one or more communication devices such as, for example, a Radio Frequency Identification chip (RFID) 13018. The RFID chip 13018 may be positioned in a sled 13020 comprised in the surgical staple cartridge 13012. In the example depicted in FIG. 37A, the RFID chip 13018 may be located in an initial home position and may align with the first sensing array 13014 comprised in the elongated channel 13010 of the surgical stapler. In an example, the RFID chip may be configured to communicate data identifying the surgical stapler cartridge 13012 along with data identifying a status of the cartridge to the sensing array 13014. In the example of FIG. 37A, the second communication array 13016 may not align with or correspond to a communication device in the surgical stapler cartridge 13012.

FIG. 37B depicts an example communication and power coupling between a surgical stapler's elongated channel 13010 and a surgical stapler 13012. As shown, the elongated channel 13010 comprises the first array 13014 positioned along a first side of the channel and at a proximal end of the elongated channel 13010. The elongated channel 13010 may further comprise a second array 13016 longitudinally displaced from the first sensing array 13014 and positioned along an opposite side of the elongated channel 13010 and proximate a distal end of the elongated channel 13010. Surgical stapler cartridge 13012 may comprise a first array 13022 positioned in the proximal end of the cartridge and a second array 13024 positioned near a distal end of the cartridge. When surgical staple cartridge 13012 is interfaced with the elongated channel 150302 of the surgical stapler, the first sensing array 13022 may align with and communicate with array 13014. The second sensing array 13024 may align with and communicate with array 13016. Data may be communicated between the surgical stapler and the surgical staple cartridge 13012 using the aligned arrays. For example, data relating to measurements such as tissue measurements that are gathered by other sensors in the surgical staple cartridge 13012 may be communicated by arrays 13022 and 13024. Likewise, power may be communicated from the surgical stapler and arrays 13014 and 13016 to arrays 13022 and 13024. The power may be used by the surgical staple cartridge 13012 to operate sensors the collect data regarding tissue that is operated on by the surgical staple cartridge 13012. This data may be communicated by arrays 13022 and 13023 to arrays 13014 and 13016. The arrays may be configured to send and receive data in any suitable combination.

Figure 38:
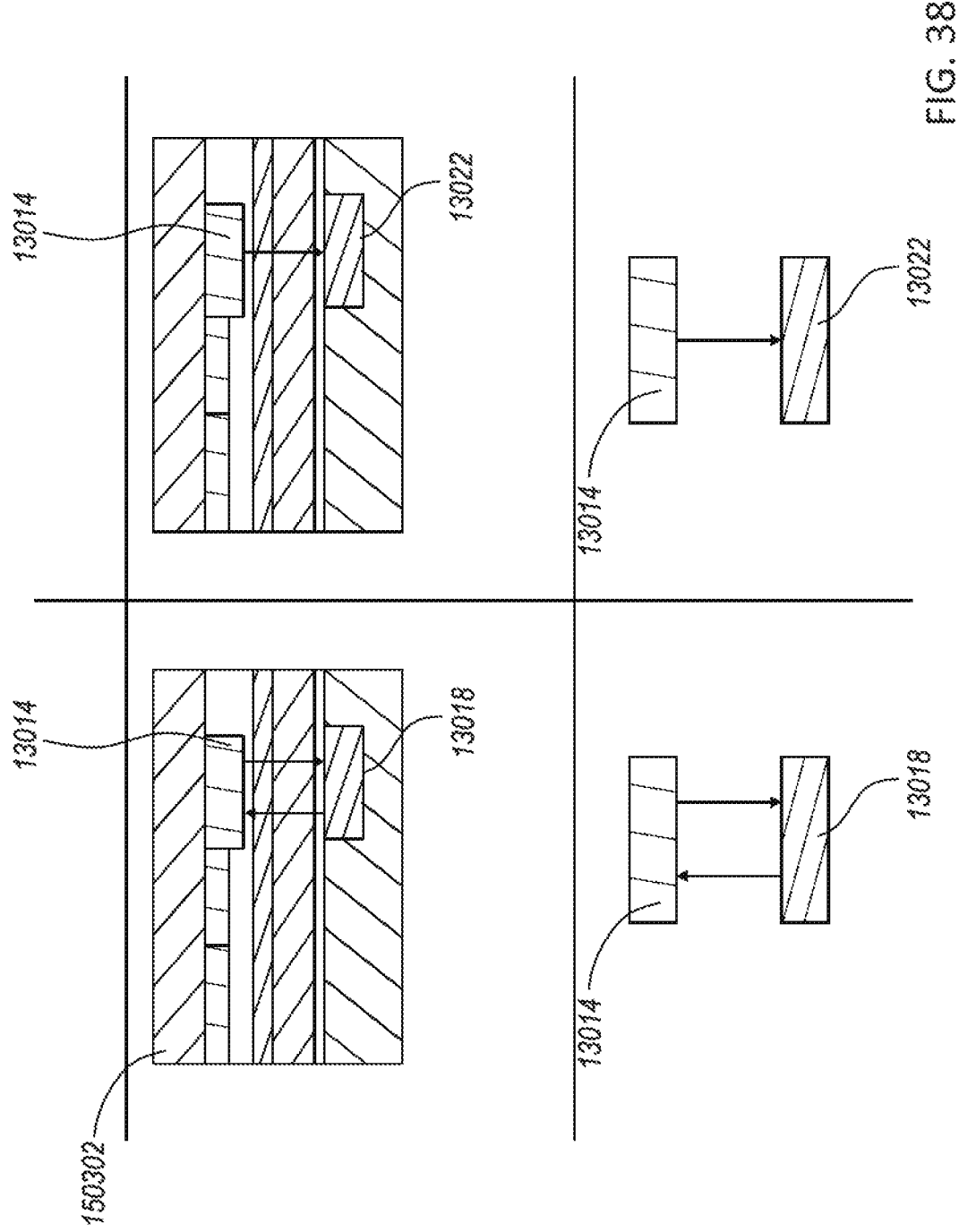
FIG. 38 illustrates example power and data communication.

FIG. 38 provides isolated views of communications between arrays in a surgical staple and surgical staple cartridge. As shown, in a first example illustrated on the left of the figure, a sensing array 13012 comprised in an elongated channel 150302 aligns with a communication device, which may be an RFID chip 13018, in the surgical staple cartridge 13012. In an example, both data and power may be communicated between the sensing array 13014 and RFID chip 13018. Data may be communicated to and from the RFID chip 13018 and power may be communicated from the array 13014 to the RFID chip 13018. In a second example illustrated on the right portion of FIG. 38, the sensing array 13014 is illustrated communicating power to a corresponding array 13022 in the surgical staple cartridge 13012. In this second example, power may be communicated while data may not. Data and power arrays in a stapler may be configured with corresponding communication devices in the cartridge in any suitable combination to send and receive data and/or power as needed.

A surgical instrument may be configured to control the amount and type of communication that may take place between the surgical instrument and a component attached to the surgical instrument. In a first example or tier, a surgical stapler instrument may control the communication between the stapler and a surgical staple cartridge attached thereto so as to allow for one-way communication from the surgical staple cartridge to the surgical stapler. The surgical stapler may communicate data identifying the cartridge and/or data providing status regarding the cartridge. In a second example or tier, a surgical stapler may control the communication between the stapler and a surgical staple cartridge attached thereto to provide for communication of static measurements taken by sensors comprised in the surgical staple cartridge to the surgical stapler. The communications may identify the cartridge and the position of tissue that is being operated on by the surgical staple cartridge. In a third example or tier, a surgical stapler may control the communication between the stapler and a surgical staple cartridge attached thereto to provide continuous communication of data between the staple cartridge and the surgical staple. A surgical staple cartridge may comprise sensors that continuously detect and measure tissue features such as compression in multiple areas or zones and provide continuous measurements to the surgical stapler over time. The surgical stapler may control the surgical staple cartridge to continuously receive such measurements in real time.

Figure 39:
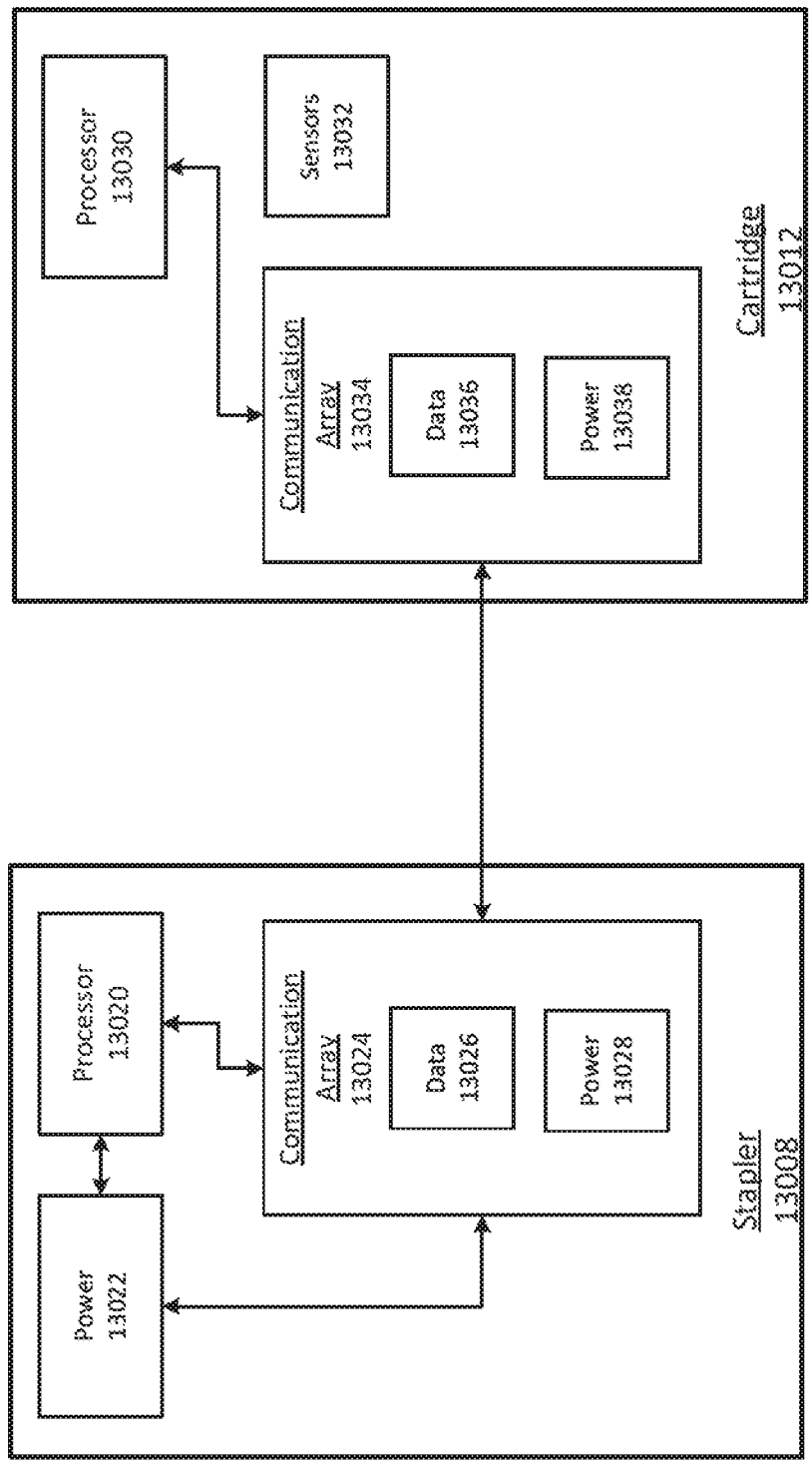
FIG. 39 illustrates an example block diagram depicting components of an example surgical stapler and an example staple cartridge.

FIG. 39 depicts functional components of an example surgical stapler 13008 and staple cartridge 13012. As shown, the surgical stapler 13008 may comprise a processor 13020, a power source 13022, and a communication array 13024. The processor 13020 may be programmed with executable instructions for performing functions attendant to operation of the surgical stapler 13008 including determining communication capability of the surgical stapler 13008 relative to the surgical staple cartridge 13012. The processor 13020 may control the receipt and transmission of data and power to the surgical staple cartridge 13012. The communications array 13024 may comprise one or more data communication arrays 13026 and/or power communication arrays 13028. The processor 13008 may be programmed to control the data communication arrays 13026 and power communication arrays 13028 and thereby control communicating data and power between the surgical stapler 13008 and the staple cartridge 13012. The processor 13020 may control power source 13022 and communication of power via power communications arrays 13028 to the surgical staple cartridge 13012.

The surgical staple cartridge 13012 may comprise a processor 13030, sensors 13032, and a communication array 13034. The processor 13020 may be programmed with executable instructions for performing functions attendant to operation of the surgical staple cartridge 13012 including communication of data and receiving power from the surgical stapler 13008. The processor 13030 may control sensors 13032 to measure and gather data relating to tissue operated on by the surgical staple cartridge 13012 and surgical stapler 13008. The sensors 13032 may be configured to, and may be controlled by processor 13030 to measure and collect data relating to tissue compression. The sensors 13032 may collect data in multiple areas or zones and communicate the data in real time. The communications array 13034 may comprise one or more data communication arrays 13036 and/or power communication arrays 13038. The processor 13030 may be programmed to control the data communication arrays 13036 and power communication arrays 13038 and thereby control communicating data and power between the surgical stapler 13008 and the staple cartridge 13012. The processor 13020 may control sensors 13032 and data communication array 13036 to communicate measurement data to the surgical stapler 13008. The processor may control power communication array 13038 to receive power from surgical stapler 13008.

The surgical stapler 13008 may be programmed to control a communication capability between the surgical staple cartridge 13012 and the surgical stapler 13008. The surgical stapler 13008 may be programmed to determine the type and amount of data and power that may be communicated with the surgical stapler 13008 by a connected component such as surgical staple cartridge 13012. The surgical stapler 13008 may also be programmed to determine the type and amount of data that may be communicated with a separate computing system such as, for example, a surgical hub 106 as described above. The surgical stapler 13008 may control, for example, which of the following communication capabilities or capacities are implemented: one-way communication from the surgical staple cartridge 13012 to the surgical stapler 13008; two-way communication between the surgical staple cartridge 13012 and the surgical stapler 13008; real-time two-way communication relating to measured data; communication of power from the surgical stapler to the surgical staple cartridge 13012; and communication by the surgical stapler 13008 with a separate server system such as, for example, a surgical hub 106.

The surgical stapler 13008 may determine a communication capability based on the value of one or more parameters associated with at least one of the surgical stapler 13008 or the surgical staple cartridge 13012. The surgical stapler 13008 may process values of parameters associated with, for example, the owner or operator of the device, hardware comprised in the surgical stapler 13008 and/or surgical staple cartridge 13012, software comprised in the surgical stapler 13008 and/or surgical staple cartridge 13012, and/or a purchase or subscription level associated with the surgical stapler 13008 and/or surgical staple cartridge 13012. The surgical stapler 13008 may determine a communication capability based on the values of one or more of environmental parameters, interference, system capabilities, or system control parameters. System control parameters may comprise one or more of a software level, a software revision, software authenticity, purchase level, or subscription level. Depending on the value of these or other parameters, the surgical stapler 13008 may determine to implement a particular communication capability including the type of data and manner of communication between the surgical stapler 13008 and the surgical staple cartridge 13012 and/or with a surgical hub 106. For example, a surgical stapler 13008 may determine, based on a parameter indicating the surgical stapler 13008 or the surgical stapler cartridge 13012 is associated with an entry level purchase or subscription, that the communication capability between the surgical stapler 13008 and the staple cartridge 13012 may allow for one-way communication of static data from the surgical staple cartridge 13012 to the surgical stapler 13008. A surgical stapler 13008 may determine, based on a parameter indicating the surgical stapler 13008 or the surgical stapler cartridge 13012 is associated with a medium level purchase or subscription, that the communication capability between the surgical stapler 13008 and the staple cartridge 13012 may allow for two-way communication of data between the surgical staple cartridge 13012 and the surgical stapler 13008. A surgical stapler 13008 may determine, based on a parameter indicating the surgical stapler 13008 or the surgical stapler cartridge 13012 is associated with a relatively high level purchase or subscription, that the communication capability between the surgical stapler 13008 and the staple cartridge 13012 may allow for real-time two-way (e.g., bi-directional) communication of data between the surgical staple cartridge 13012 and the surgical stapler 13008. The surgical stapler 13008 may determine, based on a parameter indicating the surgical stapler 13008 or the surgical staple cartridge 13012 is associated with a higher level purchase or subscription, that the communication capability may comprise two-way communication between the surgical stapler 13008 and the surgical staple cartridge 13012 as well as communication with a server such as the hub server 106. The surgical stapler 13008 may determine based on a parameter associated with a sensing capacity of the surgical staple cartridge 13012 to communicate power from the surgical stapler 13008 to the surgical staple cartridge 13012.

The surgical stapler 13008 may determine the communication capability between the surgical stapler 13008 and the surgical staple cartridge 13012 based on parameters relating to the hardware and/or software comprised in the surgical stapler 13008 and/or surgical staple cartridge 13012. For example, if the surgical staple cartridge 13012 is configured with outdated software, the surgical stapler 13008 may determine that the communication capability with the surgical staple cartridge 13012 may comprise one-way communication of static data from the surgical staple cartridge 13012 to the surgical instrument. If the surgical staple cartridge 13012 is configured with the recently updated software, the surgical stapler 13008 may determine that the communication capability with the surgical staple cartridge 13012 may comprise two-way communication. If the surgical staple cartridge 13012 comprises tissue sensing arrays, the surgical stapler 13008 may determine that the communication capability with the surgical staple cartridge 13012 may comprise real-time data communication with the cartridge, communicating power to the cartridge, and communicating data from the surgical stapler 13008 to a third device such as, for example a surgical hub 106.

Figure 40:
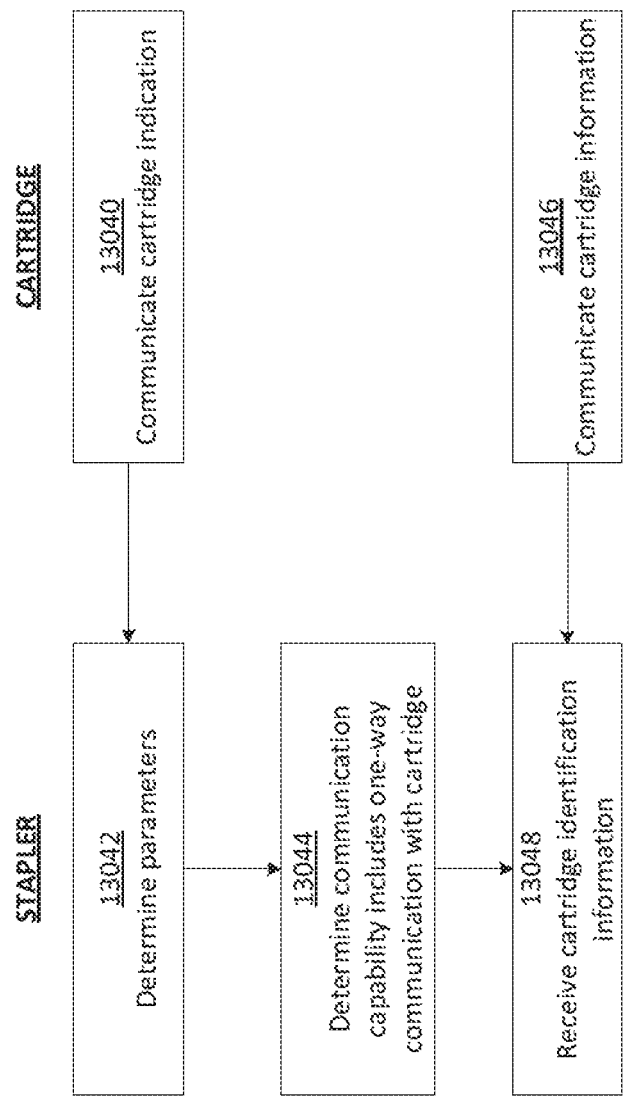
FIG. 40 illustrates example processing for determining communication capabilities.

The surgical stapler 13008 may determine that the communication capability may be a first tier and may comprise one-way data communication from the staple cartridge to the surgical stapler. FIG. 40 depicts a flow diagram for processing associated with a selection of one-way communication capability. As shown, at 13040, a surgical staple cartridge 13012 may be coupled to a surgical stapler 13008 and may communicate an indication that it has coupled. The surgical staple cartridge 13012 may determine that it is physically coupled to the surgical staple cartridge 13012 and, in response, may communicate the indication that it has coupled.

At 13042, the surgical stapler 13008 may determine the value of parameters relevant to determining communication capability. For example, the surgical stapler 13008 may determine values for one or more of: environmental parameters, interference, system capabilities, or system control parameters. System control parameters may comprise one or more of a software level, a software revision, software authenticity, purchase level, or subscription level. The surgical stapler 13008 may determine the operating capacity of the surgical stapler and/or staple cartridge, the current software version operating on the stapler and/or cartridge, and/or the level of purchased or subscribed service associated with the stapler and/or cartridge.

At 13044, the surgical stapler 13008 may determine, based on the determined parameters, the communication capability for interfacing with the surgical staple cartridge 13012 and any additional system. The surgical stapler 13008 may determine, based on a parameter value indicating the surgical stapler 13008 or the surgical staple cartridge 13012 is associated with an entry level purchase or subscription, that the communication capability between the surgical stapler 13008 and the staple cartridge 13012 may allow for one-way communication of static data from the surgical staple cartridge 13012 to the surgical stapler 13008. The surgical stapler 13008 may determine based on a parameter value indicating the surgical stapler 13008 or the surgical staple cartridge 13012 is configured with a non-current software version that the communication capability may allow for one-way communication of static data from the surgical staple cartridge 13012 to the surgical stapler 13008.

At 13046, the surgical staple cartridge 13012 may communicate data to the surgical stapler 13008. The surgical staple cartridge 13012 may employ a data communications array 13036 to communicate data from the surgical staple cartridge 13012 to a data communications array 13026 in the surgical stapler 13008. The data communicated by the surgical staple cartridge 13012 may comprise data relating to the features and characteristics of the staple cartridge 13012. The data communicated by the surgical staple cartridge 13012 and received by the surgical stapler 13008 at block 13048, may comprise one or more of a serial number associated with the staple cartridge, a color associated with the staple cartridge, a length associated with the staple cartridge, or a status associated with the staple cartridge. Where the surgical staple cartridge 13012 comprise a RFID chip as discussed above in connection with FIG. 37A, the data may be transmitted by the RFID chip and received at a communications array 13024 comprised in the surgical stapler 13008.

Figure 41:
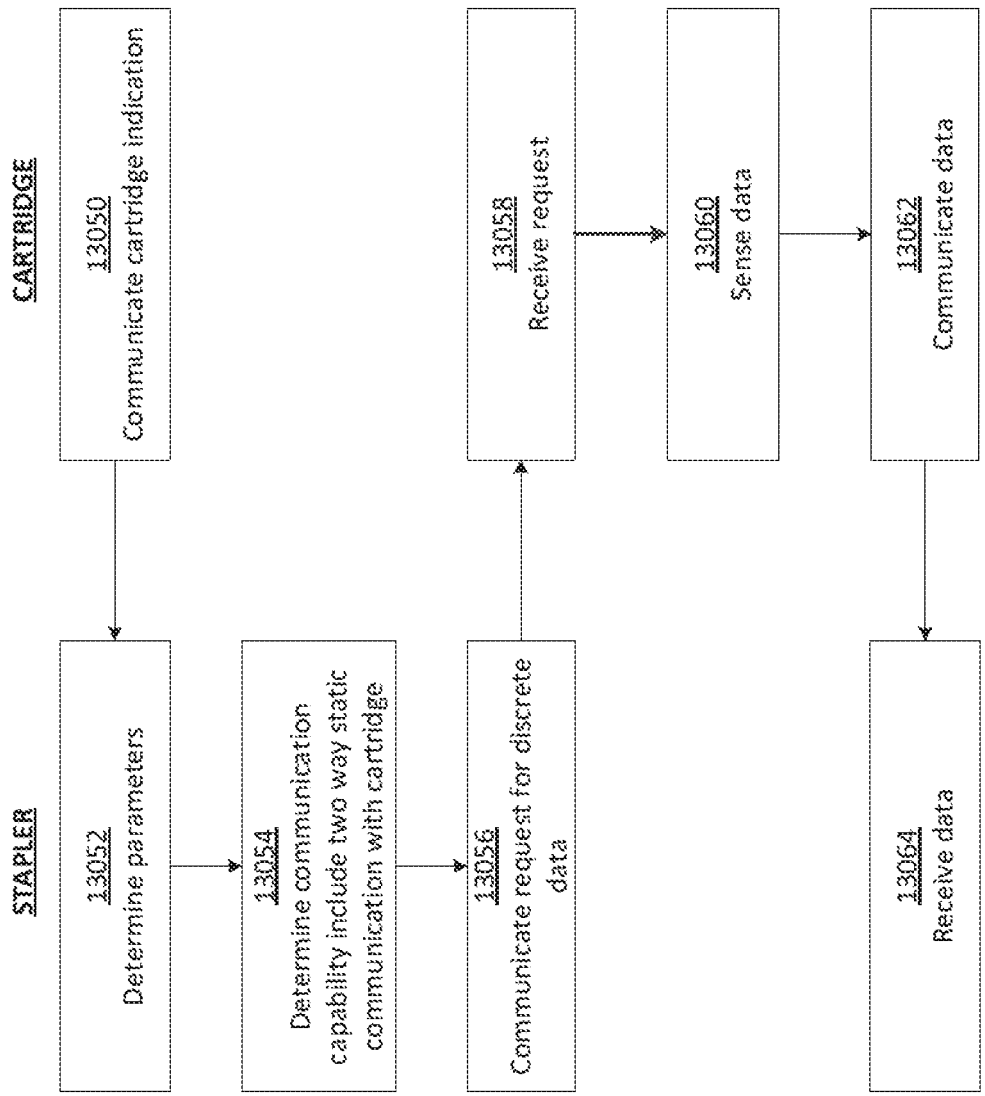
FIG. 41 illustrates example processing for determining communication capabilities.

The surgical stapler 13008 may determine that the communication capability or capacity may be a second tier comprising two-way data communication of static or discrete data readings from the staple cartridge to the surgical stapler. FIG. 41 depicts a flow diagram for processing associated with a selection of two-way data communication of static data as a communication capability. As shown, at 13050, a surgical staple cartridge 13012 may be coupled to a surgical stapler 13008 and may communicate an indication that it has coupled. The surgical staple cartridge 13012 may determine that it is physically coupled to the surgical staple cartridge 13012 and, in response, may communicate the indication that it has coupled.

At 13052, the surgical stapler 13008 may determine parameters relevant to determining communication capability. For example, the surgical stapler 13008 may determine values for one or more of: environmental parameters, interference, system capabilities, or system control parameters relating to the surgical stapler 13008 and/or the surgical stale cartridge 13012. System parameters for the surgical stapler 13008 may comprise, for example, a wiring harness compatibility with the staple cartridge, a software communication level associated with the surgical stapler, and/or a power supply capability associated with the surgical stapler. System parameters for the surgical cartridge may comprise, for example, an antenna array, a power requirement, presence of a local power accumulator, a memory location, and/or a local signal processing capability System control parameters may comprise one or more of a software level, a software revision, software authenticity, purchase level, or subscription level. The surgical stapler 13008 may determine the operating capacity of the surgical stapler and/or staple cartridge, the current software version operating on the stapler and/or cartridge, and/or the level of purchased or subscribed service associated with the stapler and/or cartridge.

At 13054, the surgical stapler 13008 may determine, based on the determined parameter values, the communication capability for interfacing with the surgical staple cartridge 13012 and/or other system. For example, the surgical stapler 13008 may determine, based on a parameter indicating the surgical stapler 13008 or the surgical stapler cartridge 13012 is associated with a medium level purchase or subscription, that the communication capability between the surgical stapler 13008 and the staple cartridge 13012 may allow for two-way communication of discrete data readings between the surgical staple cartridge 13012 and the surgical stapler 13008. The surgical stapler 13008 may determine based on a parameter value indicating the surgical stapler 13008 or the surgical staple cartridge 13012 is configured with a current software version and/or has hardware compatible with two-way communication that the communication capability may allow for two-way communication of static data from the surgical staple cartridge 13012 to the surgical stapler 13008.

At 13056, having determined the communication capability, the surgical stapler 13008 may communicate a request for data to the surgical staple cartridge 13012. The request may specify a request for discrete data readings. The request may specify to provide data items gathered by sensors comprised in the surgical staple cartridge 13012. The surgical stapler 13008 may employ a data communications array 13026 to communicate the request to the surgical staple cartridge 13012.

At 13058, the surgical staple cartridge 13012 may receive the request. The request may be received by the surgical staple cartridge 13012 using data communication array 13036. In response to the request, at block 13060, the surgical staple cartridge 13012 senses data relevant to the request. For example, the surgical staple cartridge 13012 may employ sensors to gather data relating to tissue presently being operated on by the surgical staple cartridge 13012 and surgical stapler 13008. The sensor readings may identify which portions of the surgical staple cartridge 13012 are engaged with tissue. The data may indicate a location of the tissue in relation to the surgical staple cartridge 13012. The sensor readings may identify pressure readings regarding the amount of pressure applied to tissue and the location of the pressure readings. The sensor readings may comprise data relating to tissue impedance, tissue location, tissue thickness, and/or tissue viscoelasticity.

At 13062, the surgical staple cartridge 13012 may communicate data readings to the surgical stapler 13008. The communicated data may comprise data items corresponding to the sensor readings made by the surgical staple cartridge 13012. The data items may correspond to readings made at discrete points in time. The data items may comprise data associated with tissue location relative to the surgical staple cartridge 13012 and/or the surgical stapler 13008. The tissue location data may be a static tissue location. The surgical staple cartridge 13012 may employ a data communications array 13036 to communicate data from the surgical staple cartridge 13012 to a data communications array 13026 in the surgical stapler 13008.

At 13064, the surgical stapler 13008 may receive the transmitted data. The surgical stapler 13008 may then use the received data in its operation. For example, the surgical stapler 13008 may use tissue readings and tissue compression data in a display for the operator. The surgical stapler 13008 may process the data to determine whether the surgical stapler is properly situated relative to tissue to perform a stapling operation.

Figure 42:
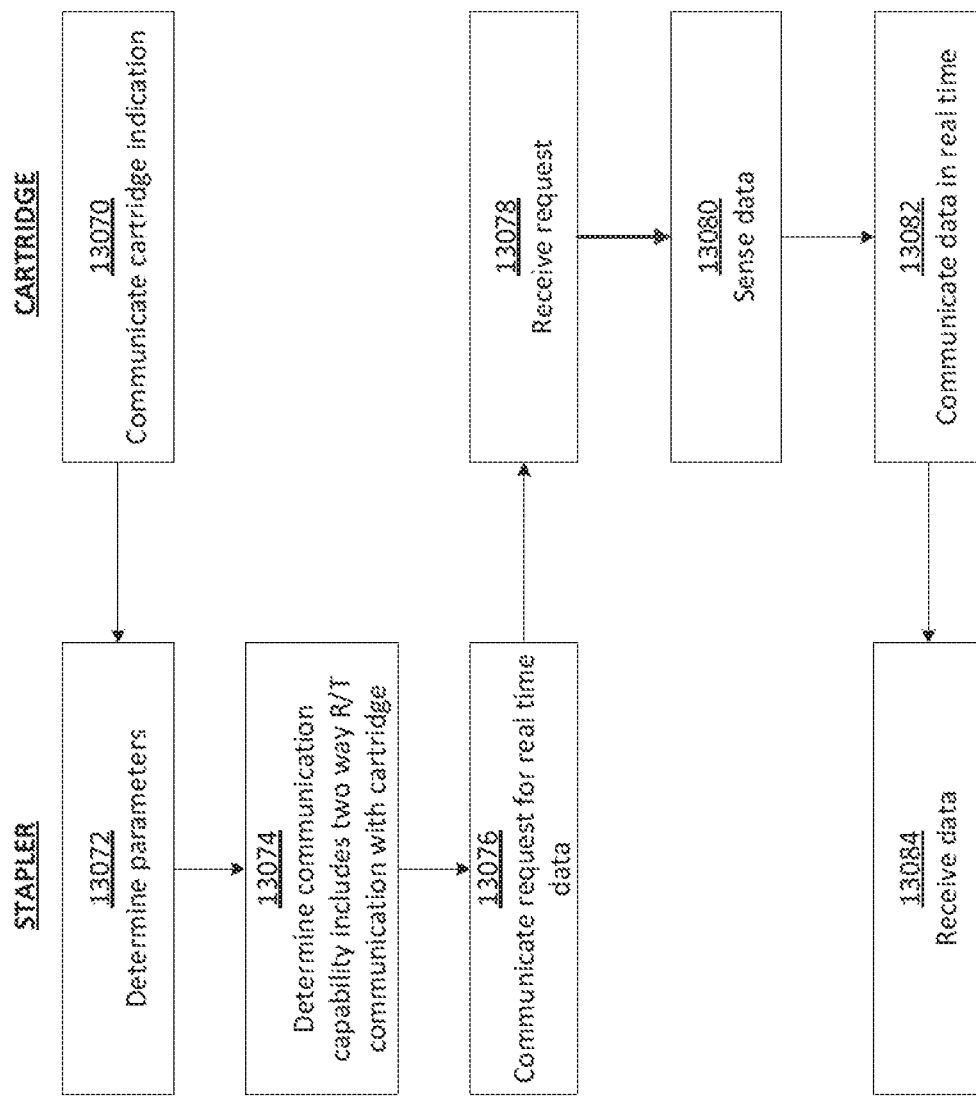
FIG. 42 illustrates example processing for determining communication capabilities.

The surgical stapler 13008 may determine that the communication capacity or capability may be a third tier comprising two-way data communication relating to real-time data readings from the staple cartridge to the surgical stapler. FIG. 42 depicts a flow diagram for processing associated with a selection of two-way data communication of real-time data as a communication capability. As shown, at 13070, a surgical staple cartridge 13012 may be coupled to a surgical stapler 13008 and may communicate an indication that it has coupled. The surgical staple cartridge 13012 may determine that it is physically coupled to the surgical staple cartridge 13012 and, in response, may communicate the indication that it has coupled.

At 13072, the surgical stapler 13008 may determine parameters relevant to determining communication capability. For example, the surgical stapler 13008 may determine values for one or more of: environmental parameters, interference, system capabilities, or system control parameters relating to the surgical stapler 13008 and/or the surgical stale cartridge 13012. System parameters for the surgical stapler 13008 may comprise, for example, a wiring harness compatibility with the staple cartridge, a software communication level associated with the surgical stapler, and/or a power supply capability associated with the surgical stapler. System parameters for the surgical cartridge may comprise, for example, an antenna array, a power requirement, presence of a local power accumulator, a memory location, and/or a local signal processing capability. System control parameters may comprise one or more of a software level, a software revision, software authenticity, purchase level, or subscription level. The surgical stapler 13008 may determine the operating capacity of the surgical stapler and/or staple cartridge, the current software version operating on the stapler and/or cartridge, and/or the level of purchased or subscribed service associated with the stapler and/or cartridge.

At 13074, the surgical stapler 13008 may determine, based on the determined parameters, the communication capability for interfacing with the surgical staple cartridge 13012 and/or other system such as a surgical hub 106. The surgical stapler 13008 may determine, based on a parameter indicating the surgical stapler 13008 or the surgical stapler cartridge 13012 is associated with a relatively high level purchase or subscription, that the communication capability between the surgical stapler 13008 and the staple cartridge 13012 may allow for real-time two-way (e.g., bi-directional) communication of data between the surgical staple cartridge 13012 and the surgical stapler 13008. The surgical stapler 13008 may determine based on a parameter value indicating the surgical stapler 13008 or the surgical staple cartridge 13012 is configured with a current software version that the communication capability may allow for two-way communication and communication in real time of data collected from sensors in the surgical staple cartridge 13012.

At 13076, having determined the communication capability, the surgical stapler 13008 may communicate a request for data to the surgical staple cartridge 13012. The request may specify a request for two-way communication relating to real-time data readings. The surgical stapler 13008 may employ a data communications array 13026 to communicate the request to the surgical staple cartridge 13012.

At 13078, the surgical staple cartridge 13012 may receive the request. The request may be received by the surgical staple cartridge 13012 using data communication array 13036. In response to the request, at block 13080, the surgical staple cartridge 13012 may sense data relevant to the request. For example, the surgical staple cartridge 13012 may employ sensors 13032 to gather data relating to tissue presently being operated on by the surgical staple cartridge 13012 and surgical stapler 13008. The sensor readings may identify which portions of the surgical staple cartridge 13012 are engaged with tissue. The data may indicate a location of the tissue in relation to the surgical staple cartridge 13012. The sensor readings may identify pressure readings regarding the amount of pressure applied to tissue and the location of the pressure readings. The sensor readings may comprise data relating to tissue impedance, tissue location, tissue thickness, and/or tissue viscoelasticity.

At 13082, the surgical staple cartridge 13012 may communicate data readings to the surgical stapler 13008. The communicated data may comprise data items corresponding to the sensor readings made by the surgical staple cartridge 13012. The data items may correspond to continuous readings made in real time. The data items may correspond to sensor readings relating to tissue made across time. The surgical staple cartridge 13012 may employ a data communications array 13036 to communicate data from the surgical staple cartridge 13012 to a data communications array 13026 in the surgical stapler 13008. The communications may be made continuously in real time to reflect real time measurements made by sensors in the surgical staple cartridge 13012.

At 13084, the surgical stapler 13008 may receive the transmitted data. The data may be received in real time and continuously. The surgical stapler 13008 may then use the received data in its operation. For example, the surgical stapler 13008 may use tissue readings and tissue compression data in a display to the operator and/or to determine whether the surgical stapler is properly situated to perform a stapling operation. The surgical stapler 13008 may use the received data to determine characteristics of tissue being operated on by the surgical stapler 13008 and surgical staple cartridge 13012. The surgical stapler 13008 may use the received data to determine characteristics relating to tissue type, organ type, and/or tissue stiffness.

The surgical stapler 13008 may continuously monitor the characteristics of the tissue operated on by the surgical stapler 13008. The surgical stapler 13008 may compare the monitored characteristics to one or more threshold values. If the surgical stapler 13008 determines a threshold has been met, the surgical stapler may determine to perform a function such as, for example, perform a mechanical or electrical operation. For example, if the received data relates to a tissue thickness, and the thickness satisfies a threshold for stapling, the surgical stapler 13008 may indicate to the operator that a stapling operation is permitted.

Figure 43:
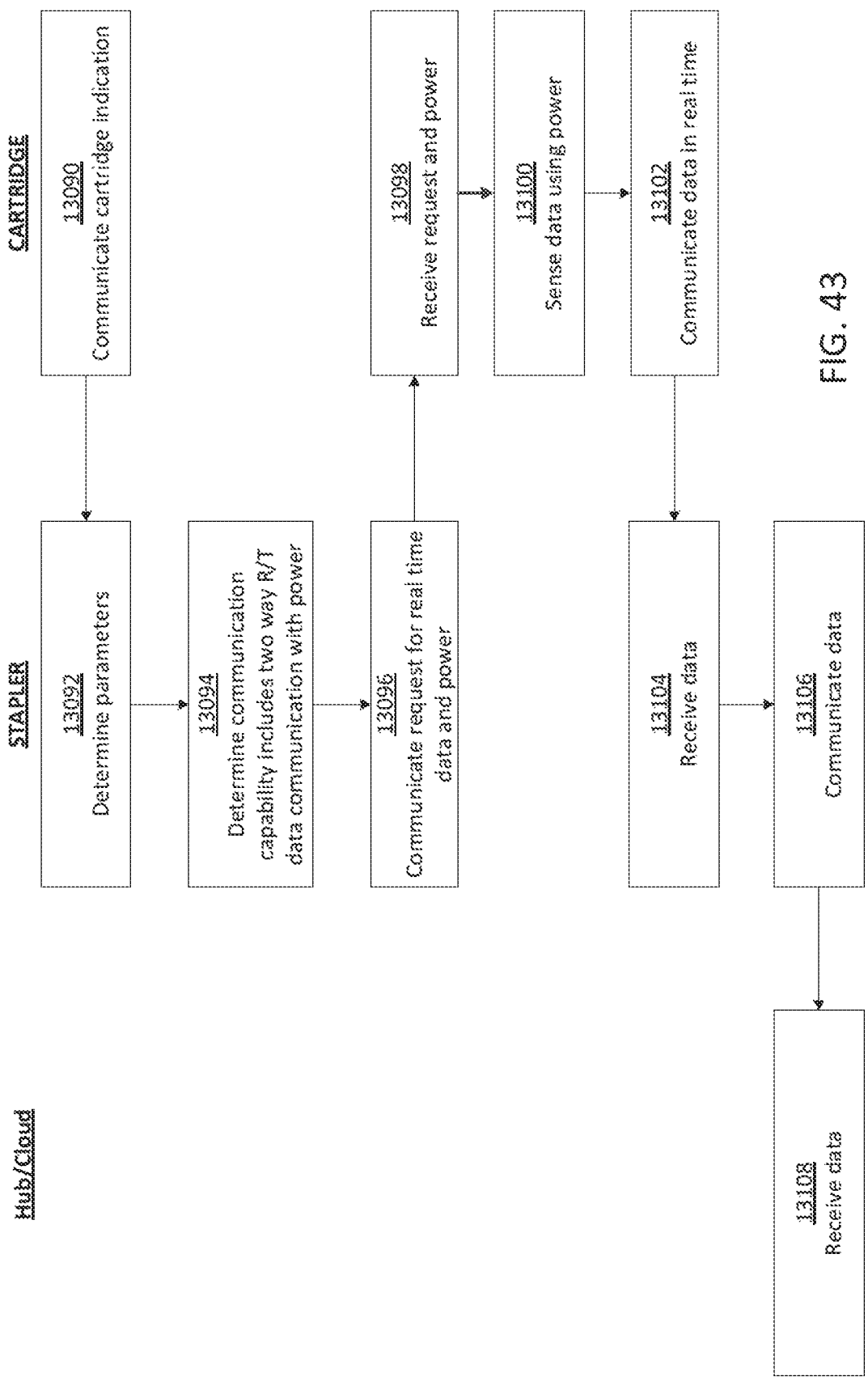
FIG. 43 illustrates example processing for determining communication capabilities.

The surgical stapler 13008 may determine that the communication capability or capacity may be a tier comprising two-way data communication relating to real-time data readings from the surgical staple cartridge 13012 to the surgical stapler 13008, power communication from the surgical stapler 13008 to the surgical staple cartridge 13012, and data communication to an external system such as a surgical hub 106. FIG. 43 depicts a flow diagram for processing associated with a selection of communication capability comprising two-way data communication of real-time data, power communication, and communication with an external system. As shown, at 13090, a surgical staple cartridge 13012 may be coupled to a surgical stapler 13008 and may communicate an indication that it has coupled. The surgical staple cartridge 13012 may determine that it is physically coupled to the surgical staple cartridge 13012 and, in response, may communicate the indication that it has coupled.

At 13092, the surgical stapler 13008 may determine parameters relevant to determining communication capability. For example, the surgical stapler 13008 may determine values for one or more of: environmental parameters, interference, system capabilities, or system control parameters relating to the surgical stapler 13008 and/or the surgical stale cartridge 13012. System parameters for the surgical stapler 13008 may comprise, for example, a wiring harness compatibility with the staple cartridge, a software communication level associated with the surgical stapler, and/or a power supply capability associated with the surgical stapler. System parameters for the surgical cartridge may comprise, for example, an antenna array, a power requirement, presence of a local power accumulator, a memory location, and/or a local signal processing capability System control parameters may comprise one or more of a software level, a software revision, software authenticity, purchase level, or subscription level. The surgical stapler 13008 may determine the operating capacity of the surgical stapler and/or staple cartridge, the current software version operating on the stapler and/or cartridge, and/or the level of purchased or subscribed service associated with the stapler and/or cartridge.

At 13094, the surgical stapler 13008 may determine, based on the determined parameters, the communication capability for interfacing with the surgical staple cartridge 13012 and an external system. The surgical stapler 13008 may determine, based on a parameter indicating the surgical stapler 13008 or the surgical staple cartridge 13012 is associated with a higher level purchase or subscription, that the communication capability may comprise two-way communication between the surgical stapler 13008 and the surgical staple cartridge 13012 as well as communication with a server such as hub server. The surgical stapler 13008 may also determine based on a parameter associated with sensors comprised in the surgical staple cartridge 13012 to communicate power from the surgical stapler 13008 to the surgical staple cartridge 13012.

At 13096, having determined the communication capability, the surgical stapler 13008 may communicate a request for data to the surgical staple cartridge 13012. The request may specify a request for two-way communication relating to real-time data readings. The surgical stapler 13008 may employ a data communications array 13026 to communicate the request to the surgical staple cartridge 13012. The surgical stapler 13008 may also communicate power to the surgical staple cartridge 13012. The surgical stapler 13008 may employ a power communication array 13028 to communicate the power. The surgical staple cartridge 13012 may use the received power to operate sensors for collecting data.

At 13098, the surgical staple cartridge 13012 receives the request for data and the power. The request may be received by the surgical staple cartridge 13012 using data communication array 13036. The power may be received at power communication array 13038.

In response to the request, at 13100, the surgical staple cartridge 13012 may sense data relevant to the request. For example, the surgical staple cartridge 13012 may employ sensors 13032 to gather data relating to tissue presently being operated on by the surgical staple cartridge 13012. The sensor readings may identify which portions of the surgical staple cartridge 13012 are engaged with tissue. The data may indicate a location of the tissue in relation to the surgical staple cartridge 13012. The sensor readings may identify pressure readings regarding the amount of pressure applied to tissue and the location of the pressure readings. The surgical staple cartridge 13012 may employ the received power to fulfill the request. The surgical staple cartridge 13012 may employ the received power to operate sensors that are used to collect the requested data.

At 13102, the surgical staple cartridge 13012 communicates data readings to the surgical stapler 13008. The communicated data may comprise data items corresponding to the sensor readings made by the surgical staple cartridge 13012. The data items may correspond to continuous readings made in real time. The surgical staple cartridge 13012 may employ a data communications array 13036 to communicate data from the surgical staple cartridge 13012 to a data communications array 13026 in the surgical stapler 13008. The communications may be made continuously in real time to reflect real time measurements made by sensors in the surgical staple cartridge 13012.

At 13104, the surgical stapler 13008 receives the transmitted data. The data may be received in real time and continuously. The surgical stapler 13008 may use the received data in its operation. For example, the surgical stapler 13008 may display tissue readings and tissue compression data and/or determine whether the surgical stapler is properly situated to perform a stapling operation. The surgical stapler 13008 may use the received data to determine characteristics of tissue being operated on by the surgical stapler 13008 and surgical staple cartridge 13012. The surgical stapler 13008 may use the received data to determine characteristics relating to tissue type, organ type, and/or tissue stiffness. The surgical stapler 13008 may employ artificial intelligence processing in determining aspects of the tissue from the received data or to otherwise process the received data.

The surgical stapler 13008 may continuously monitor the characteristics of the tissue operated on by the surgical stapler 13008. The surgical stapler 13008 may compare the monitored characteristics to one or more threshold values. If the surgical stapler 13008 determines a threshold has been met, the surgical stapler may determine to perform a function such as, for example, perform a mechanical or electrical operation. For example, if the received data relates to a tissue thickness, and the thickness satisfies a threshold for stapling, the surgical stapler 13008 may indicate to the operator that a stapling operation is permitted.

At 13106, the surgical stapler 13008 may communicate data received from the surgical staple cartridge 13012 or derived from the received data to an external system such as, for example a surgical hub 106. For example, the surgical stapler 13008 may communicate data relating to tissue measurements to the surgical hub 106 for further analysis.

At 13108, the surgical hub 106 may receive the data. The surgical hub 106 may store and process the data. For example, the surgical hub 106 may determine, based on the received data, to respond to the surgical stapler 13080 with instructions for further processing along with data to be used in performing the instructions.

Accordingly, systems and techniques are disclosed for controlling the communication capabilities between a surgical instrument such as, for example, a surgical stapler and a removeable component such as, for example, staple cartridge. A surgical instrument may determine one or more parameters associated with the surgical instrument and the removable component. The surgical instrument may determine the type and degree of communication that may take place between the surgical instrument and the removable component based on the one or more parameters.

The combination of a programmable or smart Endocutter with a smart or intelligent cartridge may establish communications in multiple different manners. Each of these levels or tiers of communication interconnection may be dependent on a number of smart stapler aspects (e.g., wiring harness compatibility with needs of the cartridge, software communication level of the instrument, communication array capabilities for signal processing, power supply capabilities, subscription level, etc.) as well as a number of cartridge capabilities (e.g., antenna array, power requirements, presence of a local power accumulator or memory location, and local signal processing, such as described, for example, in U.S. Pat. No. 10,695,081 titled "Time Dependent Evaluation of Sensor Data to Determine Stability, Creep, and Viscoelastic Elements or Measures," the contents of which are hereby incorporated by reference in their entirety). The systems may connect in one of several tiered manners which may control the capabilities of the cartridge that the instrument may employ. By way of example, the level of subscription an institution has purchased may be used to determine a level of software and interconnection with a local hub system that the instrument may employ. An operator of an instrument may have the option of disabling the function if the function is unlikely to provide a benefit for the planned surgical procedure which may allow the device to perform in its base or tier 1 level of functionality. Depending on the cost structure of the software, this may allow the operator to pull the desired hardware to increase operating room efficiency while allowing the surgeon to use the functions needed to complete the case.

The invention claimed is:

1. A surgical instrument comprising:
 a removable staple cartridge coupled with the surgical instrument; and
 a processor configured to:
 determine one or more parameters associated with software associated with at least one of the surgical instrument or the removable staple cartridge, the removable staple cartridge communicatively coupled with the surgical instrument; and
 determine communication capability between the surgical instrument and the removable staple cartridge based on the one or more parameters associated with software associated with at least one of the surgical instrument or the removable staple cartridge.

2. The surgical instrument of claim 1,
 wherein the surgical instrument is a surgical stapler.

3. The surgical instrument of claim 1,
 wherein the processor configured to determine communication capability between the surgical instrument and the removable staple cartridge is further configured to determine one or more of: whether communication between the surgical instrument and the removable staple cartridge is uni-directional or bi-directional; or whether power is communicated from the surgical instrument to the removable staple cartridge.

4. The surgical instrument of claim 1,
 wherein the processor configured to determine communication capability between the surgical instrument and the removable staple cartridge based on the one or more parameters associated with software associated with at least one of the surgical instrument or the removable staple cartridge is configured to determine communication capability between the surgical instrument and the removable staple cartridge based on parameters associated with software associated with the removable staple cartridge.

5. The surgical instrument of claim 1,
 wherein the parameters associated with software associated comprise parameters indicating one or more of a software level, a software revision, software authenticity, or purchase level.

6. The surgical instrument of claim 1,
wherein the processor configured to determine communication capability between the surgical instrument and the removable staple cartridge is configured to determine one-way data communication from the removable staple cartridge to the surgical instrument is available.

7. The surgical instrument of claim 1,
wherein the processor configured to determine communication capability between the surgical instrument and the removable staple cartridge is configured to determine two-way communication between the removable staple cartridge and the surgical instrument is available.

8. The surgical instrument of claim 7,
wherein the processor configured to determine communication capability between the surgical instrument and the removable staple cartridge is configured to determine real-time communication between the removable staple cartridge and the surgical instrument is available.

9. A surgical instrument comprising:
a removable staple cartridge communicatively coupled with the surgical instrument; and
a processor configured to:
determine one or more parameters associated with software associated with at least one of the surgical instrument or the removable staple cartridge, the removable staple cartridge communicatively coupled with the surgical instrument; and
determine, based on the one or more parameters associated with software associated with at least one of the surgical instrument or the removable staple cartridge, two-way communication between the removable staple cartridge and the surgical instrument is available.

10. The surgical instrument of claim 9,
wherein the processor configured to determine the one or more parameters associated with software associated with at least one of the surgical instrument or the removable staple cartridge is configured to determine software associated with at least one of the surgical instrument or the removable staple cartridge is associated with a purchase level or a subscription level.

11. The surgical instrument of claim 9,
wherein the processor configured to determine two-way communication between the removable staple cartridge and the surgical instrument is available is configured to determine at least one of the surgical instrument or the removable staple cartridge is configured with software compatible with two-way communication.

12. The surgical instrument of claim 9, further comprising:
a communication array, the communication array configured to communicate instructions and data to the removable staple cartridge and to receive data from the removable staple cartridge.

13. The surgical instrument of claim 12,
wherein the processor is further configured to receive data from the removable staple cartridge via the communication array,
wherein the received data relates to sensor readings performed by the removable staple cartridge.

14. The surgical instrument of claim 13,
wherein the processor is further configured to process the received data to determine if the surgical instrument is properly situated relative to tissue.

15. A surgical instrument comprising:
a removable staple cartridge communicatively coupled with the surgical instrument; and
a processor configured to:
determine one or more parameters associated with software associated with at least one of the surgical instrument or the removable staple cartridge, the removable staple cartridge communicatively coupled with the surgical instrument; and
determine, based on the one or more parameters associated with software associated with at least one of the surgical instrument or the removable staple cartridge, real-time two-way communication between the removable staple cartridge and the surgical instrument is available.

16. The surgical instrument of claim 15,
wherein the processor configured to determine the one or more parameters associated with software associated with at least one of the surgical instrument or the removable staple cartridge is configured to determine software associated with at least one of the surgical instrument or the removable staple cartridge is associated with a purchase level or a subscription level.

17. The surgical instrument of claim 15, further comprising:
a communication array, the communication array configured to communicate instructions and data to the removable staple cartridge and to receive data from the removable staple cartridge; and
a power communication array, the power communication array configured to communicate power to the removable staple cartridge.

18. The surgical instrument of claim 17,
wherein the processor is further configured to:
receive real-time data from the removable staple cartridge via the communication array;
monitor the received real-time data; and
communicate the received real-time data to a surgical hub.

* * * * *